(12) United States Patent
Wilhelm et al.

(10) Patent No.: US 9,493,428 B2
(45) Date of Patent: Nov. 15, 2016

(54) PROCESS FOR THE PREPARATION OF A CHIRAL COMPOUND

(75) Inventors: Thorsten Wilhelm, Kundle/Tyrol (AT); Martin Langner, Kundle/Tyrol (AT)

(73) Assignee: SANDOZ AG, Basel (CH)

( * ) Notice: Subject to any disclaimer, the term of this patent is extended or adjusted under 35 U.S.C. 154(b) by 203 days.

(21) Appl. No.: 14/125,341

(22) PCT Filed: Jun. 14, 2012

(86) PCT No.: PCT/EP2012/061346
§ 371 (c)(1),
(2), (4) Date: Apr. 8, 2014

(87) PCT Pub. No.: WO2012/172015
PCT Pub. Date: Dec. 20, 2012

(65) Prior Publication Data
US 2014/0303184 A1 Oct. 9, 2014

(30) Foreign Application Priority Data

Jun. 16, 2011 (WO) .................. PCT/EP2011/060048

(51) Int. Cl.
C07D 249/12 (2006.01)
A61K 31/496 (2006.01)
C07D 249/08 (2006.01)

(52) U.S. Cl.
CPC ........... *C07D 249/12* (2013.01); *A61K 31/496* (2013.01); *C07D 249/08* (2013.01)

(58) Field of Classification Search
None
See application file for complete search history.

(56) References Cited

U.S. PATENT DOCUMENTS

| | | | |
|---|---|---|---|
| 4,957,730 A | 9/1990 | Bohn et al. | |
| 5,403,937 A | 4/1995 | Saksena et al. | |
| 5,486,625 A | 1/1996 | Leong et al. | |
| 5,595,872 A | 1/1997 | Wetterau | |
| 5,693,626 A | 12/1997 | Saksena et al. | |
| 5,710,154 A | 1/1998 | Saksena et al. | |
| 5,714,490 A | 2/1998 | Saksena et al. | |
| 5,834,472 A | 11/1998 | Sangekar et al. | |
| 5,972,381 A | 10/1999 | Sangekar et al. | |
| 6,355,801 B1 | 3/2002 | Giesinger et al. | |
| 6,958,337 B2 | 10/2005 | Andrews et al. | |
| 2010/0197621 A1 | 8/2010 | Henry et al. | |

FOREIGN PATENT DOCUMENTS

| | | | |
|---|---|---|---|
| EP | 0736030 A1 | 10/1996 | |
| EP | 1230231 B1 | 8/2002 | |
| EP | 01394162 | 3/2004 | |
| WO | 9309114 | 5/1993 | |
| WO | 9425452 A1 | 11/1994 | |
| WO | 95/17407 | 6/1995 | |
| WO | 9516658 A1 | 6/1995 | |
| WO | 9517407 A1 | 6/1995 | |
| WO | 96/33178 | 10/1996 | |
| WO | 9633163 | 10/1996 | |
| WO | 9633178 | 10/1996 | |
| WO | 9638443 | 12/1996 | |
| WO | 9700255 A1 | 1/1997 | |
| WO | 9722579 | 6/1997 | |
| WO | 9722710 A1 | 6/1997 | |
| WO | 9733178 | 9/1997 | |
| WO | 9918097 | 4/1999 | |
| WO | 02080678 | 10/2002 | |
| WO | 2005/075473 | 1/2005 | |
| WO | 2005117831 | 12/2005 | |
| WO | 2006007540 | 1/2006 | |
| WO | 2007/122156 | 4/2007 | |
| WO | 2007/143390 | 12/2007 | |
| WO | 2008/136279 | 4/2008 | |
| WO | 2009/058267 | 10/2008 | |
| WO | 2009/141837 | 5/2009 | |
| WO | 2009/129297 | 10/2009 | |

(Continued)

OTHER PUBLICATIONS

International Preliminary Report on Patentability issued in PCT/EP2012/061446, Oct. 9, 2013, pp. 1-8.

(Continued)

*Primary Examiner* — Kamal Saeed
(74) *Attorney, Agent, or Firm* — Jeffrey S. Melcher; Manelli Selter PLLC

(57) ABSTRACT

The present invention relates to a process for the preparation of a compound of formula (V), in particular posaconazole, wherein said process comprises the steps of (1) providing a mixture comprising a compound of formula (IV), a protic solvent system, and a suitable base; and (2) heating the mixture of (1) to obtain a mixture comprising the compound of formula (V).

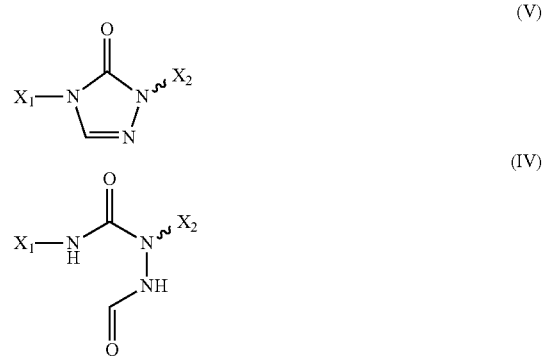

49 Claims, 5 Drawing Sheets

(56) References Cited

FOREIGN PATENT DOCUMENTS

Figure 1:
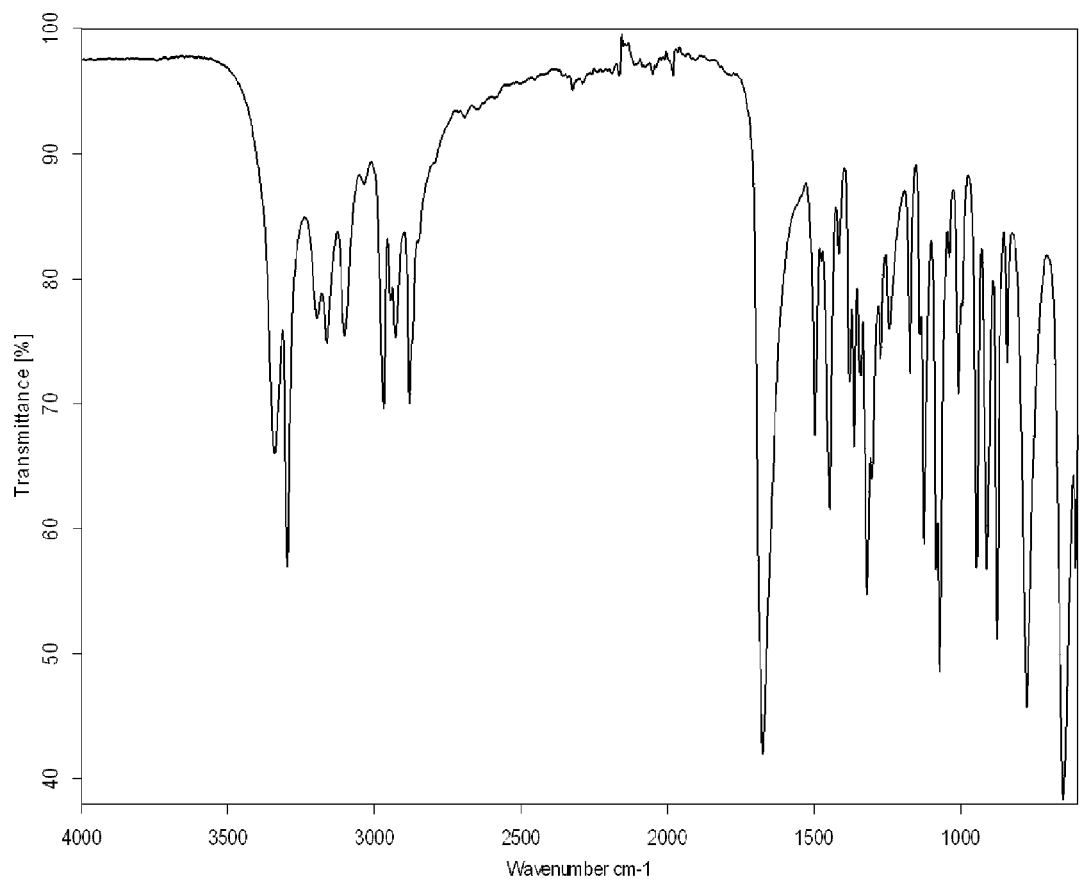

| WO | 2010000668 | 1/2010 |
|---|---|---|
| WO | 2011/144653 | 11/2011 |
| WO | 2011/144655 | 11/2011 |
| WO | 2011/144656 | 11/2011 |
| WO | 2011/144657 | 11/2011 |
| WO | 2012/172015 | 12/2012 |
| WO | 2013/186320 | 12/2013 |

OTHER PUBLICATIONS

Parmee, "Human beta3 adreneergic receptor containing cyclic ureidobenzenesulonafides," Bioorganic & Medicinal Chemistry Letters, vol. 9, 1999, pp. 749-745, XP002648199.
International Search Report issued in PCT/EP2012/061446, Aug. 1, 2012, pp. 1-9.
Written Opinion issued in PCT/EP2012/061446, Jun. 20, 2013, pp. 1-5.
Blundell et al., Synlett 1994, pp. 263-265.
Brown et al., J. Chem. Soc. 2003, 125 (36), 10808-10809.
Cordova et al., Chem. Eur. J. 2004, 10 (15), 3673-3684.
Di Santo et al., "antifungal estrogen-like imidazoles. Synthesis and antifungal activities of thienyl and 1H-pyrrolyl derivatives of 1-aryl-2-(1H-imidazol-1-yl)ethane", European Journal of Medicinal Chemistry, Editions Scientifique Elsevier, Paris, FR, vol. 32, No. 2, Nov. 1, 1997, pp. 143-149.
Greene et al., Protective Groups in Organic Synthesis:, 2nd ed., John Wiley & Sons, New York 1991 10-142.
Greene et al., Protective Groups in Organic Synthesis:, 3rd ed., Wiley-Interscience (1999).
Hayashi et al., J. Org. Chem. 2005, 69 (18), 5966-5973.
Hepperle et al., Tetrahedron Lett. 2002, 43, 3359-3363.
Huang et al., Organic Letters 2004, 6 (25) 4795-4798.
Kurome et al., "Total Synthesis of an Antifungal Cyclic Depsipeptide Aureobasidin A", Tetrahedron, Elsevier Science Publishers. Amsterdam, NL, vol. 52, No. 12. Mar. 18, 1996, pp. 4327-4346.
Na Y-M et al., "Synthesis and antifungal activity of new 1-halogenbenzyl-3-imidazoly 1methylindole derivatives", European Journal of Medicinal Chemistry, Editions Scientifique Elsevier, Paris, FR, vol. 38, No. 1, Jan. 1, 2003, pp. 75-87.
Peterson, "Carbonyl olefination reaction using silyl-substituted organometallic compounds", J. Org. Chem (1968) 33 (2) pp. 780-784.
Remington's Pharmaceutical Sciences, 15th Ed., Mack Publishing Co., New Jersey (1991).
Saksena et al., Tetrahedron Lett. 2004, 45 (44), 8249-8251.
Tetrahedron Letters 32 (1991). pp. 7545-7548.
Xianhai Huang et al., "Manipulation of N,O-Nucleophilicity: Efficient Formation of 4-N-Substituted 2,4-Dihydro-3H-1, 2, 4-Triazolin-3-ones", Organic Letters, American Chemical Society, US, vol. 6, No. 25, Nov. 10, 2004, pp. 4795-4798.
International Search Report and Written Opinion Mailed Sep. 9, 2011 in PCT/EP2011/058035.
International Search Report and Written Opinion Mailed Aug. 4, 2011 in PCT/EP2011/058036.
International Search Report and Written Opinion Mailed Aug. 5, 2011 in PCT/EP2011/058039.
International Search Report and Written Opinion Mailed Jul. 13, 2011 in PCT/EP2011/058033.
Serajuddin, Abu. Advanced Drug Delivery Reviews 59 (2007) pp. 603-616.
Reichardt, Chr. Solvents and Solvent Effects in Organic Chemistry. 3rd ed. Wiley-VCH. (2004) pp. 418-421.
Hacker, "Aromatic 2-(Thio)ureidocarboxylic Acids as New Family of Modulators of Multidrug Resistance-Associated Protein 1: Synthesis, Biological Evaluation, and Structure-Activity Relationships," Journal of Medicinal Chemistry, 2009, vol. 52, No. 15, pp. 4587-4593.
Office Action issued in Chinese Patent Application Serial No. 201180024340.2, Dec. 8, 2014, pp. 1-13, translation included.
Weicheng Thou et al., Survey of Syntheses of Azole Antifungals. Chinese Journal of Pharmaceuticals, vol. 37, No. 2, pp. 125-133, Dec. 31, 2006.
Sixi Wang, Synthesis of SIPI-4678 and Voriconazole, The Master Degree Theses of the Shanghai Institute of Parmaceutical Industry, pp. 10-13, Mar. 2007.
Sixi, Wang, Synthesis of SIPI-4678 and Voriconazole, The Master Degree Theses of the Shanghai Institute of Pharmaceutical Industry, pp. 9-17, Jan. 24, 2007.
Chinese Office Action issued in Application No. 201180024340.2, Mar. 24, 2014, pp. 1-13, and translation.
Chinese Office Action issued in Application No. 201180024363.3, Jan. 17, 2014, pp. 1-7, and translation.
Chinese Office Action issued in Application No. 201180024632.6, May 20, 2014, pp. 1-10, and translation.
International Search Report issued in PCT/EP2012/061346, WO2012/172015, Aug. 1, 2012, pp. 1-9.
Written Opinion issued in PCT/EP2012/061346, WO2012/172015, Jun. 20, 2013, pp. 1-5.
International Preliminary Report on Patentability issued in PCT/EP2012/061346, WO2012/172015, Jun. 3, 1014, pp. 1-29.
Written Opinion issued in PCT/EP2013/062298, WO2013/186320, Feb. 8, 2013, pp. 1-13.
International Preliminary Report on Patentability issued in PCT/EP2012/061346, Jun. 3, 1014, pp. 1-29.
Office Action issued in Chinese Patent Application Serial No. 2011800243402, Dec. 8, 2014, pp. 1-13, translation included.
Office Action issued in European Patent Application No. 12 729 487.4-1451, Mar. 3, 2016, pp. 1-5.
Reply Filed European Patent Application No. 12 729 487.4-1451, Jul. 29, 2014, pp. 1-6.
Amended claims filed European Patent Application No. 12 729 487.4-1451, Jul. 29, 2014, pp. 1-15.
Saksena, Anil K.; Girijavallabhan, Viyyoor M.; Lovey, Raymond G.; Pike, Russell E.; Wang, Haiyan; Ganguly, Ashit K.; Morgan, Brian; Zaks, Alesey; Puar, Mohinder S., Highly stereoselective access to novel 2,2,4-trisubstituted tetrahydrofurans by halocyclization: practical chemoenzymic synthesis of SCH 51048, a broad-spectrum orally active antifungal agent, Tetrahedron Letters, 1995, 36(11), pp. 1787-1790.
Konosu, Toshiyuki; Tajima, Yawara; Miyaoka, Takeo; Oida, Sadao, Concise synthesis of optically active oxirane precursors for the preparation of triazole antifungals using the Friedel-Crafts reaction of (S)-2-tosyloxypropionyl chloride, Tetrahedron Letters, 1991, 32(51), pp. 7545-7548.
The Chemical Society of Japan, Handbook of Chemistry, Applied Chemistry 6th Ed., Maruzen, Jan. 30, 2003, p. 178.
Japanese Office Action issued Mar. 3, 2015, in Japanese Patent Application No. 2013-510614, pp. 1-6.

PROCESS FOR THE PREPARATION OF A CHIRAL COMPOUND

The present invention relates to a process for the preparation of a compound of formula (V)

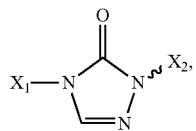

(V)

in particular Posaconazole, wherein said process comprises the steps of (1) providing a mixture comprising a compound of formula (IV)

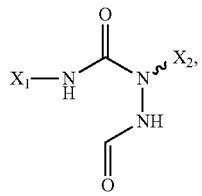

(IV)

a protic solvent system, and a suitable base; and (2) heating the mixture of (1) to obtain a mixture comprising the compound of formula (V). Further, the present invention relates to the chiral compound of formula (V) as such which is obtainable or obtained by said process, and specific mixtures and compositions containing the chiral compound of formula (V). Further, the present invention relates to the use of a protic solvent system, preferably comprising water and/or an alcohol, for the preparation of a compound of formula (V).

BACKGROUND PRIOR ART

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) is a triazole antifungal drug represented by the structure:

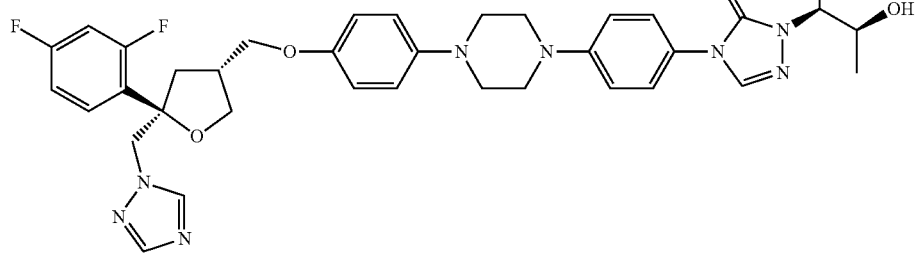

Posaconazole is used, for example, to prevent and/or treat invasive fungal infections caused by *Candida* species, *Mucor* species, *Aspergillus* species, *Fusarium* species, or *Coccidioides* species in immunocompromised patients and/or in patients where the disease is refractory to other antifungal agents such as amphothericin B, fluconazole, or itraconazole, and/or in patients who do not tolerate these antifungal agents.

Currently known processes for the preparation of Posaconazole including a cyclization reaction wherefrom the oxo-triazole according to above-shown structure results. In this respect, reference is made to WO 96/33178 A1 and WO 95/17407 A1. Said processes involve the heating of the respective starting material, namely a benzyl-protected starting material, in toluene as solvent in the presence of the strong organic base DBU (1,8-diazabicyclo[5.4.0]undec-7-ene) and a suitable molecular sieve with the exclusion of moisture. Long reaction times of at least 36 h are necessary, and a sophisticated temperature-time profile is required. Further, work-up of the obtained product is elaborate and therefore, for commercial-scale production, expensive since numerous washing steps, filtration steps, and further purification steps are needed. Among others, vacuum distillation has to be applied in order to obtain the benzyl-protected target compound. Since the benzyl protecting group has to be separated by a palladium-catalysed hydrogenation, contamination of the target compound with Pd may pose a problem.

As mentioned above, according to the prior art process, the starting material for said cyclization process is a compound in which the —OH group is benzyl-protected. Using a starting material with a non-protected —OH group is conceivable if silylation agents such as TMS (trimethylsilyl) chloride or BSA (bis-trimethylsilyl acetamide) are added which allow for an in situ protection of the —OH group and simultaneously for an activation of respective carbonyl groups in terms of the cyclization reaction. Cyclization may be further improved if TMS iodide is added. As in the prior art processes discussed above, this improved process has to be carried out with the exclusion of moisture. While the reaction times are considerably improved compared to above-mentioned prior art processes and are, for example, in the range of 16 h, and while the absence of a protecting group is certainly a major advantage over the prior art processes discussed above, there is nevertheless a need for an even more improved process which exhibits advantages with respect the specific nature of the chemical compounds used and/or the reaction parameters such as reaction times and the like. Further, taking into account the tedious purification process of the known prior art processes discussed above, there is also a need for a process which allows for a simplified work-up procedure.

SUMMARY OF THE INVENTION

Surprisingly, it was found that above-mentioned cyclization process can be significantly improved if the process is carried out in a solvent system which was hitherto completely unknown for cyclization reactions of complex molecules, in particular for the preparation of posaconazole, and in the presence of at least one suitable base.

Further, it was found that carrying out the cyclization reaction in said new solvent system also allows for a major improvement in the work-up processes, in particular as far as the crystallization process is concerned. Therefore, the use of the new solvent system not only provides an improved cyclization process but, at the same time, provides the possibility to crystallize the product compound in an unexpectedly simple manner.

In particular, it was found that the new cyclization process allows for a fast conversion of the starting material. Yet further, it was found that not only cyclization can be performed fast, but also a fast work-up of the obtained reaction mixture, in particular via crystallization, is possible. It was further found that in the course of the new process, a reaction solution can be obtained which, after completion of the cyclization reaction, remains stable over a significant period of time with regard to its impurity content which means that the impurity profile remains essentially constant over time.

Accordingly, it was found that it is possible to prepare triazolone compounds such as, in particular posaconazole, in a protic solvent system in the presence of a suitable base, in particular a suitable base having a $pK_b$ of less than 7.

A major advantage of the new process is that an unexpectedly simple solvent system can be used for the cyclization process in which solvent system, according to a preferred embodiment of the present invention, the starting material used for cyclization can be employed with its —OH group in the non-protected state.

A further major advantage of the new process is to be seen in the fact that additionally, the purification, in particular the purification by crystallization is considerably improved because, according to a still further preferred embodiment of the present invention, the desired crystalline product can be crystallized from the reaction mixture obtained from the cyclization process.

Therefore, the present invention relates to a process for the preparation of a compound of formula (V)

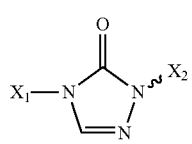
(V)

wherein $X_1$ is an optionally substituted aryl residue and $X_2$ is a linear or branched, optionally substituted alkyl residue, said process comprising (1) providing a mixture comprising a compound of formula (IV)

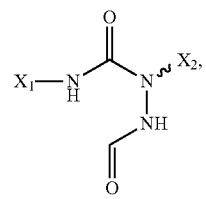
(IV)

a protic solvent system, and a suitable base;

(2) heating the mixture of (1) to obtain a mixture comprising the compound of formula (V).

Further, the present invention relates to a chiral compound of formula (V)

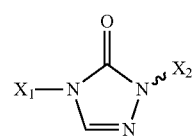
(V)

obtainable or obtained by the process according to the present invention.

Yet further, the present invention relates to a mixture comprising a compound of formula (V)

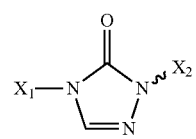
(V)

wherein $X_1$ is an optionally substituted aryl residue and $X_2$ is a linear or branched, optionally substituted alkyl residue, said mixture being directly obtained from a cyclization reaction wherein the cyclic moiety

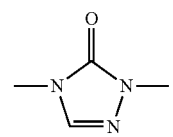

of the compound of formula (V) is formed, said directly obtained mixture comprising at least one protic solvent, preferably at least water and/or an alcohol.

Yet further, the present invention relates to a crystalline compound of formula (Vb)

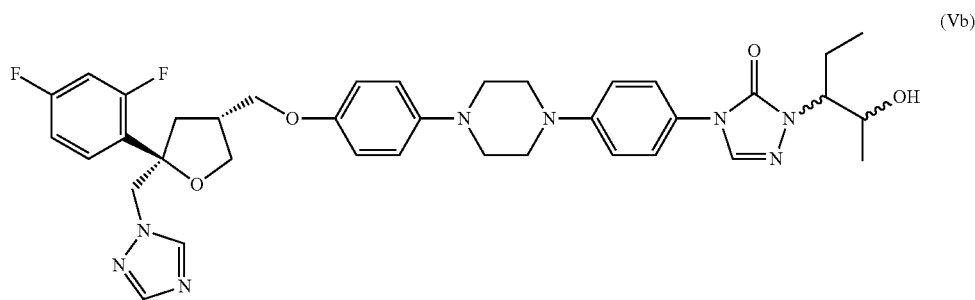 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

wherein preferably at least 95%, more preferably at least 97%, more preferably at least 99% of the molecules of said crystalline compound are present as isomer of formula (Vd)

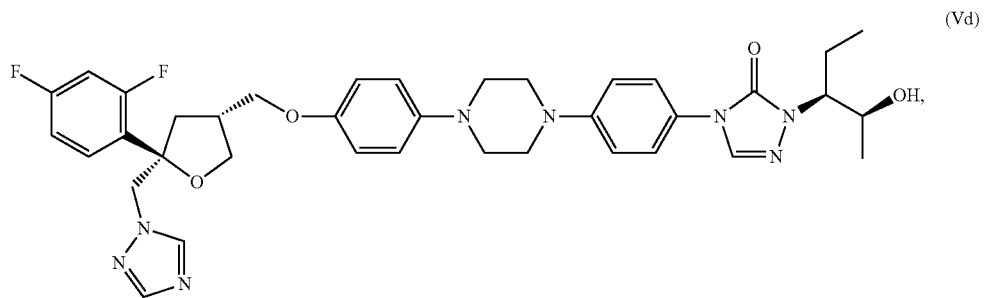 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vd)

said crystalline compound being directly obtained by a process comprising
(1) providing a mixture comprising a compound of formula (IV)

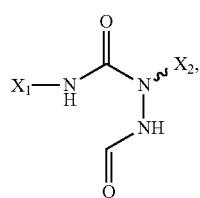

(IV)

a protic solvent system, and a suitable base;

(2) heating the mixture of (1) to obtain a mixture comprising the compound of formula (Vb);

(3) crystallizing the compound of formula (Vb) from the mixture obtained in (2);

(4) optionally separating the crystallized compound;

wherein the compound of formula (IV) is a compound of formula (IVb)

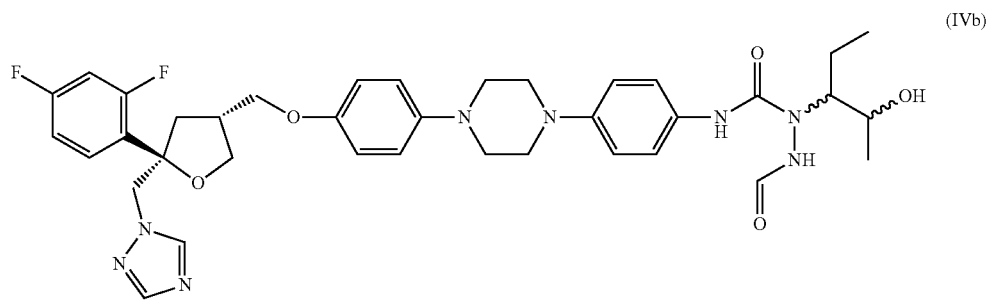 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVb)

wherein preferably at least 95%, more preferably at least 97%, more preferably at least 99% of the molecules of said compound are present as compound of formula (IVd)

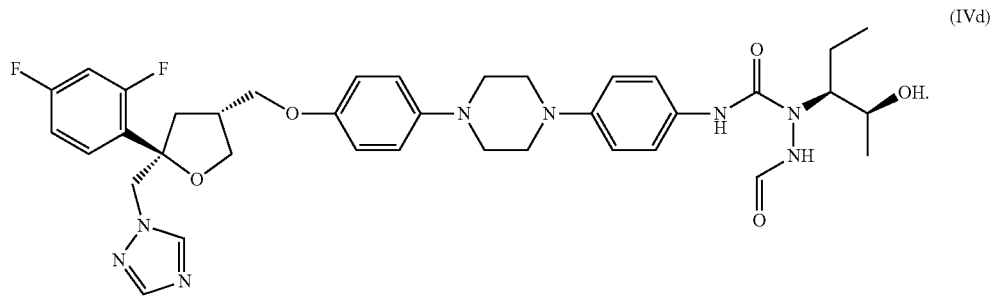 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

Yet further, the present invention relates to a composition comprising a preferably crystalline chiral compound of formula (Va)

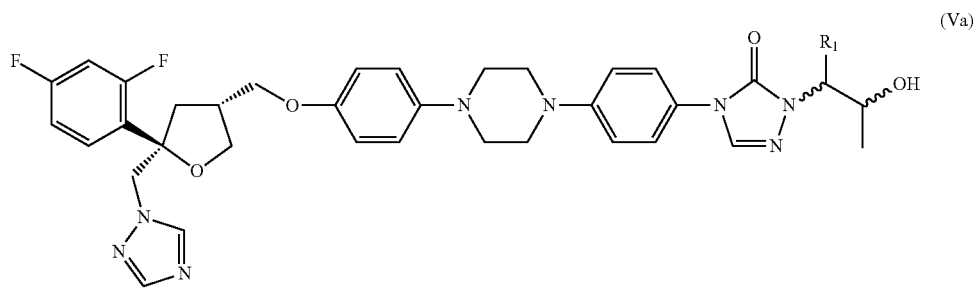
(Va)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms,
said composition preferably comprising a compound of formula (Vb)

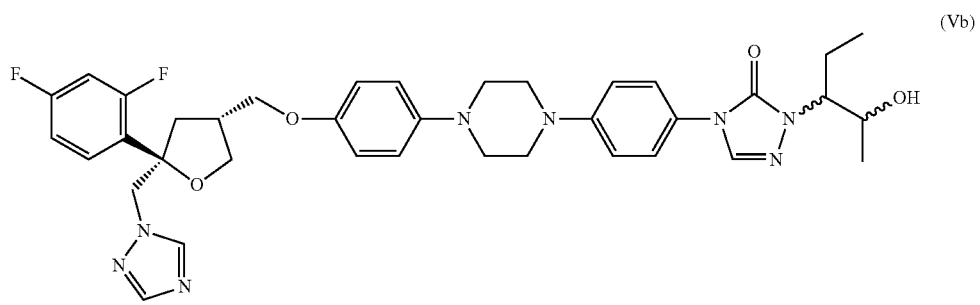 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

wherein preferably at least 95%, more preferably at least 97%, more preferably at least 99% of the molecules of said preferably crystalline compound are present as isomer of formula (Vc)

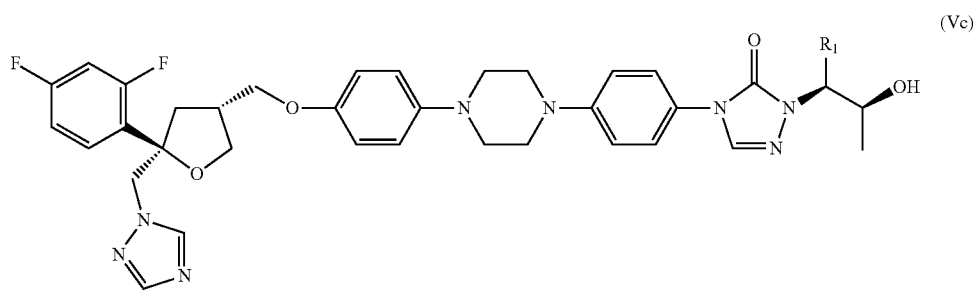
(Vc)

preferably as isomer of formula (Vd)

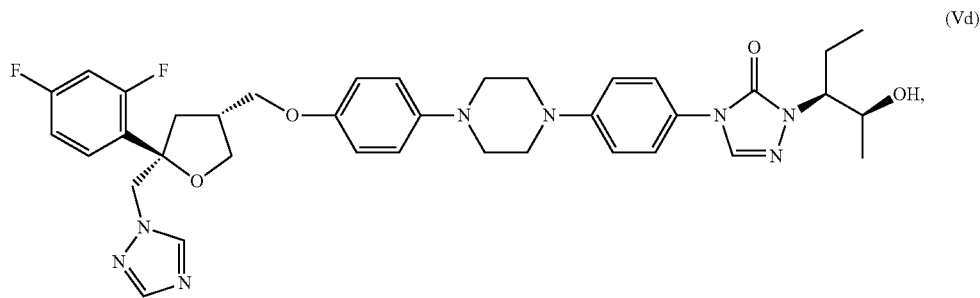 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

said composition containing at most 70 weight-ppm, preferably at most 50 weight-ppm, more preferably at most 30 weight-ppm, more preferably at most 10 weight-ppm, said composition in particular being free of a compound of formula (Ve)

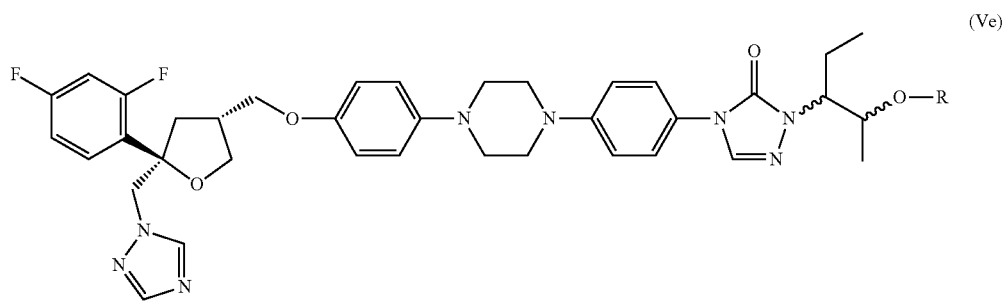

preferably a compound of formula (Vf)

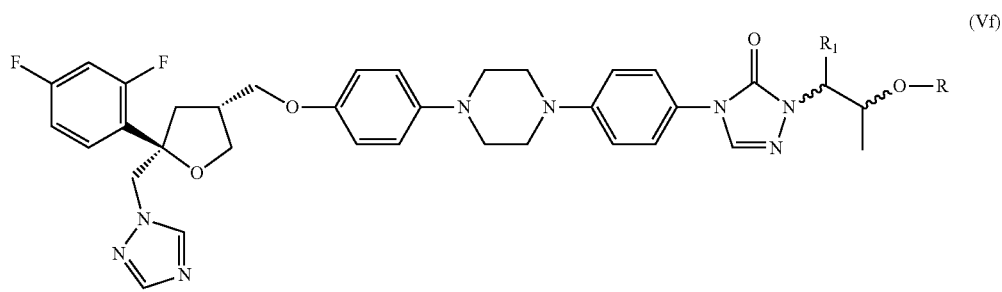

wherein —R is —CH$_2$—C$_6$H$_5$, —R preferably being selected from the group consisting of —SiR$_a$R$_b$R$_c$ and optionally substituted alkyl, aryl, alkaryl or aralkyl residues, where R$_a$, R$_b$ and R$_c$, are the same or different and selected from the group consisting of optionally suitably substituted alkyl and aryl residues, —R more preferably being a hydroxyl protecting group, and wherein said composition contains at most 0.1 area % (HPLC) of a compound of formula (IVd)

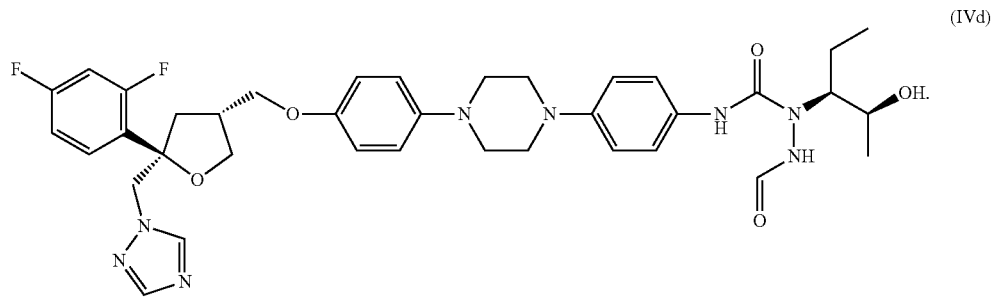 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

Yet further, the present invention relates to a pharmaceutical composition for treating fungal infections comprising an antifungally effective amount of the above-described composition and a pharmaceutically acceptable additive therefor.

Yet further, the present invention relates to the use of a protic solvent system, preferably comprising water and/or an alcohol, for the preparation of a compound of formula (V)

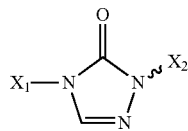

(V)

wherein $X_1$ is an optionally substituted aryl residue and $X_2$ is a linear or branched, optionally substituted alkyl residue, using a compound of formula (IV)

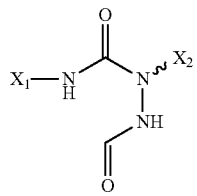

(IV)

as starting material.

Further, also suitable salts, preferably physiologically acceptable salts, solvates, preferably physiologically acceptable solvates, and esters, preferably physiologically acceptable esters, of said compounds are comprised by the present invention.

SHORT DESCRIPTION OF THE FIGURES

FIG. 1 shows the infrared spectrum (IR) of the compound of formula (IIIa) as obtained according to Reference Example 1.3 of the present invention. In FIG. 1, transmittance in % is presented on the y-axis, while wavenumber cm$^{-1}$ is presented on the x-axis. The following IR peaks can be seen in particular: 3341, 3298, 2970, 2881, 1674, 1497, 1447, 1319, 1125, 1071, 945, 910, 876, 775 and 650+/−2 cm$^{-1}$.

Figure 2:
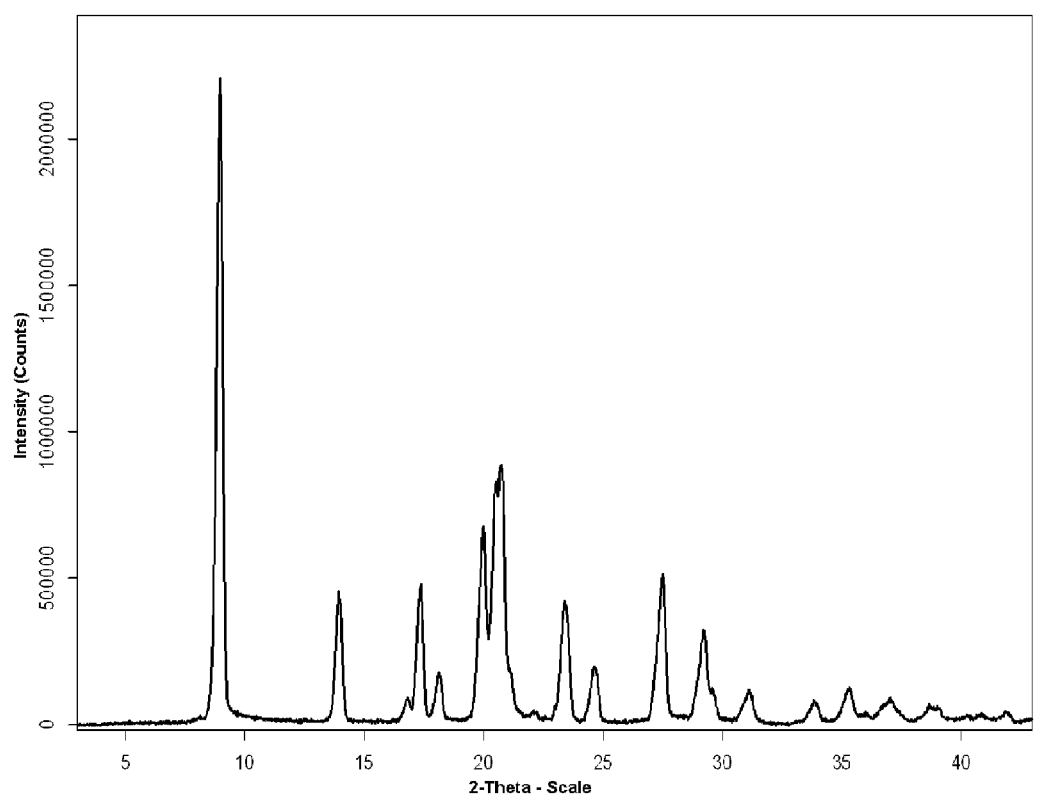

FIG. 2 shows the X-ray diffraction pattern of the compound of formula (IIIa) as obtained according to Reference Example 1.3 of the present invention. In FIG. 2, intensity—measured as counts per 300 seconds (linear scale)—is presented on the y-axis, while the position—expressed as 2 theta values in degrees—is presented on the x-axis. The following XRD peaks can be seen in particular: 9.0, 13.9, 17.4, 18.1, 20.0, 20.7, 23.4, 24.6, 27.5 and 29.2+/−0.2° 2-Theta.

Figure 3:
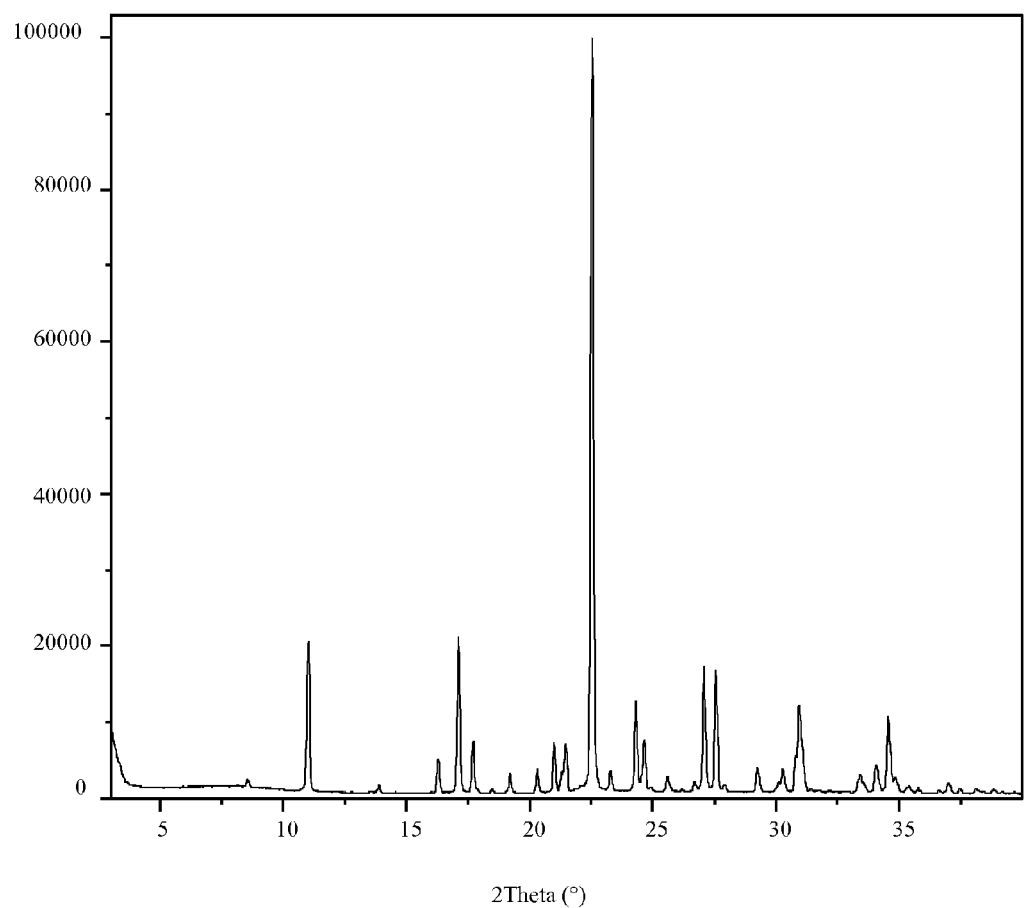

FIG. 3 shows the X-ray powder diffraction pattern (XRD) of the HCl salt of the compound of formula (GG) as obtained according to Reference Example 1.1 (Reference Example 1.1.h) of the present invention. The cis:trans ratio, i.e. the ratio compound of formula (GGa): compound of formula (GGb) is 99.2:0.8. In FIG. 3, on the x-axis, the position expressed as 2 theta values in degrees is shown, on the y-axis, the intensity, measured as counts per second (linear scale), is shown.

Figure 4:
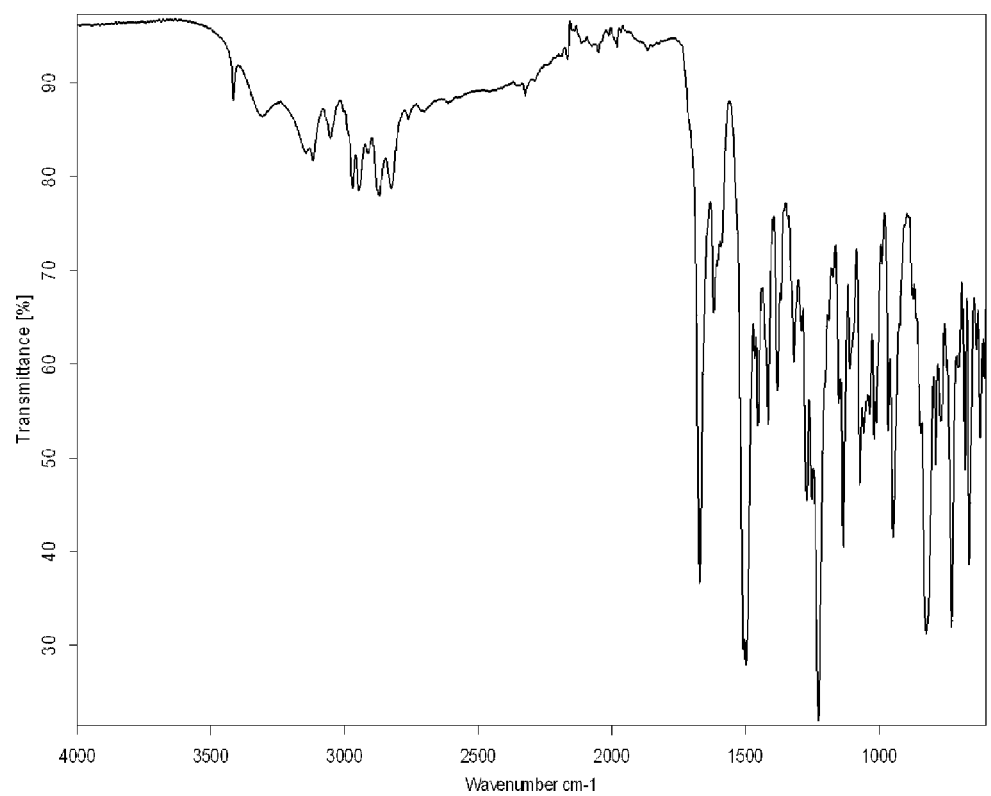

FIG. 4 shows the infrared spectrum (IR) of the compound of formula (IVb) as obtained according to Reference Example 1.4 of the present invention. In FIG. 4, transmittance in % is presented on the y-axis, while wavenumber cm$^{-1}$ is presented on the x-axis. The following IR peaks can be seen in particular: 3416, 3118, 2870, 1671, 1618, 1498, 1415, 1380, 1227, 1135, 1072, 947, 823, 728 and 663+/−2 cm$^{-1}$.

Figure 5:
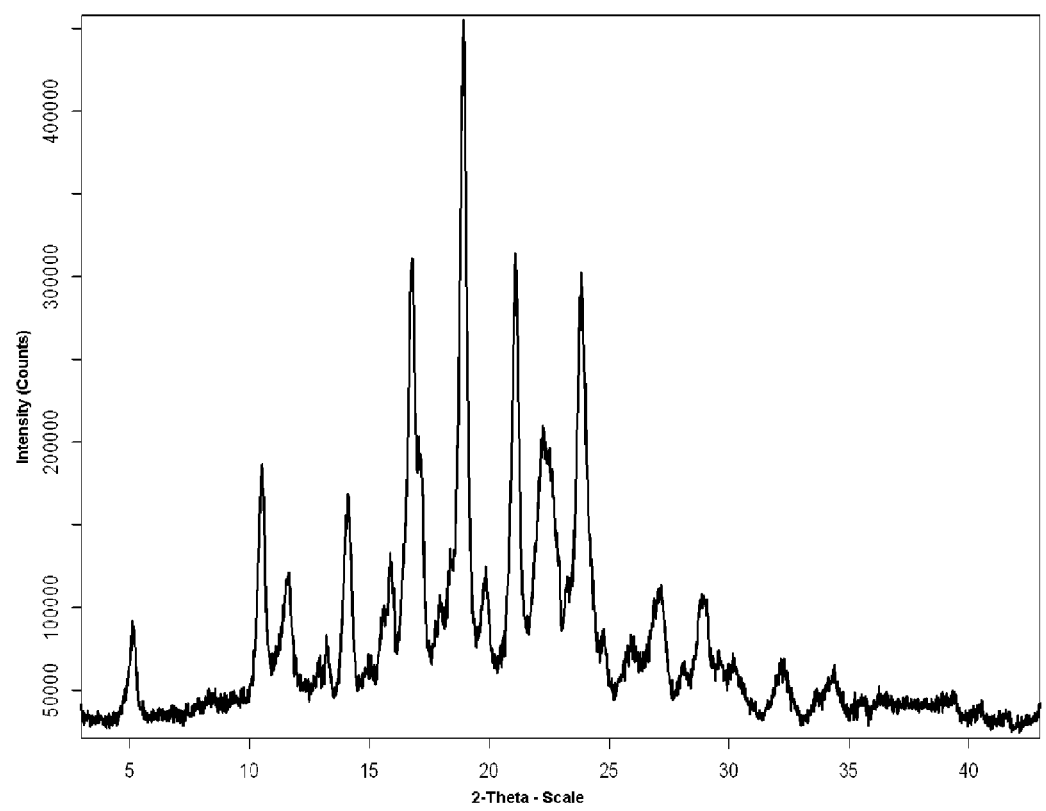

FIG. 5 shows the X-ray diffraction pattern of the compound of formula (IVb) as obtained according to Reference Example 1.4 of the present invention. In FIG. 5, intensity—measured as counts per 300 seconds (linear scale)—is presented on the y-axis, while the position—expressed as 2 theta values in degrees—is presented on the x-axis. The following XRD peaks can be seen in particular: 5.1, 10.5, 11.6, 14.1, 16.8, 18.9, 19.8, 21.1, 22.2 and 23.8+/−0.2 0° 2-Theta.

DETAILED DESCRIPTION

As mentioned above, the present invention relates to a process for the preparation of a compound of formula (V)

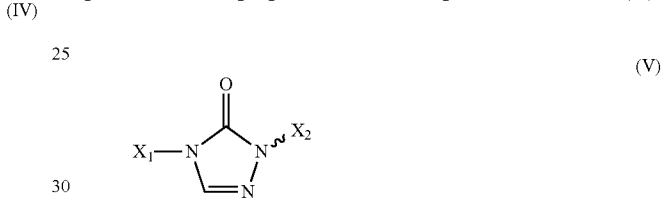

(V)

wherein $X_1$ is an optionally substituted aryl residue and $X_2$ is a linear or branched, optionally substituted alkyl residue, said process comprising
(1) providing a mixture comprising a compound of formula (IV)

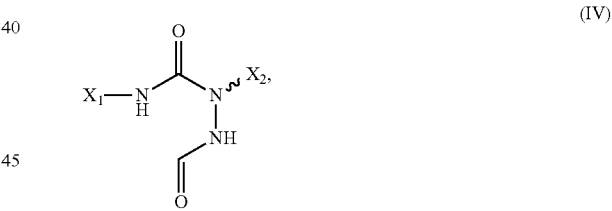

(IV)

a protic solvent system, and a suitable base;
(2) heating the mixture of (1) to obtain a mixture comprising the compound of formula (V).

Cyclization of the Compound of Formula (IV) to Obtain the Compound of Formula (V)

According to step (2) of the process of the present invention, the mixture obtained from step (1) is heated. Generally, no restrictions exist as to the temperature and the duration of heating with the proviso that a mixture comprising the compound of formula (V) is obtained. Usually, the temperature at which the mixture of (1) is heated in (2) will be suitably chosen depending on the protic solvent system used in (1) which is described in detail hereinunder.

According to preferred embodiments of the present invention, the mixture is heated to a temperature in the range of from 40 to 140° C., preferably from 50 to 120° C., more preferably from 60 to 100° C., more preferably from 70 to 85° C. Preferred temperature ranges are, for example, from 70 to 80° C. or from 75 to 85° C.

As far as the duration of heating is concerned, it is preferred to heat the mixture of (1) for at most 20 h, more preferably for at most 17 h. It is further preferred to heat the mixture of (1) for a time in the range of from 0.1 to 10 h, preferably from 1 to 8 h, more preferably from 2 to 6 h.

The term "duration of heating" as used in this context of the present invention relates to the time for which the mixture is heated at above-defined temperature. This duration does not include the time used for heating the mixture of (1) from the starting temperature of the mixture obtained in (1) to the temperature at which the mixture is kept in (2). Generally, it is not necessary in (2) to keep the mixture at one specific temperature; it is conceivable to heat the mixture obtained from (1) to a first temperature in a range as described above, keep the mixture at this first temperature for a certain period of time, and either further heat or cool the mixture to a second temperature in a range as described above. Principally, also three or more temperatures can be chosen.

Further, the process of the present invention also comprises an embodiment according to which heating is performed at least partially in the course of providing the mixture in (1). Thus, step (2) is not necessarily carried out completely subsequently after having provided the mixture in step (1). For example, it is conceivable that during mixing certain compounds in the course of step (1), the temperature of a respective mixture resulting from said mixing is increased relative to the temperature of said certain compounds.

the Protic Solvent System

According to the present invention, the mixture provided in (1) comprises a protic solvent system. The term "protic solvent system" as used in this context of the present invention relates to one single solvent or a mixture of two or more solvents. In case the protic solvent system consists of one single solvent, this solvent is a protic solvent. In case the protic solvent system consists of more than one solvent, at least one of the solvents is a protic solvent. If, for example, the protic solvent system consists of two solvents, one of these solvents or the two solvents is/are protic. If, for example, the protic solvent system consists of three solvents, one of these solvents or two of these solvents or the three solvents is/are protic. The term "protic solvent" as used in this context of the present invention relates to a solvent which contains a dissociable proton. Preferably, according to the present invention, a protic solvent is a solvent which has a hydrogen atom bound to an oxygen atom so as to form a hydroxyl group, and/or which has a hydrogen atom bound to a nitrogen atom such as in an amine group. More preferably, according to the present invention, a protic solvent is a solvent which has a hydrogen atom bound to an oxygen atom so as to form a hydroxyl group.

More preferably, the protic solvent system of (1) comprises either water, or at least one alcohol, or water and at least one alcohol. More preferably, in case the protic solvent system comprises at least one alcohol, the protic solvent system contains only one alcohol. The term "only one alcohol" as used in this context of the present invention encompasses embodiments according to which a given alcohol comprised in the protic solvent system may contain usual minor impurities with regard to other alcohols known to the skilled person.

In addition to water and/or an alcohol, the protic solvent system of the present invention may contain at least one further solvent, preferably at least one further organic solvent, which is either protic or aprotic. According to a preferred embodiment of the present invention, in case at least one such further solvent is contained in the protic solvent system, said further solvent is a ketone.

Therefore, the present invention relates to above-described process wherein the protic solvent system comprises water and/or an alcohol, and optionally at least one further organic solvent, said at least one further organic solvent preferably being a ketone.

Thus, the protic solvent system of the present invention may comprise, preferably consist of water and an alcohol, or may comprise, preferably consist of water and a further organic solvent, preferably a ketone, or may comprise, preferably consist of an alcohol and a further organic solvent, preferably a ketone. According to still further preferred embodiments of the present invention, the protic solvent system comprises water and, in addition to water, either an alcohol or a further solvent, preferably a ketone.

Hence, the present invention relates to above-described process wherein the protic solvent system comprises, preferably consists of water and an alcohol, or comprises, preferably consists of water and a ketone.

As mentioned above, it is conceivable that the protic solvent system consists of only one solvent. This solvent is, for example, water. For protic solvent systems which comprise water and, in addition to water, at least one further component such as an alcohol and/or a further organic solvent such as a ketone, the content of the protic solvent system with respect to water is less than 100 vol-% (volume-%) such as, for example, in the range of up to 75 vol-% or in the range of up to 50 vol-% or in the range of up to 25 vol-%. Preferably, the protic solvent system according to the present invention contains not more than 25 vol-% water.

Therefore, the present invention relates to above-described process wherein the protic solvent system comprises water wherein the water content of the protic solvent system is at most 25 vol-% based on the total volume of the protic solvent system.

As far as the alcohol is concerned, there are no specific restrictions with the proviso that in combination with water and/or in combination with the further solvent, it acts as solvent for the compound of formula (IV) and allows for obtaining the compound of formula (V) in (2). Preferably, an alcohol of a protic solvent system of the present invention contains 1, 2, 3, 4 or 5 carbon atom(s). More preferably, the alcohol is selected from the group consisting of methanol, ethanol, isopropanol, and n-butanol. Most preferably, the alcohol is isopropanol.

As far as the further solvent, preferably the ketone is concerned, there are no specific restrictions with the proviso that in combination with water and/or in combination with the alcohol, it acts as solvent for the compound of formula (IV) and allows for obtaining the compound of formula (V) in (2). Conceivable solvents other than a ketone may include dichloromethane (DCM), tetrahydrofuran (THF), methyl tetrahydrofuran, isopropylacetate, acetonitrile or the like. Preferably, the preferred further solvent, namely the ketone, contains 3, 4, 5, 6, 7, 8 or 9 carbon atoms, more preferably 3, 4, 5 or 6 carbon atoms. More preferably, the ketone is selected from the group consisting of acetone or methylisobutyl ketone (MIBK).

Therefore, the present invention relates to above-described process wherein the alcohol comprises from 1 to 5 carbon atoms and is preferably selected from the group consisting of methanol, ethanol, isopropanol, and n-butanol, and wherein the ketone comprises 3 to 9 carbon atoms and is preferably selected from the group consisting of acetone and methylisobutyl ketone (MIBK).

Protic solvents according to the present invention include, but are not restricted to, water, or methanol, or ethanol, or isopropanol, or n-butanol, or a mixture of water and methanol, or a mixture of water and ethanol, or a mixture of water and isopropanol, or a mixture of water and n-butanol, or a mixture of water and acetone, or a mixture of water and MIBK. Also conceivable are mixtures of at least one of methanol, ethanol, isopropanol, and n-butanol with acetone and/or MIBK.

Most preferably, as far as its components are concerned, the protic solvent system consists of water and isopropanol. Generally, the volume ratio of water relative to isopropanol is in the range of from 1:12 to 3:1, more preferably from 1:5 to 1:1. As described above, in even more preferred protic solvent systems of the present invention, the water content is at most 25 vol-%. Therefore, most preferably, the volume ratio of water relative to isopropanol is at most 1:3, in particular in the range of from 1:3 to 1:4.

Therefore, the present invention also relates to above-described process wherein the protic solvent system is a mixture of water and isopropanol, wherein the volume ratio of water relative to isopropanol is in the range of from 1:12 to 3:1, preferably from 1:5 to 1:1, more preferably from 1:4 to 1:3.

Generally, the present invention also relates to the use of a protic solvent system, preferably comprising water and/or an alcohol, for the preparation of a compound of formula (V)

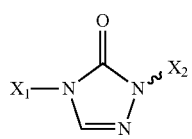

(V)

wherein $X_1$ is an optionally substituted aryl residue and $X_2$ is a linear or branched, optionally substituted alkyl residue, using a compound of formula (IV)

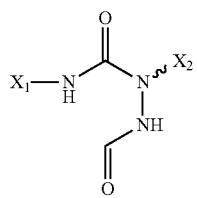

(IV)

as starting material.

The Suitable Base

As far as the suitable base employed in (1) is concerned, there are no specific restrictions with the proviso that it allows for obtaining the compound of formula (V) in (2). Generally, also two or more suitable basic compounds can be employed. At least one inorganic, or at least one organic base, or at least one inorganic and at least one organic base can be employed. Preferably, only one suitable basic compound is employed. Preferably, the suitable base has a $pK_b$ of less than 7, more preferably at most 3, more preferably at most 0.

Generally, it is conceivable that at least one component of the protic solvent system mentioned above may act as suitable base. As far as such embodiments are concerned, the term "providing a mixture comprising a protic solvent system and a suitable base" as used in the context of the present invention relates to a process wherein the suitable base is not a compound which is distinct from the components of the protic solvent system. If, for example, two or more suitable bases are employed, it is conceivable that at least one base is a protic solvent and at least one base is not a protic solvent. According to a conceivable embodiment, a compound which may act as protic solvent and, simultaneously, as base is ammonia or an amine such as, for example, triethylamine (TEA).

According to preferred embodiments of the present invention, at least one base is employed which is not a protic solvent and which is not a component of the protic solvent system. As far as above-mentioned inorganic bases are concerned, hydroxides and carbonates are preferred. As far as above-mentioned organic bases are concerned, alcoholates are preferred.

Therefore, the present invention relates to above-described process wherein the suitable base is at least one hydroxide, or at least one carbonate, or at least one alcoholate, or a mixture of at least one hydroxide and at least one carbonate, or a mixture of at least one hydroxide and at least one alcoholate, or a mixture of at least one carbonate and at least one alcoholate, or a mixture of at least one hydroxide and at least one carbonate and at least one alcoholate.

As to the cations of the hydroxides, carbonates, and alcoholates mentioned above are concerned, no specific restrictions exist with the proviso that according to (2), the compound of formula (V) is obtained. For example, alkali metals and earth alkaline metals can be mentioned as suitable cations, with alkali metals being preferred. Among the alkali metals, sodium, potassium, and lithium, are especially preferred.

Therefore, the present invention relates to above-described process wherein the hydroxide is selected from the group consisting of an alkali metal hydroxide and an alkaline earth metal hydroxide, preferably an alkali metal hydroxide, more preferably sodium hydroxide, potassium hydroxide, lithium hydroxide; wherein the carbonate is selected from the group consisting of an alkali metal carbonate and an alkaline earth metal carbonate, preferably an alkali metal carbonate, more preferably sodium carbonate, potassium carbonate; wherein the alcoholate is selected from the group consisting of an alkali metal alcoholate and an alkaline earth metal alcoholate, preferably an alkali metal alcoholate, more preferably sodium alcoholate, potassium alcoholate, lithium alcoholate.

Concerning the alcoholate, compounds are preferred having 1, 2, 3, 4, or 5 carbon atoms, more preferably 1, 2, 3, or 4 carbon atoms. Even more preferably, the alcoholate is selected from the group consisting of a methanolate, an ethano late, an isopropanolate, and an n-butano late.

Generally, an inorganic base is preferably employed in the process of the present invention, with above-mentioned hydroxides being especially preferred. According to a particularly preferred embodiment of the present invention, the suitable base is sodium hydroxide.

Therefore, the present invention relates to above-described process wherein the protic solvent system comprises, preferably consists of water and an alcohol, and wherein the suitable base is an inorganic base. More preferably, the protic solvent system comprises, preferably consists of water and an alcohol having 1, 2, 3, 4 or 5 carbon atoms, and the inorganic base is a hydroxide. Even more preferably, the protic solvent system comprises, preferably consists of water and an alcohol selected from the group consisting of methanol, ethanol, isopropanol, and n-butanol, and the inorganic base is an alkali metal hydroxide. According to one especially preferred embodiment of the present invention, the protic solvent system consists of water and iso-propanol and the suitable base is sodium hydroxide which protic solvent system, even more preferably, has a water content of at most 25 vol-%.

As far as the content of the mixture provided in (1) with regard to the suitable base is concerned, no specific restrictions exist with the proviso that in (2), the compound of formula (V) is obtained. Preferably, in the mixture provided in (1), the molar ratio of base relative to the compound of formula (IV) is in the range of from 0.1:1 to 3:1, preferably from 0.4:1 to 2.5:1, more preferably from 0.6:1 to 2:1. Especially preferred ranges are 0.75:1 to 1.5:1, more preferably from 0.85:1 to 1.25:1, more preferably from 0.95:1 to 1.05:1.

Therefore, the present invention relates to above-described process wherein in the mixture provided in (1), the molar ratio of the suitable base relative to the compound of formula (IV) is in the range of from 0.1:1 to 3:1, preferably from 0.75:1 to 1.5:1, more preferably from 0.95:1 to 1.05:1.

The pH of the mixture provided in (1), as determined using a pH-sensitive glass electrode, is preferably at least 10, more preferably at least 11, more preferably in the range of from 12 to 14.

As described above, the mixture provided in (1) comprises the compound of formula (IV), the protic solvent system and the suitable base. Preferably, the mixture provided in (1) consists of the compound of formula (IV), the protic solvent system and the suitable base. The term "protic solvent system" as used in this context of the present invention includes usual impurities contained in the individual components of the protic solvent system. The term "suitable base" as used in this context of the present invention includes usual impurities contained in the individual components of the suitable base. The term "compound of formula (IV)" as used in this context of the present invention includes usual impurities and/or components contained in the specific chemical form in which the compound of formula (IV) is employed. If, for example, the compound of formula (IV) is employed as essentially pure crystalline compound, the term "compound of formula (IV)" includes impurities contained in the crystalline compound resulting from the crystallization process. If, for example, the compound of formula (IV) is employed as crystalline compound in the form of a crystalline adduct as herein described in detail, the term "compound of formula (IV)" includes the impurities contained in the crystalline compound resulting from the crystallization process and, additionally, the other components of the crystalline adduct. In case such crystalline adduct is, for example, a crystalline adduct according to
  compound of formula (IV):imidazole:DCM
as obtained from step (0.5) as herein described in detail, the term "compound of formula (IV)" includes, apart from the compound of formula (IV), also the other components of the adduct, namely imidazole and dichloromethane (DCM). As to such adducts, the compound of formula (IV) most preferably is a compound of formula (IVd).

In the section "Background prior art" hereinabove, it is described that according to a conceivable method, cyclization of the compound of formula (IV), in particular containing the —OH group in its non-protected form, may be performed using silylation agents such as TMS (trimethylsilyl) chloride or BSA (bis-trimethylsilyl acetamide) which are added to allow for an in situ protection of the —OH group and simultaneously for an activation of respective carbonyl groups in terms of the cyclization reaction. Compared to this method which in itself is a considerable improvement of the known prior art processes since the finally obtained compound of formula (V) cannot contain any impurities with protected —OH group, it is a major advantage of the process of the present invention that no silylation agents are necessary. According to the present invention, it was found that no silylation agents have to be used which in turn allows for the use of a protic solvent system which, in particular for industrial-scale production of compounds of formula (V), are much easier to handle than the strictly protic solvent-free solvent system necessary for the use of silylation agents.

Therefore, the present invention also relates to above-described process, wherein step (2) of heating the mixture of (1) is carried out in the absence of bis-trimethylsilyl acetamide (BSA) and a trimethylsilyl (TMS) halide, preferably trimethylsilyl iodide (TMSI) and/or trimethylsilyl chloride (TMSCl), more preferably a trialkylsilyl halide, preferably in the absence of a silylating agent.

According to a conceivable embodiment of the present invention, a compound can be employed which, on the one hand, forms the protic solvent system and, on the other and, is the suitable base. As an example of such compound, diisopropylamine may be mentioned. Generally, one or more of such compounds can be employed, either alone or in combination with at least one further protic solvent and/or with at least one suitable base.

As mentioned above, essentially complete conversion can be achieved by the process according to the present invention after a comparatively short period of time, i.e. conversion of the compound of formula (IV) via cyclization can be performed fast. While in certain embodiments, longer periods of reaction time can be chosen, typical short periods of times are in the range of about 6 hours at most, such as up to 2 hours, or up to 3 hours, or up to 6 hours.

The Starting Material, the Compound of Formula (IV)

According to step (1) of the process of the present invention, a mixture comprising the compound of formula (IV)

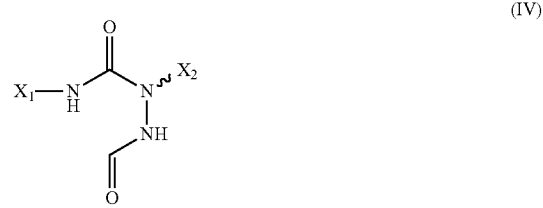

is provided wherein $X_1$ is an optionally substituted aryl residue and $X_2$ is a linear or branched, optionally substituted alkyl residue.

Residue $X_2$

Generally, as to the specific chemical nature of residue $X_2$ of the compound (IV), no restrictions exist with the proviso that starting from the mixture provided in (1), the compound of formula (V) is obtained according to (2).

According to a preferred embodiment of the present invention, $X_2$ is a branched alkyl residue, more preferably a branched alkyl residue. Preferably, said branched alkyl residue is suitably substituted with at least one suitable substituent which is not an alkyl residue, preferably with exactly one suitable substitutent which is not an alkyl residue. As to such suitable substitutent, generally no restrictions exist with the proviso that starting from the mixture provided in (1), the compound of formula (V) is obtained according to (2). Preferably, a suitable substituent is an optionally suitably protected hydroxyl group.

According to a more preferred embodiment, $X_2$ is a residue according to formula (X2)

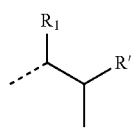
(X2)

wherein the dotted line in formula (X2) stands for the bond between $X_2$ and the N atom in formulas (IV) and (V).

In (X2), residue $R_1$ is preferably H or a straight or branched alkyl residue which preferably has from 1 to 6 carbon atoms, namely 1, 2, 3, 4, 5, or 6 carbon atoms, more preferably from 1 to 4 carbon atoms, namely 1, 2, 3, or 4 carbon atoms, more preferably 1 or 2 carbon atoms, in particular 2 carbon atoms.

Further in (X2), residue R' is preferably either H or an optionally substituted alkyl, aryl, aralkyl, or alkaryl residue, preferably having from 1 to 10, more preferably from 1 to 8 carbon atoms, or a suitable functional group which functional group is optionally suitably protected. In case residue R' is an optionally substituted alkyl, aryl, aralkyl, or alkaryl residue, an alkyl residue having from 1 to 6, preferably from 1 to 4 carbon atoms is preferred. More preferably, residue R' is either a hydroxyl group —OH or a suitably protected hydroxyl group. Therefore, according to a preferred embodiment, residue R' is —O—R wherein —R is —H or a suitable hydroxyl protecting group. As to such suitable hydroxyl protecting group, generally no specific restrictions exist with the proviso that starting from the mixture provided in (1), the compound of formula (V) is obtained according to (2). Preferably, the suitable hydroxyl protecting group is benzyl or a group —$SiR_aR_bR_c$ wherein the residues $R_a$, $R_b$ and $R_c$ may be the same or different and are preferably alkyl or aryl residues. The term "aryl residue" as used in this context of the present invention relates to a carbocyclic aromatic group, such as phenyl or naphthyl or the like. The term "alkyl residue" as used in the context of the present invention relates to straight or branched alkyl moieties which preferably have 1, 2, 3, 4, 5, or 6 carbon atoms, more preferably 1, 2 or 3 carbon atoms, more preferably 1 carbon atom. Especially preferably, the residue —R is —H or a hydroxyl protecting group selected from the group consisting of —$Si(CH_3)_3$ and benzyl, —R most preferably being —H.

Therefore, the present invention relates to above-described process wherein $R_1$ is H or an alkyl residue preferably having from 1 to 6 carbon atoms, and wherein —R' is selected from the group consisting of —H, -alkyl, and —O—R wherein —R is —H or a suitable hydroxyl protecting group preferably selected from the group consisting of —$SiR_aR_bR_c$ and optionally substituted alkyl, aryl, alkaryl or aralkyl residues where $R_a$, $R_b$ and $R_c$ are the same or different and selected from the group consisting of optionally substituted alkyl and aryl residues.

More preferably, the present invention relates to above-described process wherein $R_1$ is an alkyl residue having from 1 to 4 carbon atoms, preferably 1 or 2 carbon atoms, most preferably 2 carbon atoms, in particular ethyl, and wherein —R' is —O—R wherein —R is —H or a hydroxyl protecting group selected from the group consisting of —$Si(CH_3)_3$ and benzyl, preferably —H.

Residue $X_1$

Generally, as to the specific chemical nature of residue $X_1$ of the compound (IV), no restrictions exist with the proviso that starting from the mixture provided in (1), the compound of formula (V) is obtained according to (2). Generally, $X_1$ is an optionally substituted aryl residue.

The term "optionally substituted aryl residue" as used in this context of the present invention refers to aryl residues which have, for example, up to 6 or up to 12 carbon atoms. If such aryl residue is a substituted aryl residue, the number of carbon atoms refers to the number of carbon atoms of the corresponding unsubstituted aryl residue. According to preferred embodiments of the present invention, optionally substituted aryl residues are chosen so as to allow for the preparation of the compound of formula (V), in particular for the preparation of compounds which may be used as antifungal agent. More preferably, $X_1$ is a suitably substituted aryl residue, more preferably a suitably substituted phenyl residue.

Preferably, $X_1$ is a residue according to formula (X1)

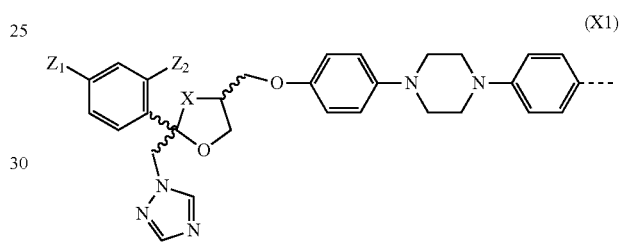
(X1)

wherein $Z_1$ and $Z_2$ are suitably substituents of the shown benzene ring and X is a suitable heteroatom or another suitable chemical moiety wherein $Z_1$ and $Z_2$ and X are preferably chosen to allow for the preparation of a compound (V) which may be used as antifungal agent. Preferably, $Z_1$ and $Z_2$ are independently halogen, more preferably F or Cl, more preferably F, wherein —X— is a heteroatom, preferably —O—, or an alkyl moiety, preferably —$CH_2$—, with —X—, more preferably being —$CH_2$—.

Therefore, the present invention also relates to above-described process, wherein $X_1$ is a residue according to formula (X1)

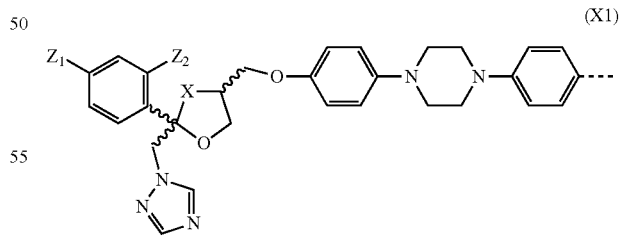
(X1)

wherein $Z_1$ and $Z_2$ are independently F or Cl, preferably F, wherein —X— is —O— or —$CH_2$—, preferably —$CH_2$—, and wherein the dotted line in formula (X1) stands for the bond between $X_1$ and the NH group in formula (IV) and the bond between $X_1$ and the N atom in formula (V).

More preferably, $X_1$ is a residue according to formula ($X1_{cis}$)

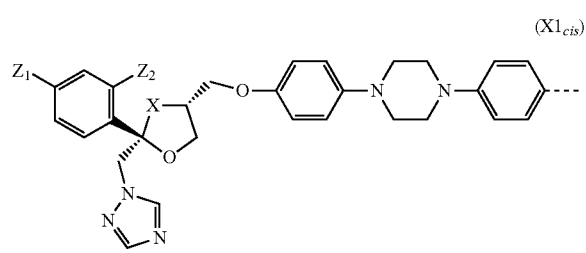

wherein $Z_1$ and $Z_2$ are independently F or Cl, preferably F, wherein —X— is —O— or —CH$_2$—, preferably —CH$_2$—, and wherein the dotted line in formula (X1$_{cis}$) stands for the bond between $X_1$ and the NH group in formula (IV) and the bond between $X_1$ and the N atom in formula (V).

Therefore, according to an even more preferred embodiment of the present invention, the starting material for the inventive cyclization process, namely the compound of formula (IV), has the following structure:

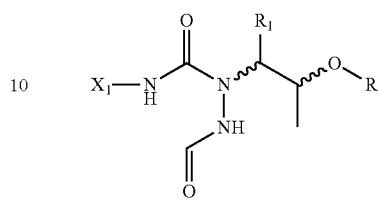

preferably

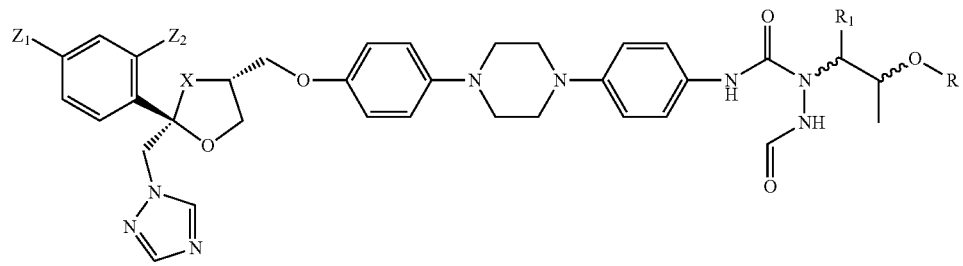

more preferably

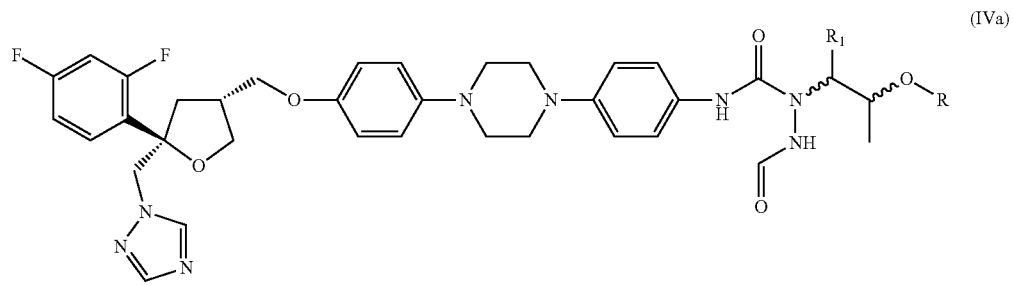

more preferably

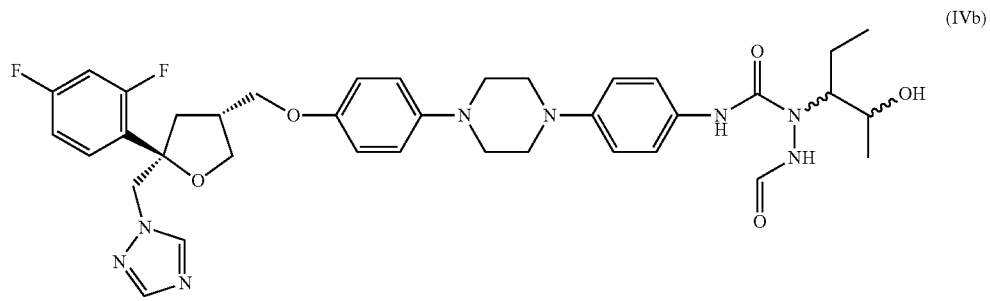 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

more preferably

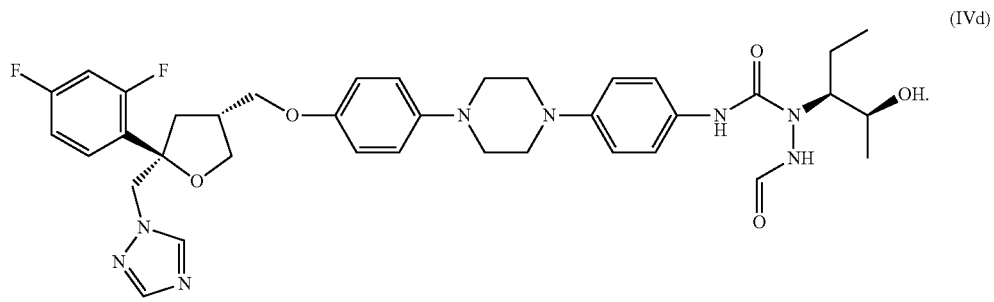 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

Preparation of the Starting Material, the Compound of Formula (IV)

Generally, there are no restrictions how the compound of formula (IV) is prepared. In particular in the case where the residue $X_2$ has the preferred structure

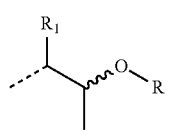

as defined above, the compound of formula (IV) can be prepared according to a process comprising (0.1) providing a compound of formula (I)

$$X_1-NH_2 \qquad (I)$$

or a salt thereof, wherein the residue $X_1$ is an optionally suitably substituted aryl residue;

(0.2) providing a compound of formula (IIa)

$$O=C=N-Y_0 \qquad (IIa)$$

wherein $Y_0$ is an optionally substituted alkyl or aryl residue;

or, preferably, phosgene or a phosgene derivative of formula (IIb)

wherein $Y_1N-$ and $Y_2N-$ are the same or different optionally substituted nitrogen heterocycle moieties, preferably selected from the group consisting of imidazolyl and benzimidazolyl, more preferably imidazolyl, the preferred compound of formula (IIb) being carbonyldiimidazole (CDI);

(0.3) providing a compound of formula (III)

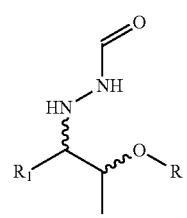

or a salt thereof, (0.4) mixing and reacting the compounds of formulas (I), (IIa) and/or (IIb), and (III) in a solvent, preferably dichloromethane (DCM) in any order to obtain a reaction mixture containing the compound of formula (IV')

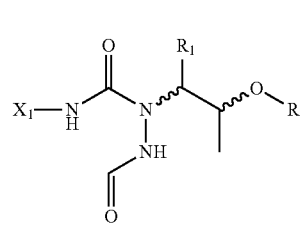

Step (0.1)—Providing the Compound of Formula (I)

As indicated above in the context of residue $X_1$, the compound of formula (I) is most preferably a chiral compound of formula

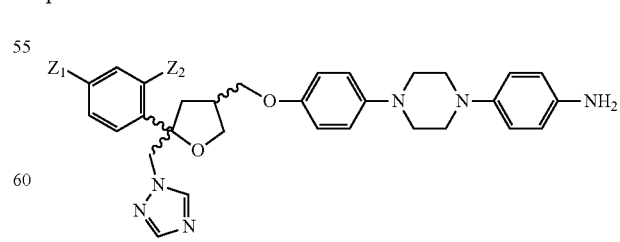

wherein $Z_1$ and $Z_2$ are independently F or Cl, preferably F. Even more preferably, the compound of formula (I) is a compound of formula

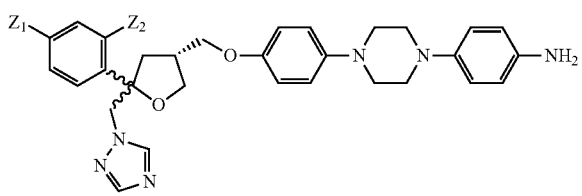

wherein $Z_1$ and $Z_2$ are independently F or Cl, preferably F, and wherein, according to an even more preferred embodiment, at least 95%, more preferably at least 97%, more preferably at least 99% of the molecules of said compound are present as isomer of formula

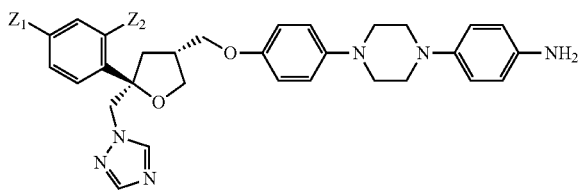

Therefore, according to a preferred embodiment of the present invention, the compound of formula (I) is a compound of formula

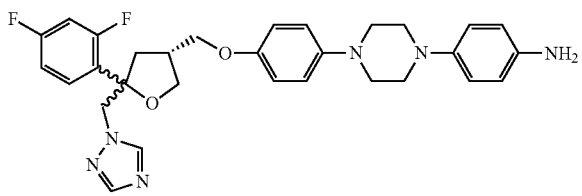

wherein at least at least 95%, more preferably at least 97%, more preferably at least 99% of the molecules of said compound are present as isomer of formula (Ia)

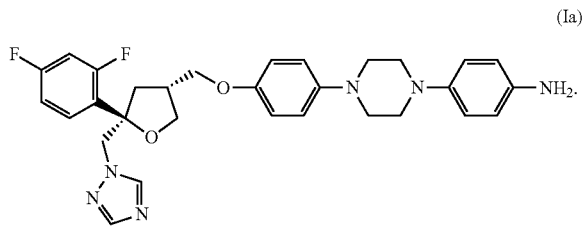 [SMILES: Nc1ccc(N2CCN(c3ccc(OC[C@@H]4CO[C@@](Cn5cncn5)(c5ccc(F)cc5F)C4)cc3)CC2)cc1]

Thus, the present invention in particular relates to above-defined process wherein the compound of formula (I) is the compound of formula (Ia).

As far as the preparation of the compound of formula (Ia) is concerned, no particular restrictions exist. Preferably, the compound of formula (Ia) is prepared by reacting a compound of formula (A)

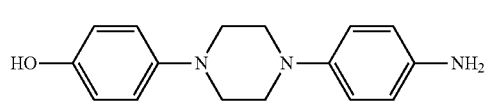

with a compound of formula (B)

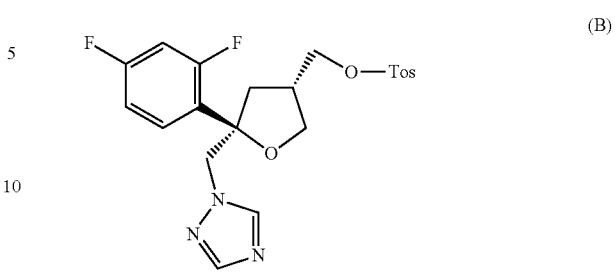

As far as providing the compound of formula (A) is concerned, no particular restrictions exist. A conceivable process for the preparation of the compound of formula (A) is disclosed, for example, in M. Hepperle et al., *Tetrahedron Lett.* 2002, 43, 3359-3363, in U.S. Pat. No. 6,355,801 B1, or in EP 1 230 231 B1.

As far as providing the compound of formula (B) is concerned, no particular restrictions exist. A conceivable process for the preparation of the compound of formula (B) is disclosed, for example, in U.S. Pat. No. 5,403,937, EP 0 736 030 A1, or in WO 95/17407.

According to a preferred embodiment of the present invention, the compound of formula (B) is provided by a process wherein the HCl salt of the compound of formula (GGa)

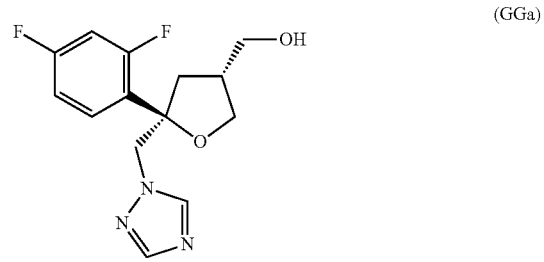 [SMILES: OC[C@@H]1CO[C@@](Cn2cncn2)(c2ccc(F)cc2F)C1]

is transformed into the compound of formula (B).

As far as converting the HCl salt of the compound of formula (GGa) to the respective tosylate according to formula (B) is concerned, no particular restrictions exist. According to a preferred embodiment of the present invention, the at least partially crystalline, preferably crystalline salt of the compound of formula (GG)

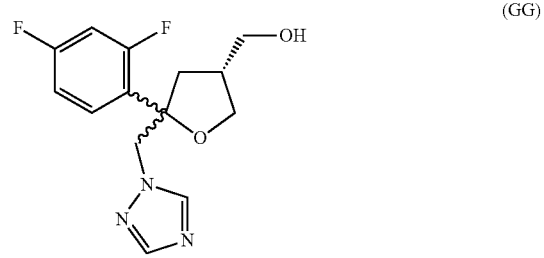

is provided suspended in a suitable liquid, most preferably dichloromethane (DCM). To this suspension, preferably at least one suitable organic nitrogen base such as triethylamine (TEA) and/or 4-dimethylaminopyridine (DMAP) is/are added. To the resulting mixture, a suitable p-toluenesulfonyl containing compound such as p-toluenesulfonyl chloride (TsCl) is added at a preferred temperature of from 10 to 40° C. and preferably reacted for 1 to 6 hours. The obtained reaction mixture containing the compound of formula (B) is preferably suitably extracted, and from the obtained organic layer, optionally after suitable concentration, the compound of formula (B) is obtained as solid, e.g. by crystallization, which solid may be optionally suitably dried and preferably subsequently, without any further intermediate treatment, employed as starting material for the reaction with the compound of formula (A). Applying crystallization for obtaining the compound of formula (B) advantageously allows for purification of said compound as well as for a straightforward scale up of the herein described processes using said compound to a large scale production.

As far as the preparation of the HCl salt of the compound of formula (GGa) is concerned, no particular restrictions exist. According to a preferred embodiment of the present invention this HCl salt is prepared according to a process from which the HCl salt of the compound of formula (GG) is obtained, said compound of formula (GG) containing the cis-isomer of formula (GGa) and the trans-isomer of formula (GGb)

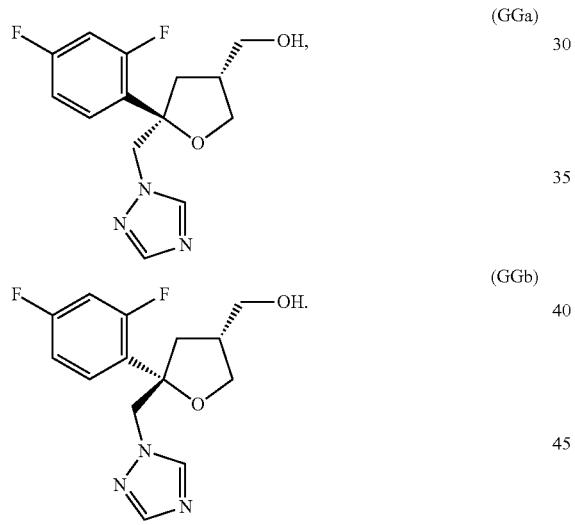

According to a preferred embodiment of the present invention, said preferably crystalline HCl salt contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

According to an even more preferred embodiment of the present invention, said HCl salt of the compound of formula (GG) is obtained by a process comprising
(I) providing the compound of formula (GG) comprised in a first suitable solvent;
(II) treating the compound of formula (GG) comprised in the first suitable solvent with HCl comprised in a second suitable solvent to obtain the HCl salt of compound of formula (GG).

In particular, the process of providing the HCl salt of the compound of formula (GG) according to a preferred embodiment of the present invention comprises steps according to the following embodiments and the respective combinations thereof, as indicated:

1. A process for the preparation of a hydrogen chloride (HCl) salt of a compound of formula (GG)

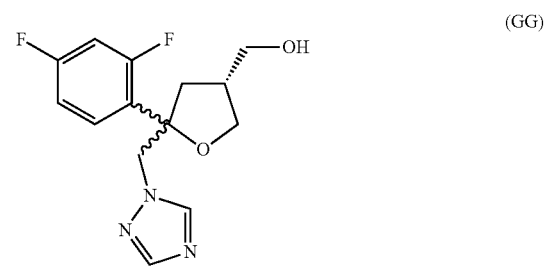

said compound of formula (GG) containing the cis-isomer of formula (GGa) and the trans-isomer of formula (GGb)

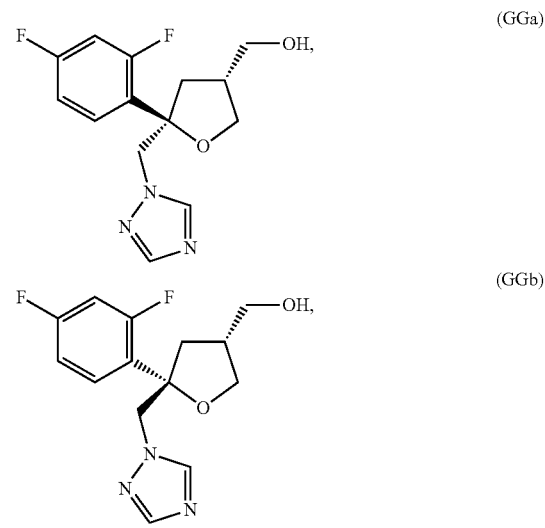

the process comprising
(I) providing the compound of formula (GG) comprised in a first suitable solvent;
(II) treating the compound of formula (GG) comprised in the first suitable solvent with HCl comprised in a second suitable solvent to obtain the HCl salt of the compound of formula (GG).

2. The process of embodiment 1, wherein the compound of formula (GG) provided in (I) contains from 80 to 95%, preferably from 85 to 95% of the cis-isomer of formula (GGa) and from 20 to 5%, preferably from 15 to 5% of the trans-isomer of formula (GGb).

3. The process of embodiment 1 or 2, wherein in (I), the compound of formula (GG) is provided by a method comprising (i.1) reacting a compound of formula (AA)

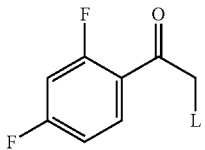
(AA)

wherein L is a leaving group, preferably a halogen, more preferably Cl, in a solvent with a nucleophilic compound comprising a nucleophilic residue $R_{aaa}R_{bbb}R_{ccc}Si-CH_2$ wherein $R_{aaa}$, $R_{bbb}$ and $R_{ccc}$ are the same or different and selected from the group consisting of optionally suitably substituted alkyl and aryl residues, to obtain a reaction mixture containing as intermediate a beta-hydroxy silane of formula

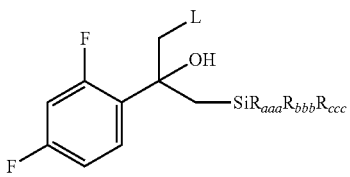

said reacting preferably being performed at a temperature in the range of from −50 to +20° C., more preferably from −30 to +10° C., more preferably from −15 to +5° C.;

(i.2) treating the resulting reaction mixture, preferably without change of solvent, with a reagent promoting elimination reaction to obtain a reaction mixture containing a compound of formula (BB)

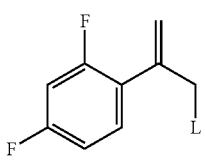
(BB)

wherein treating is performed at a temperature in the range of from −20 to +70° C. and wherein said reagent is preferably an acid, preferably an inorganic acid, more preferably sulfuric acid, wherein, if sulfuric acid is used, the temperature at which said treating is performed is preferably in the range of from 40 to 50° C.;

(ii) reacting the compound of formula (BB) with a malonic ester $R_{11}OOC-CH_2-COOR_{22}$ to obtain a compound of formula (CC)

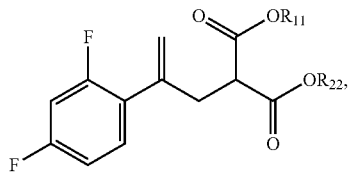
(CC)

wherein $R_{11}$ and $R_{22}$ are independently an optionally suitably substituted alkyl group having from 1 to 5 carbon atoms, preferably ethyl, wherein, after (ii) and before (iii), the compound of formula (CC) is optionally separated by extraction in a suitable solvent, preferably cyclohexane;

(iii) reducing the compound of formula (CC) to obtain a compound of formula (DD)

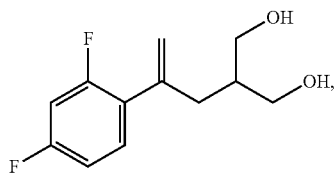
(DD)

the reducing agent preferably being LiBH$_4$ which is used in an amount of at most 2 molar equivalents with respect to the compound of formula (CC), said reduction preferably being carried out in a suitable solvent preferably comprising water, the solvent preferably being selected from the group consisting of water, alcohol, and a mixture of water and at least one alcohol, more preferably from the group consisting of water, methanol, ethanol, isopropanol, and a mixture of water and at least one of these alcohols, more preferably from the group consisting of water, ethanol, isopropanol, and a mixture of water and at least one of these alcohols, more preferably from the group consisting of water, isopropanol, and a mixture of water and isopropanol, the solvent most preferably being a mixture of water and isopropanol, wherein the solvent preferably comprises from 1 to 20 vol.-%, more preferably from 5 to 15 vol.-% of water;

(iv) acylating the compound of formula (DD) with isobutyric anhydride to obtain a compound of formula (EE)

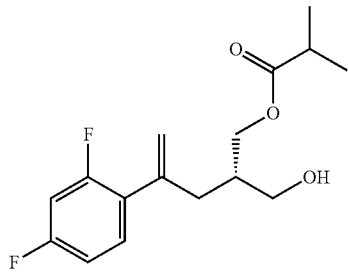
(EE)

said acylation preferably being carried out in the presence of a suitable enzyme, preferably Novo SP 435 enzyme, in a suitable solvent, preferably acetonitrile or toluene, more preferably toluene,
wherein after (iv) and before (v), the compound of formula (EE) is preferably at least partially crystallized;
(v) reacting the compound of formula (EE) with a halogen Hat selected from the group consisting of $Cl_2$, $Br_2$ and $I_2$, preferably $I_2$, in the presence of a base in a solvent to obtain a compound of formula (FF)

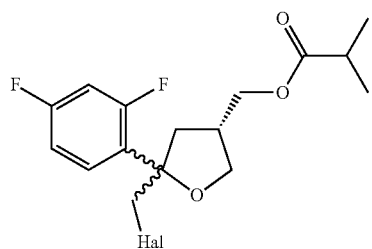

(FF)

wherein preferably from 80 to 95%, more preferably from 85 to 95% of the molecules of compound (FF) are present as cis-isomer of formula (FFa)

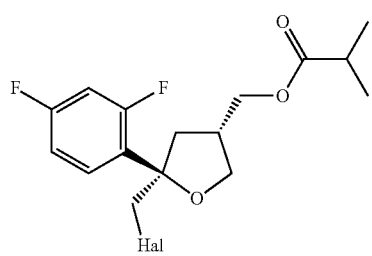

(FFa)

and preferably from 20 to 5%, more preferably from 15 to 5% of the molecules of compound (FF) are present as trans-isomer of formula (FFb)

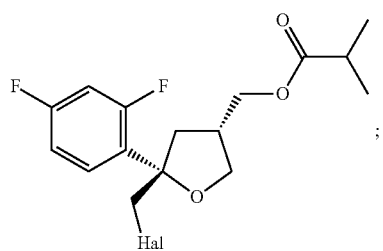

(FFb)

;

wherein the solvent is preferably ethyl acetate and wherein the base is preferably sodium hydrogencarbonate, and wherein the temperature at which the compound of formula (EE) is reacted is preferably less than 0° C., more preferably not higher than −5° C. and even more preferably not higher than −10° C.;
(vi.1) heating the compound of formula (FF) preferably at a temperature in the range of from +70 to +100° C., more preferably from +80 to +95° C., more preferably from +85 to +90° C., preferably in the absence of DMPU (1,3-dimethyl-3,4,5,6-tetrahydro-2(1H)-pyrimidinone), in a solvent, preferably a polar aprotic solvent, for example DMF (N,N-dimethylformamide) and DMSO, more preferably DMSO, with a 1,2,4-triazole alkali metal salt, preferably the sodium salt, and treating the resulting reaction mixture with a base suitable to promote saponification of the ester moiety such as alkali metal hydroxides, alkali metal bicarbonates, alkali metal carbonates, alkaline earth metal hydroxides, alkaline earth metal bicarbonates, and alkaline earth metal carbonates, preferably alkali metal bases, said base preferably being added in aqueous and/or alcoholic media, wherein suitable alcohols are alcohols containing 1 to 6, preferably 1 to 4, more preferably 1 to 3, most preferably 1 to 2 carbon atoms, said base even more preferably being sodium hydroxide, preferably employed as aqueous solution, in the presence of methanol, to obtain a compound of formula (GG)

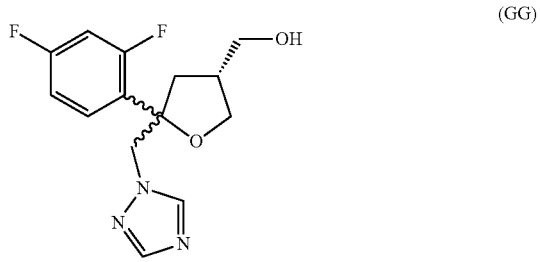

(GG)

wherein preferably from 80 to 95%, more preferably from 85 to 95% of the molecules are present as cis-isomer of formula (GGa)

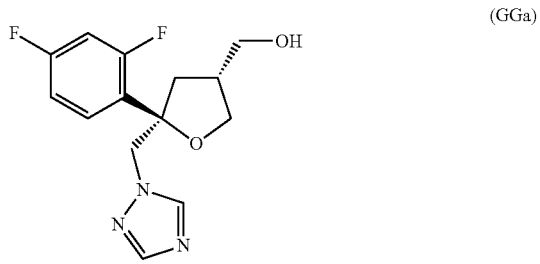 [SMILES: OC[C@@H]1CO[C@@](Cn2cncn2)(c2ccc(F)cc2F)C1]

(GGa)

and preferably from 20 to 5%, more preferably from 15 to 5% of the molecules are present as trans-isomer of formula (GGb)

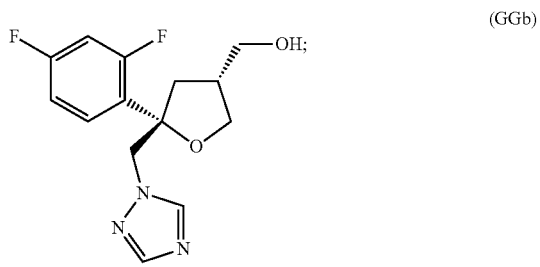 [SMILES: OC[C@@H]1CO[C@](Cn2cncn2)(c2ccc(F)cc2F)C1]

(GGb)

(vi.2) separating the compound of formula (GG) from the reaction mixture obtained from (vi.1) by extraction in a suitable solvent, the solvent preferably being a polar water-immiscible solvent, more preferably an ester such as ethyl acetate or isopropyl acetate, an ether such as tetrahydrofuran or methyl tetrahydrofuran, a ketone such as methyl isobutyl ketone, a halogenated solvent such as DCM, toluene, or a mixture of two or more of these solvents, more preferably an ester or an ether, more preferably an ether, and even more preferably methyl tetrahydrofuran.

4. The process of embodiment 3, wherein the method according to which the compound of formula (GG) is provided in (I) further comprises
   (vii) at least partially crystallizing the compound of formula (GG) after (vi.2).

5. The process of any of embodiments 1 to 4, wherein the first suitable solvent in which the compound of formula (GG) is comprised is an organic solvent, preferably an alcohol and/or a precursor of an alcohol, an ether, a ketone, an ester, or a mixture of two or more thereof.

6. The process of any of embodiments 1 to 5, wherein the first suitable solvent in which the compound of formula (GG) is comprised is selected from the group consisting of ethyl acetate, isopropyl acetate, diethyl ether, tetrahydrofuran (THF), methyl tetrahydrofuran, dioxane, methanol, n-propanol, 1-butanol, 2-butanol, 2-methyl-1-butanol, 3-methyl-1-butanol, acetone, 2-butanone, and methyl isobutyl ketone (MIBK), and wherein the second solvent is selected from the group consisting of dioxane, tetrahydrofuran (THF), diethyl ether, diisopropyl ether, methyl tert-butyl ether (MTBE), ethyl acetate, methanol, n-propanol, 1-butanol, 2-butanol, 2-methyl-1-butanol, 3-methyl-1-butanol, and toluene.

7. The process of embodiment 5 or 6, wherein the first and/or the second solvent comprise(s) an alcohol and/or a precursor of an alcohol.

8. The process of embodiment 7, wherein the first solvent is MIBK and the second solvent is THF, or wherein both the first and the second solvent is n-butanol.

9. The process of embodiment 7 or 8, wherein treating in (II) is carried out at a temperature in the range of from 20 to 100° C., preferably from 40 to 80° C., more preferably from 55 to 65° C.

10. The process of any of embodiments 7 to 9, wherein in (II), HCl comprised in the second solvent is employed relative to the compound of formula (GG) in a molar ratio HCl:(GG) in the range of from 1.0:1 to 2.0:1, preferably from 1.1:1 to 1.8:1, more preferably 1.2:1 to 1.7:1, more preferably from 1.3:1 to 1.5:1.

11. The process of any of embodiments 7 to 10, further comprising, after (II), at least partially crystallizing the HCl salt of compound of formula (GG).

12. The process of embodiment 11, wherein the at least partially crystallized HCl salt of compound of formula (GG) contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

13. The process of any of embodiments 7 to 12, further comprising
   (IIa) separating the at least partially crystallized HCl salt of compound of formula (GG), preferably by filtration, optionally followed by washing with a suitable solvent, preferably with MIBK.

14. The process of any of embodiments 1 to 6, wherein treating in (II) is carried out at a temperature in the range from 0 to 100° C. and wherein in (II), HCl comprised in the second solvent is employed relative to the compound of formula (GG) in a molar ratio HCl:(GG) in the range of from 1.0:1 to 3.0:1, preferably from 1.5:1 to 2.5:1, more preferably from 2.0:1 to 2.2:1.

15. The process of embodiment 14, further comprising, after (II), at least partially crystallizing the HCl salt of compound of formula (GG).

16. The process of embodiment 15, wherein the at least partially crystallized HCl salt contains from 80 to 95%, preferably from 85 to 95% of the HCl salt of the cis-isomer of formula (GGa) and from 20 to 5%, preferably from 15 to 5% of the HCl salt of the trans-isomer of formula (GGb).

17. The process of embodiment 15 or 16, further comprising
   (IIb) separating the at least partially crystallized HCl salt of compound of formula (GG), preferably by filtration, optionally followed by washing with a suitable solvent, preferably with methyl tert-butyl ether (MTBE), acetone or methyl isobutyl ketone (MIBK), more preferably with MTBE.

18. The process of embodiment 17 or embodiment 13, further comprising
   (III) subjecting the at least partially crystallized HCl salt of compound of formula (GG) to solid extraction in a suitable solvent, preferably comprising MIBK, to obtain the HCl salt of compound of formula (GG), thereby increasing the content with regard to the HCl salt of the cis-isomer of formula (GGa).

19. The process of embodiment 18, wherein the suitable solvent is MIBK or a mixture of MIBK and an alcohol, preferably n-butanol, the molar ratio of MIBK relative to the alcohol preferably being in the range of from 0.5:1 to 10:1, more preferably from 0.75:1 to 5:1, more preferably from 0.95:1 to 1.05:1.

20. The process of embodiment 18 or 19, wherein the solid extraction is carried out at a temperature in the range of from 20 to 100° C., preferably from 40 to 80° C., more preferably from 55 to 65° C.

21. The process of any of embodiments 18 to 20, wherein in (III), the concentration of the HCl salt of compound of formula (GG) is in the range of from 0.25 to 0.75, preferably from 0.55 to 0.65 mol/liter solvent.

22. The process of any of embodiments 18 to 21, further comprising, after (III), isolating the at least partially crystallized HCl salt of compound of formula (GG).

23. The process of any of embodiments 18 to 22, wherein the at least partially crystallized HCl salt of compound of formula (GG) obtained from (III) contains at least 97%, preferably at least 98% and more preferably at least 99% of the HCl salt of the cis-isomer of formula (GGa) and at most 3%, preferably at most 2% and more preferably at most 1% of the HCl salt of the trans-isomer of formula (GGb).

24. The process of any of embodiments 18 to 23, further comprising
   (IIIa) isolating the at least partially crystallized HCl salt of compound of formula (GG) from the mixture obtained from (III), preferably by filtration, optionally followed by washing with a suitable solvent, preferably with diethyl ether or methyl tert-butyl ether (MTBE).

25. The process of embodiment 24, further comprising subjecting the HCl salt obtained from (IIIa) to solid extraction according to the process of any of embodiments 18 to 23, preferably followed by separating the thus obtained HCl salt according to the process of embodiment 24.

As far as the reaction of the compound of formula (A) with the compound of formula (B) is concerned, no specific restrictions exist provided that the compound of formula (I) is obtained.

Preferably, according to step (0.1) of the present invention, the compound of formula (I) is provided by a process comprising (aa) reacting a compound of formula (A)

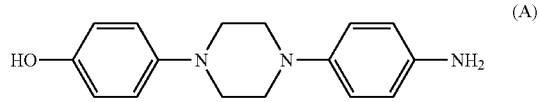

in a suitable solvent and in the presence of a suitable base, with a compound of formula (B)

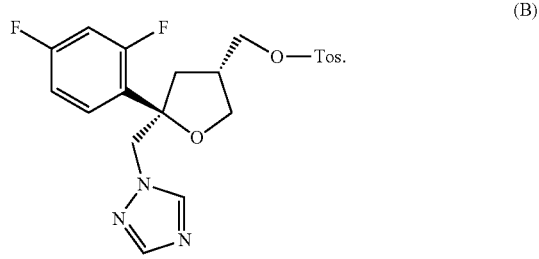

While as to the suitable solvent, no specific restrictions exist, preferred solvents according to the present invention are polar solvents. In particular, the suitable solvent is a polar protic solvent or a mixture of two or more thereof, or a polar aprotic solvent or a mixture of two or more thereof. More preferably, the suitable solvent is selected from the group consisting of dimethylsulfoxide (DMSO), dimethylformamide (DMF), N-methylpyrrolidone (NMP), sulfolane, methanol, ethanol, n-propanol, and iso-propanol, with ethanol or DMSO being particularly preferred.

Optionally, reacting in step (aa) is performed in the presence of at least one suitable anti-oxidant, such as butylated hydroxytoluene (BHT).

As to the suitable base, no specific restrictions exist provided that the compound of formula (A) and the compound of formula (B) can be reacted with each other to give the desired product. Preferred bases according to the present invention are inorganic bases, more preferably carbonates, hydroxides and/or hydrogencarbonates, and mixtures thereof. Even more preferably, the respective cations are selected from the group consisting of alkali metal ions, alkaline earth metal ions, or mixtures thereof. As alkali metals, lithium, sodium or potassium may be mentioned. As alkaline earth metals, magnesium, calcium, strontium or barium may be mentioned. Thus, a preferred base is in particular an alkali metal and/or an alkaline earth metal carbonate, an alkali metal and/or an alkaline earth metal hydroxide, and/or an alkali metal and/or an alkaline earth metal hydrogencarbonate, with sodium hydroxide and potassium carbonate being particularly preferred.

As to the preferred base sodium hydroxide, it is especially preferred to employ said base as aqueous solution. Employing an aqueous solution with a concentration of at least 20 wt.-%, preferably at least 45 wt.-% with respect to the base was found to be especially advantageous, and leads to a significant acceleration of the reaction rate as well as to increased selectivity of said reaction by reducing the formation of by-products.

With respect to the compound of formula (A), using an excess of the compound of formula (B) is preferred. Thus, the present invention relates to above-defined process wherein in step (aa), the molar ratio of the compound of formula (B) to the compound of formula (A) is greater than one. Further, preferred molar ratios are in the range of from greater than 1:1 to 1.2:1. Especially preferred molar ratios are in the range from 1.05:1 to 1.15:1, with a molar ratio of 1.1:1 being particularly preferred.

With respect to the compound of formula (A), using an excess of base is preferred. Thus, the present invention relates to above-defined process wherein in step (aa), the molar ratio of the base to the compound of formula (A) is greater than one. Further, preferred molar ratios are in the range of from greater than 1:1 to 2.0:1, more preferably from greater than 1:1 to 1.8:1, more preferably from greater than 1:1 to 1.6:1, more preferably from greater than 1:1 to 1.5:1.

The temperature under which the reaction in (aa) is carried out can be suitably chosen. Preferred temperatures are in the range of from 20 to at most 35° C., more preferably from 25 to at most 32° C.

The pH under which the reaction in (aa) is carried out is suitably controlled by addition of above-defined base. In particular, the reaction is carried out at a pH of at least 10.

From step (aa) of the present invention, the compound of formula (I) is obtained as crystallized product contained in the reaction mixture. According to a preferred embodiment, the compound of formula (I) is suitably separated from the reaction mixture and optionally suitably washed. Said optional washing is preferably carried out with a base as washing agent wherein inorganic bases such as sodium hydroxide are preferred. Base concentrations of from 0.1 to 5 wt.-%, are preferred, with 0.5 to 2 wt.-% being particularly preferred. Additionally, the compound of formula (I) may be further washed at least once with water and/or at least once with a suitable alcohol such as isopropanol.

While in general, the thus obtained product may be used for further steps without further treatment, it is preferred, according to the present invention, to re-crystallize the product obtained from step (aa). Therefore, the present invention relates to above-defined process which further comprises (bb) re-crystallizing the compound of formula (I).

While every suitable re-crystallization method is conceivable, it is especially preferred to re-crystallize the compound of formula (I) at least once from acetonitrile and/or water. It was found that compared to the isolation from water, the product obtained from re-crystallization from acetonitrile can be much easier dried, and thus, re-crystallization from acetonitrile allows for milder post-treatment conditions.

Drying of the thus re-crystallized compound of formula (I) is preferably carried out at a temperature of at most 75° C., preferably of at most 70° C. at a pressure of preferably at most 500 mbar, more preferably of at most 100 mbar, more preferably of at most 75 mbar.

Most preferably, either re-crystallization, or drying, or re-crystallization and drying is/are carried out under inert atmosphere such as under nitrogen atmosphere.

Optionally, the product may be treated with a suitable porous material to remove remaining impurities. Among others, charcoal may be mentioned as such suitable material.

Step (0.2)—Providing a Compound of Formula (IIa) or (IIb)

According to step (0.2) of the process of the present invention, a compound of formula (IIa)

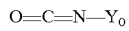

or (IIb)

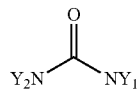

is provided.

As far as the compound of formula (IIa) is concerned, the residue $Y_0$ is an optionally substituted alkyl or aryl residue. The term "optionally substituted aryl residue" as used in this context of the present invention refers to aryl residues which have, for example, up to 6 or up to 12 carbon atoms. If such aryl residue is a substituted aryl residue, the number of carbon atoms refers to the number of carbon atoms of the corresponding unsubstituted aryl residue. The term "optionally substituted alkyl residue" as used in this context of the present invention refers to straight or branched alkyl residues which have, for example, 1 to 20, preferably 1 to 10 carbon atoms. If such alkyl residue is a substituted alkyl residue, the number of carbon atoms refers to the number of carbon atoms of the corresponding unsubstituted alkyl residue. As preferred compound of formula (IIa), phenylisocyanate may be mentioned.

As far as the compound of formula (IIb) is concerned, the residues $Y_1N$— and $Y_2N$— are the same or different and are optionally substituted nitrogen heterocycle moieties. The term "nitrogen heterocycle" as used in the context of the present invention relates to a cyclic residue which contains at least one, preferably one, two or three, more preferably two nitrogen atoms. The cyclic structure as such preferably contains from five to ten atoms in total, preferably from five to nine atoms in total. Especially preferred residues $Y_1N$— and $Y_2N$— are imidazolyl or benzimidazolyl. According to an especially preferred embodiment of the present invention, the compound of formula (IIb) is carbonyldiimidazole (CDI) of formula (IIc)

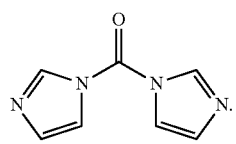

Typically, the compound of formula (IIb) is employed contained in a suitable solvent or in a mixture of two or more suitable solvents. Such suitable solvent is, for example, DCM, THF, Me-THF, DMF, acetonitrile, an ester like ethyl acetate or butyl acetate, with DCM being especially preferred.

Step (0.3)—Providing a Compound of Formula (III)

According to step (0.3) of the present invention, a compound of formula (III)

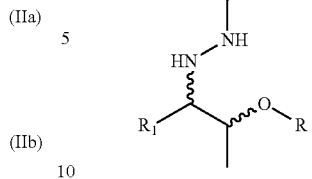

or a suitable salt thereof is provided.

In the compound according to formula (III), the residue $R_1$ is preferably a straight or branched alkyl residue which preferably has from 1 to 6 carbon atoms, namely 1, 2, 3, 4, 5, or 6 carbon atoms, more preferably from 1 to 4 carbon atoms, namely 1, 2, 3, or 4 carbon atoms, more preferably 1 or 2 carbon atoms, in particular 2 carbon atoms.

Further, in the compound of formula (III), the residue —R is either —H or a suitable hydroxyl protecting group. Conceivable protecting groups are given, for example, in Greene et al., "Protective Groups in Organic Synthesis", 3rd Ed., Wiley-Interscience (1999).

Preferably, the suitable hydroxyl protecting group is benzyl or a group —$SiR_aR_bR_c$ wherein the residues $R_a$, $R_b$ and $R_c$ may be the same or different and are preferably alkyl or aryl residues. The term "aryl residue" as used in this context of the present invention relates to a carbocyclic aromatic group, such as phenyl or naphthyl or the like. The term "alkyl residue" as used in the context of the present invention relates to straight or branched alkyl moieties which preferably have 1, 2, 3, 4, 5, or 6 carbon atoms, more preferably 1, 2 or 3 carbon atoms, more preferably 1 carbon atom. Especially preferably, the residue —R is —H or a hydroxyl protecting group selected from the group consisting of —$Si(CH_3)_3$ and benzyl, —R most preferably being —H.

Even more preferably, the compound of formula (III) is provided as crystalline compound with a specific amount of molecules present as compound of the formula

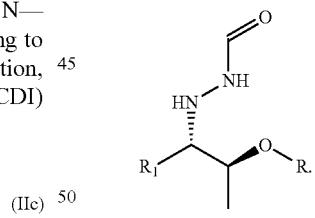

Thus, the present invention relates to above-defined process wherein the compound of formula (III) is a preferably crystalline compound

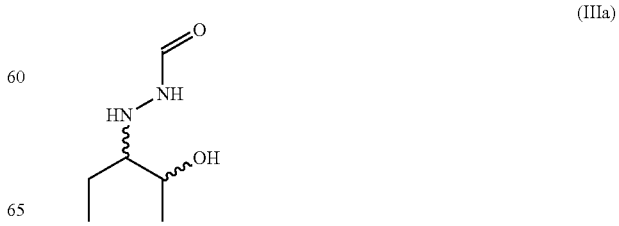

and wherein, according to a further preferred embodiment, at least 95%, preferably at least 97%, more preferably at least 99% of the molecules of said crystalline compound are present as compound of formula (IIIb)

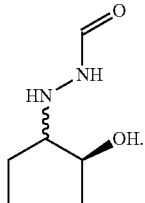
(IIIb)

Generally, there are no specific restrictions as far as the preparation of the compound of formula (III), in particular of formula (IIIa) is concerned.

According to a preferred process, the compound of formula (III) wherein —R=—H or a residue —SiR$_a$R$_b$R$_c$ is provided in step (1.3) of the present invention by a process which comprises the following steps:

(a) providing a chiral compound of formula (i)

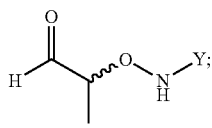
(i)

wherein Y is an optionally substituted aryl moiety, preferably an optionally substituted phenyl moiety, more preferably unsubstituted phenyl, said providing in (a) preferably comprising reacting propionaldehyde in a solvent with a compound of formula (j)

O=N—Y (j), preferably with nitrosobenzene, in the presence of a catalyst system preferably comprising at least one organocatalyst, more preferably proline (Pro), more preferably D-Pro, said catalyst system optionally further comprising a promoter, preferably a urea derivative, more preferably 1-(2-dimethylamino-ethyl)-3-phenyl urea, wherein preferably at least 95%, more preferably at least 97%, more preferably at least 99% of the molecules of the chiral compound of formula (i) provided in (a) are present as

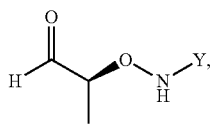
(ia)

said reaction of propionaldehyde with the compound of formula (j) preferably being carried out at a temperature in the range of from −15 to +5° C., preferably from −12 to +3° C., more preferably from −10 to 0° C., preferably in dichloromethane as solvent, and preferably in the presence of a catalytical amount of an acid, preferably acetic acid or propionic acid;

(b) reacting the compound of formula (i) with H$_2$N—NH—CHO in a solvent, preferably dichloromethane, to obtain a compound according to formula (ii)

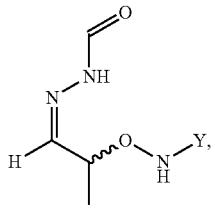
(ii)

wherein said reacting is preferably carried out in the presence of a molecular sieve, preferably having a pore diameter determined according to DIN 66131 in the range of from 0.3 to 0.5 nm (nanometre; 3 to 5 Angstrom), and wherein said reacting is preferably carried out at a temperature in the range of from −10 to +20° C., preferably from −5 to +5° C.;

(c) separating the compound of formula (ii) from the reaction mixture obtained from (b) by solvent extraction, wherein prior to (c), a solvent exchange is preferably carried out;

(d) optionally reacting the compound of formula (ii) in a solvent, preferably at a temperature in the range of from 15 to 70° C., with a silylating agent comprising the residue —SiR$_{aa}$R$_{bb}$R$_{cc}$ to obtain a compound of formula (iii)

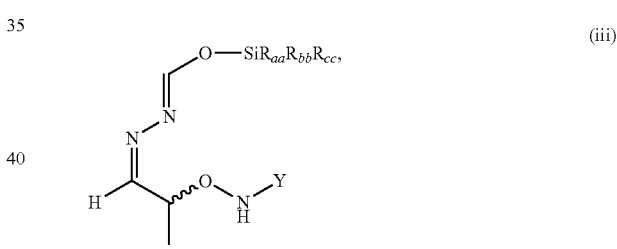
(iii)

wherein the residues R$_{aa}$R$_{bb}$ and R$_{cc}$ may be the same or different and are preferably alkyl or aryl residues, more preferably alkyl residues having from 1 to 6 carbon atoms, preferably from 1 to 4 carbon atoms, more preferably 1 or 2 carbon atoms, and wherein the silylating agent is preferably hexamethyldisilazane, trimethylchlorosilane, bis-trimethylsilyl acetamide or a mixture of two or three of these compounds, more preferably bis-trimethylsilyl acetamide;

(e) reacting the compound of formula (ii) or reacting the compound of formula (iii) with a nucleophilic compound comprising a nucleophilic residue R$_1$, the nucleophilic compound preferably being a Grignard compound R$_1$MgX wherein X is preferably selected from the group consisting of Cl, Br, and I, and wherein R$_1$ is preferably an alkyl residue preferably having from 1 to 6 carbon atoms, more preferably from 1 to 4 carbon atoms, more preferably 1 or 2 carbon atoms, most preferably 2 carbon atoms, in a solvent, preferably selected from the group consisting of toluene, tetrahydrofurane (THF), MTBE, and a mixture of THF and MTBE, to obtain a compound of formula (iv)

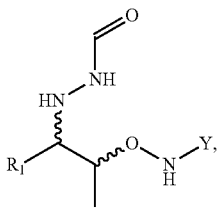

(iv)

wherein the nucleophilic compound is preferably CH₃CH₂MgCl, wherein the reaction with the nucleophilic compound is preferably carried out at a temperature in the range of from −80 to 0° C., preferably from −75 to −10° C., more preferably from −70 to −25° C.;

(f) reducing the compound of formula (Iv), preferably by hydrogenation, wherein preferably a solvent mixture comprising an alcohol comprising 1 to 4 carbon atoms, preferably methanol, ethanol, isopropanol, most preferably methanol, is employed, to obtain a compound of formula (III) with R=H

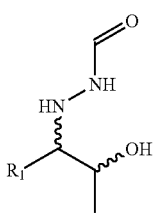

wherein the hydrogenation is preferably carried out at a temperature in the range of from 15 to 35° C., preferably from 20 to 30° C., at a hydrogen pressure in the range of from 0.5 to 50 bar, preferably from 1 to 20 bar, more preferably from 1 to 10 bar, in the presence of a precious metal containing catalyst, preferably a palladium containing catalyst, most preferably a Pd/C catalyst;

(g) optionally crystallizing the compound of formula (III) with R=H, wherein the compound of formula (III) is preferably crystallized from a mixture of MTBE and cyclohexane (CHX);

(h) optionally recrystallizing the compound of formula (III) with R=H, wherein the compound of formula (III) with R=H is preferably recrystallized from isopropyl acetate;

(i) optionally reacting the optionally crystallized compound of formula (III) with R=H in a solvent with a silylating agent comprising the residue —SiR$_a$R$_b$R$_c$ to obtain a compound of formula (III) with R=SiR$_a$R$_b$R$_c$

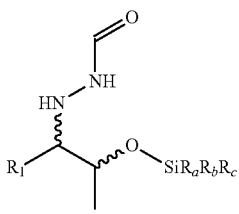

wherein the residues R$_a$, R$_b$ and R$_c$ are as defined above.

Step (0.4)—Mixing and reacting the compounds of formulas (I), (IIa) and/or (IIb), and (III)

As to step (0.4) of the present invention, the compounds of formulas (I), (IIa) and/or (IIb), preferably (IIb), and (III) can be mixed in any suitable order wherein each of said compounds can be employed as such or contained in at least one suitable solvent or in a suitable solvent mixture.

According to a preferred embodiment of the present invention, in a first step (0.4.1), the compounds of formulas (I) and (IIa) and/or (IIb), preferably (IIb), are mixed and at least partially reacted in a solvent to obtain a reaction mixture.

No particular restrictions exist concerning the solvent in which the reaction in step (0.4) and/or in step (0.4.1) is carried out. Preferably, the solvent is a polar aprotic solvent or a mixture of two or more thereof. More preferably, the at least one solvent is selected from the group consisting of dichloromethane (DCM), tetrahydrofurane (THF), methyl tetrahydrofurane (MeTHF), dimethyl formamide (DMF), acetonitrile (AN), an ester, preferably butylacetate (BuAc) or ethylacetate (EtAc), and a mixture of two or more thereof, preferably DCM or THF. Especially preferably, the solvent is DCM.

As described above, it is particularly preferred to employ the compound of formula (IIa) and/or (IIb), preferably (IIb), contained in DCM. As to the compound of formula (I), it is conceivable to introduce it either as solid compound, as, for example, obtained according to step (bb) described above wherein the compound of formula (I) is re-crystallized, preferably from acetonitrile, or contained in a suitable solvent such as DCM. According to a preferred embodiment of the present invention, the compound of formula (I) is introduced as solid compound obtained from step (bb) into the solution containing the compound of formula (IIa) or (IIb) wherein DCM is the most preferred solvent.

Preferably, the compound of formula (IIa) or (IIb) and the compound of formula (I) are employed in a molar ratio so that the compound of formula (IIa) or (IIb) is used in excess. Preferably, said molar ratio is in the range of from greater than 1:1 to 1.3:1, more preferably from greater than 1:1 to 1.2:1, more preferably from 1.05:1 to 1.15:1 such as 1.1:1.

After step (0.4.1), it is preferred—in a step (0.4.2.)—to add the compound of formula (III) to the reaction mixture obtained from step (0.4.1).

As to the compound of formula (III), it is conceivable to introduce it either as solid compound, as, for example, obtained according to step (h) described above wherein the compound of formula (III) is recrystallized, preferably from isopropyl acetate, or contained in a suitable solvent such as DCM, THF or, preferably, a mixture thereof. According to a preferred embodiment of the present invention, the compound of formula (III) is introduced as solid compound obtained from step (h) into the reaction mixture obtained from step (0.4.1).

Preferably, the compound of formula (III) is employed, relative to the compound of formula (I), in a molar ratio so that the compound of formula (III) is used in excess. Preferably, said molar ratio is in the range of from greater than 1:1 to 1.3:1, more preferably from greater than 1:1 to 1.2:1, more preferably from 1.05:1 to 1.15:1 such as 1.1:1.

The temperature under which the reaction in step (0.4) is carried out, is preferably in the range of from −20 to +40° C. More preferably, the reaction in step (0.4.1) is carried out at a temperature in the range of from −20 to +20° C., more preferably from −15 to 0° C., more preferably from −10 to −5° C. The reaction according to step (0.4.2) of the present invention is preferably carried out at a temperature in the range of from −20 to +40° C., more preferably, in a first reaction period, in the range of from −20 to 0° C., more preferably from −15 to 0° C., more preferably from −15 to −5° C., and, in a subsequent reaction period, in the range of from −5 to +40° C., preferably from 15 to 40° C., more preferably from 25 to 35° C., most preferably 30° C.

According to an embodiment of the present invention, in particular in case the compound of formula (IV') is the compound of formula (IVd), the compound of formula (IV') is suitably isolated. While every suitable method of isolating the compound of formula (IV'), crystallization methods are preferred. Among others, crystallization methods have to be mentioned yielding crystalline adducts such as crystalline solvent adducts of the compound of formula (IV'). Generally, all solvents are conceivable allowing for obtaining such crystalline solvent adducts of the compound of formula (IV'). A preferred solvent is, in this context, dichloromethane (DCM). In particular in case an imidazolyl group containing compound is employed as compound of formula (IIb), in particular in step (0.2) as described above, more preferably carbonyldiimidazole (CDI), the crystalline adduct of the compound of formula (IV') and the solvent, preferably DCM, additionally contains imidazole. According to an embodiment of the present invention, the crystalline adduct consists or essentially consists of the compound of formula (IV'), in particular (IVd), solvent, in particular DCM, and imidazole. Details as to step (0.5) are described below in section "Step (0.5)—Isolating the compound of formula (IV')".

Therefore, the present invention also relates to the process as described above comprising steps (0.1) to (0.4), further comprising (0.5) isolating the compound of formula (IV'), preferably by crystallization, more preferably as crystallized adduct
compound of formula (IV'):imidazole:DCM.

Further, the present invention also relates to the process as described above comprising steps (0.1) to (0.4), further comprising (0.5) isolating the compound of formula (IVd), preferably by crystallization, more preferably as crystallized adduct
compound of formula (IVd):imidazole:DCM.

Also, the present invention relates to said crystalline adducts as such.

Step (0.5)—Isolating the Compound of Formula (IV')

According to step (0.5), the compound of formula (IV') is isolated, preferably by crystallization, more preferably as crystallized adduct
compound of formula (IV'):imidazole:DCM.

Generally, the compound of formula (IV') can be crystallized from at least one suitable solvent, for example, from acetonitrile. Preferably, according to the present invention, the compound of formula (IV') is crystallized directly from the reaction mixture. For example, in a subsequent reaction period, the reaction mixture described above is preferably suitably cooled to initiate crystallization of the compound of formula (IV'), wherein the reaction mixture is preferably cooled to initiate crystallization and subsequently further cooled to a temperature in the range of from −10 to +5° C., more preferably from −5 to +5° C. Seed crystals may be added to initiate crystallization.

Therefore, the present invention relates to above-defined process comprising isolating the chiral compound of formula (IV')

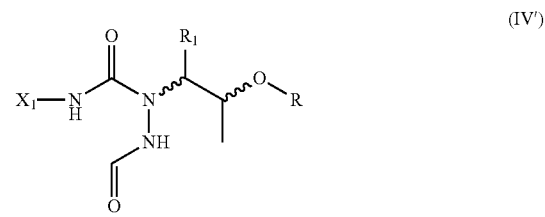

from the reaction mixture obtained from (0.4).

As described, said isolating is preferably carried out by crystallization. Further, it is also conceivable to isolate the compound of formula (IV') by chromatography.

From the reaction in step (0.4), the suitably isolated, preferably crystallized compound of formula (IV') is obtained. After separation from its mother liquor, the crystallized compound of formula (IV') can be suitably washed at least once and optionally dried.

According to a preferred embodiment of the present invention, the compound of formula (IV') being a compound of formula (IVb)

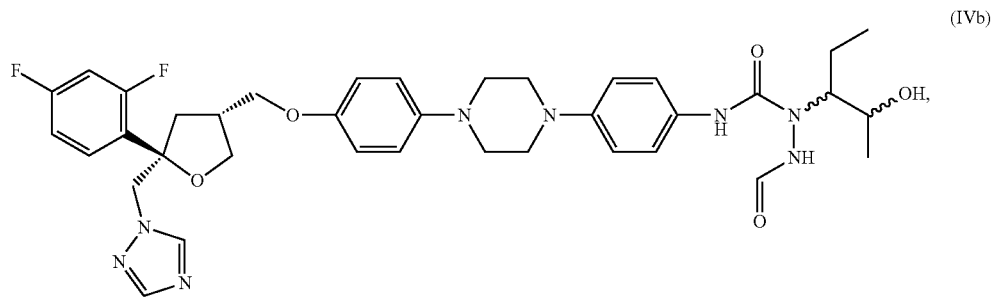 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

in particular being a compound of formula (IVd),

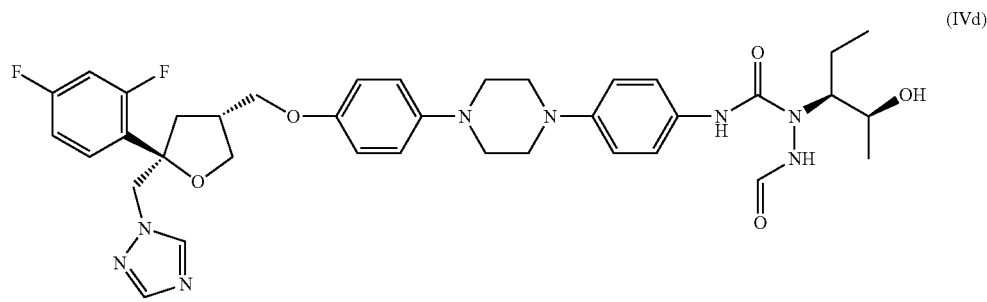 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

is crystallized directly from the reaction mixture preferably containing imidazole and a solvent such as preferably DCM, and by applying the above described reaction periods and conditions.

Surprisingly, it was found that in case the compound of formula (IVb), in particular the compound of formula (IVd) is directly crystallized from the reaction mixture in particular containing DCM and imidazole, the compound of formula (IVb), in particular the compound of formula (IVd) may crystallize as adduct compound of formula (IVd):imidazole:DCM for example as 1:1:1 adduct, wherein said adduct is obtained in at least one polymorphic form.

According to an optional embodiment of the present invention, the reaction in step (0.4) can be carried out in the presence of an acid which is either employed in stoichiometric or preferably employed in a substoichiometric amount. Typically, the acid used is at least partially soluble in the solvent or solvent mixture employed in step (0.4). Most preferably, the acid is trifluoroacetic acid (TFA) or para-toluenesulfonic acid (PTSA), with trifluoroacetic acid (TFA) being especially preferred. However, as indicated, reacting in step (0.4) can be carried out in the absence of trifluoroacetic acid (TFA), preferably in the absence of trifluoroacetic acid (TFA) or para-toluenesulfonic acid (PTSA), more preferably in the absence of an acid.

The process of the present invention, compared to known processes of the prior art, in particular compared to known processes for the preparation of posaconazole, is characterized in that it is carried out in the absence of a compound of formula Cl—C(=O)—O-Ph (phenyl chloroformate), in particular in the absence of an ester of a halogenated formic acid. Thus, the use of mutagenic compounds is avoided which may be found in the final product or the pharmaceutical composition containing such product.

Hence, the present invention relates to above-described process wherein the compound of formula (IV) and/or of formula (IV') is a preferably crystalline compound of formula (IVa)

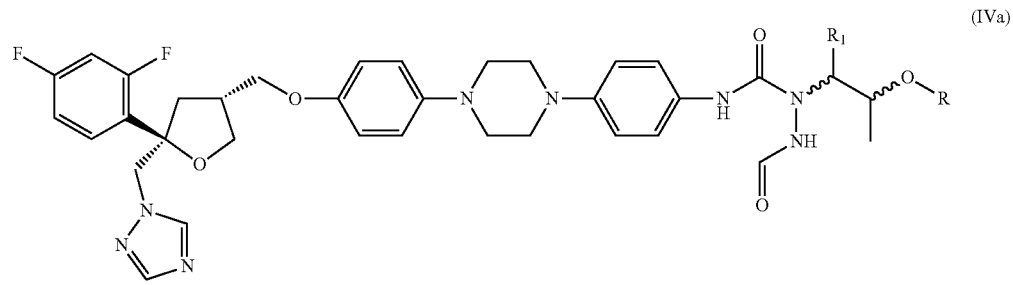
(IVa)

or a salt thereof, preferably a crystalline compound of formula (IVb)

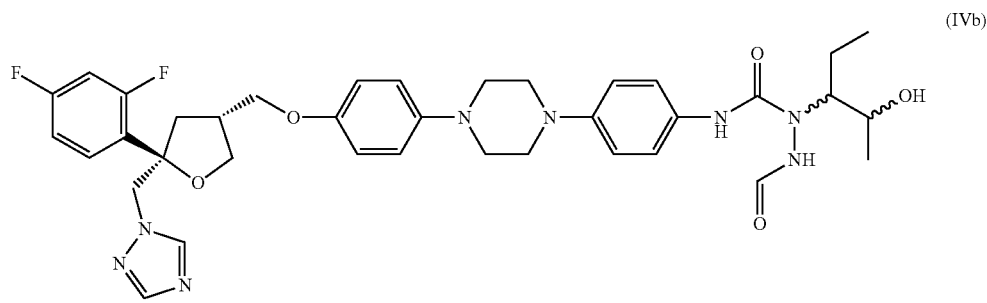 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVb)

wherein preferably at least 95%, more preferably at least 97%, more preferably at least 99% of the molecules of compound (IV) and/or of compound (IV') are present as compound of formula (IVc)

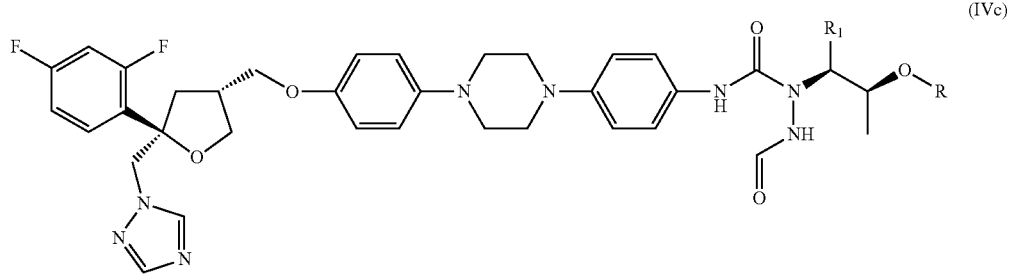

(IVc)

preferably as compound of formula (IVd)

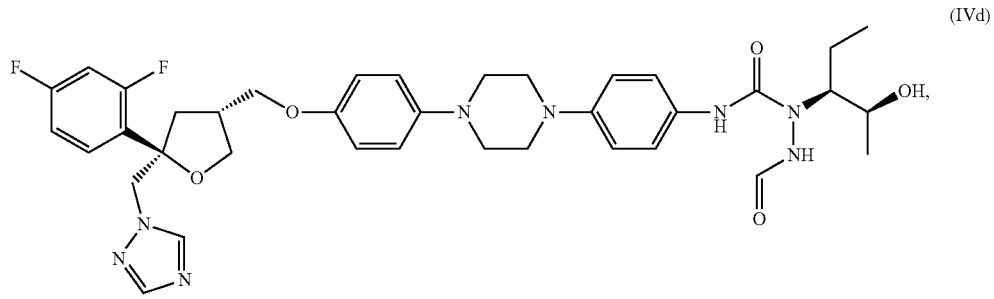

(IVd)

wherein $R_1$ is an alkyl residue preferably having from 1 to 6 carbon atoms, more preferably from 1 to 4 carbon atoms, more preferably 1 or 2 carbon atoms, most preferably 2 carbon atoms, $R_1$ in particular being ethyl, and wherein —R is —H or a suitable hydroxyl protecting group preferably selected from the group consisting of —$SiR_aR_b R_c$ and optionally substituted alkyl, aryl, alkaryl or aralkyl residues, where $R_a$, $R_b$ and $R_c$ are the same or different and selected from the group consisting of optionally suitably substituted alkyl and aryl residues, with —R preferably being —H or a hydroxyl protecting group selected from the group consisting of —$Si(CH_3)_3$ and benzyl, —R in particular being —H.

Preferred Use of the Protic Solvent System

As described above, the present invention generally relates to the use of a protic solvent system, preferably water and/or an alcohol, for the preparation of a compound of formula (V). According to a preferred embodiment, as mentioned above, a compound of formula (IVa) is employed as starting material for the inventive cyclization process, preferably a compound of formula (IVa) with R=H, more preferably a compound of formula (IVb). Surprisingly, it was found that the new protic solvent system allows for cyclization of compounds (IVa) and preferably (IVb) wherein the group —O—R is a non-protected hydroxyl group. Therefore, the present invention also relates to above-described use wherein a compound of formula (IVa) with the OH group in non-protected state, preferably a compound of formula (IVb) is employed as starting material.

the Mixture Directly Obtained from (2)

Generally, the present invention relates to a mixture comprising a compound of formula (V)

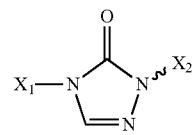

(V)

wherein $X_1$ is an optionally substituted aryl residue and $X_2$ is a linear or branched, optionally substituted alkyl residue, said mixture being directly obtained from a cyclization reaction wherein the cyclic moiety

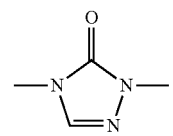

of the compound of formula (V) is formed, said directly obtained mixture comprising at least one protic solvent, preferably at least water and/or an alcohol. The term "directly obtained mixture" as used in this context of the present invention relates a mixture which is obtained from heating and cyclization according to (2) which mixture is not subjected to chemical or physical conditions leading to differences in its chemical composition.

As already described above, one characteristic feature of the process of the present invention is the possibility to carry out the cyclization reaction in the absence of bis-trimethylsilyl acetamide (BSA) and trimethylsilyl iodide (TMSI), preferably in the absence of a silylating agent in general.

Further, compared to the prior art discussed in the section "background prior art", the process of the present invention allows for carrying out the cyclization reaction in the absence of triethylamine, 1,8-diazabicyclo[5.4.0]undec-7-ene (DBU), and a phosphazene base.

Therefore, the present invention also relates to above-described, directly obtained mixture containing
- at most 5 weight-ppm, preferably at most 1 weight-ppm, said mixture in particular being free of bis-trimethylsilyl acetamide (BSA) and/or a trimethylsilyl (TMS) halide, preferably trimethylsilyl iodide (TMSI) and/or trimethylsilyl chloride (TMSCl), preferably of BSA and/or a trialkylsilyl halide, more preferably of a silylating agent; and/or
- at most 5 weight-ppm, preferably at most 1 weight-ppm, said mixture in particular being free of one or more compounds selected from the group consisting of triethylamine, 1,8-diazabicyclo[5.4.0]undec-7-ene (DBU), and a phosphazene base.

According to a conceivable embodiment of the present invention, the suitable base contained in mixture (2) is not potassium carbonate. As far as this embodiment is concerned, the mixture directly obtained from (2) contains
- at most 5 weight-ppm, preferably at most 1 weight-ppm, said mixture in particular being free of bis-trimethylsilyl acetamide (BSA) and/or a trimethylsilyl (TMS) halide, preferably trimethylsilyl iodide (TMSI) and/or trimethylsilyl chloride (TMSCl), preferably of BSA and/or a trialkylsilyl halide, more preferably of a silylating agent; and/or
- at most 5 weight-ppm, preferably at most 1 weight-ppm, said mixture in particular being free of one or more compounds selected from the group consisting of triethylamine, 1,8-diazabicyclo[5.4.0]undec-7-ene (DBU), potassium carbonate, and a phosphazene base.

Further, as described above, the compound of formula (IV) employed in (1) is preferably the compound

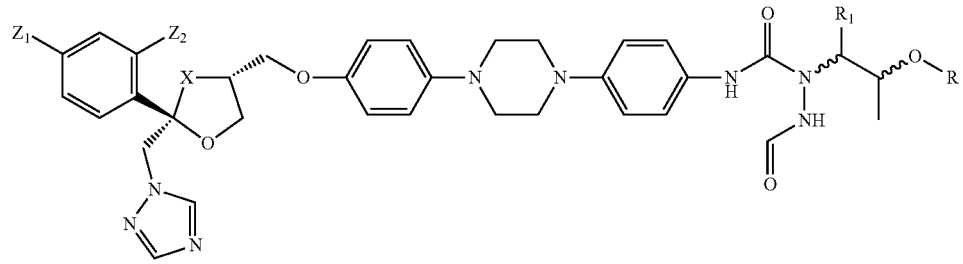

more preferably the compound

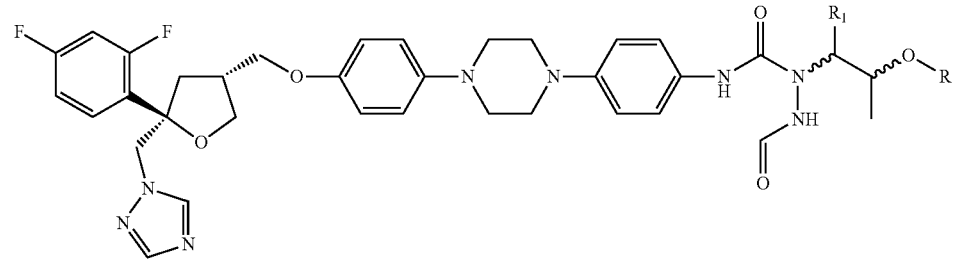

Therefore, the present invention also relates to above-described, directly obtained mixture wherein the compound of formula (V) is the compound

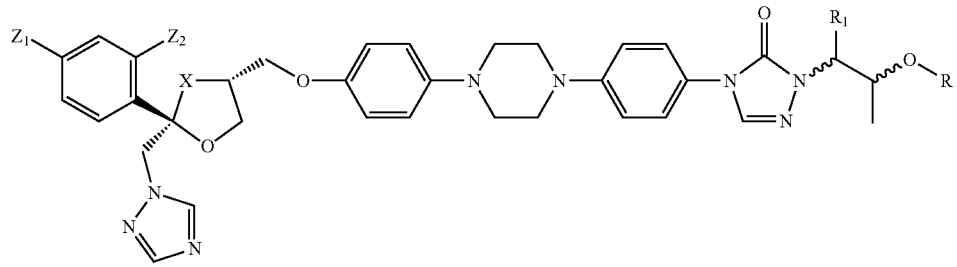

more preferably the compound of formula (Vf)

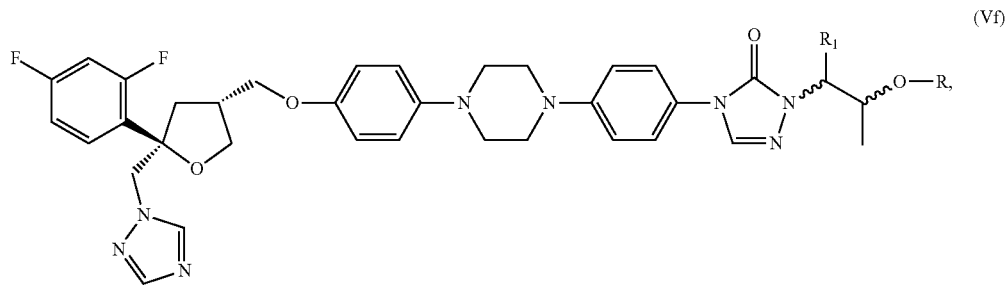

wherein $R_1$ is an alkyl residue preferably having from 1 to 6 carbon atoms, and wherein —R is —H or a suitable hydroxyl protecting group preferably selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues.

Surprisingly, it was found the process of the present invention allows for the cyclization reaction being carried out with very high selectivity, even at comparatively short heating times in (2) of at most 10 h or at most 8 h or at most 6 h. After these short heating times, a very high amount of starting material of the compound of formula (IV) is transformed into the compound of formula (V). Generally, the directly obtained mixtures contain at 0.5 area % (HPLC), preferably at most 0.4 area % (HPLC), more preferably at most 0.3 area % (HPLC), more preferably at most 0.2 area % (HPLC), more preferably at most 0.1 area % (HPLC) of the compound of formula (IV).

Therefore, the present invention relates to above-described, directly obtained mixture, wherein the compound of formula (V) is the compound of formula (Vb)

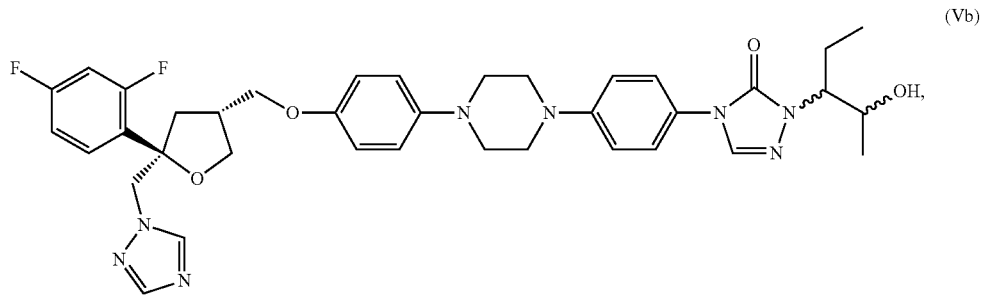 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

the mixture containing at most 0.1 area % (HPLC) of a compound of formula (IVd)

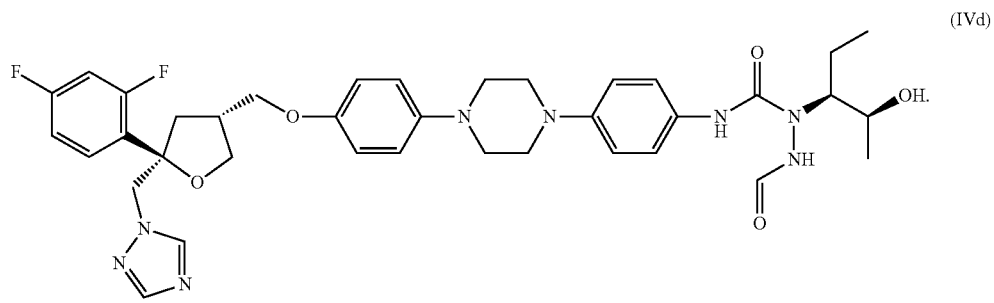 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

Acording to preferred embodiment of the present invention wherein; as compound of formula (IV); a compound of formula (IVa)

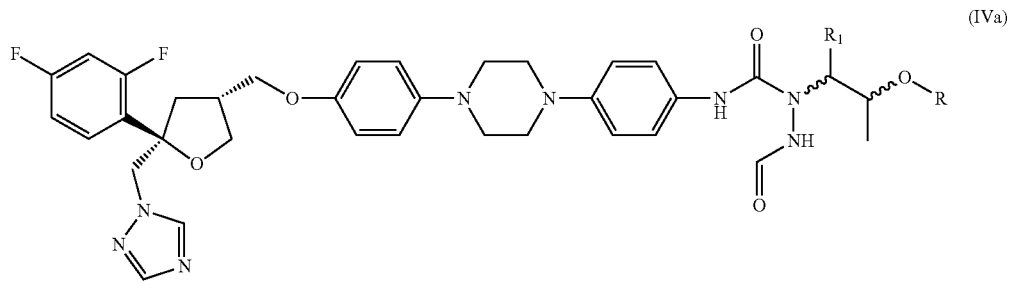

or a salt thereof, preferably a crystalline compound of formula (IVb)

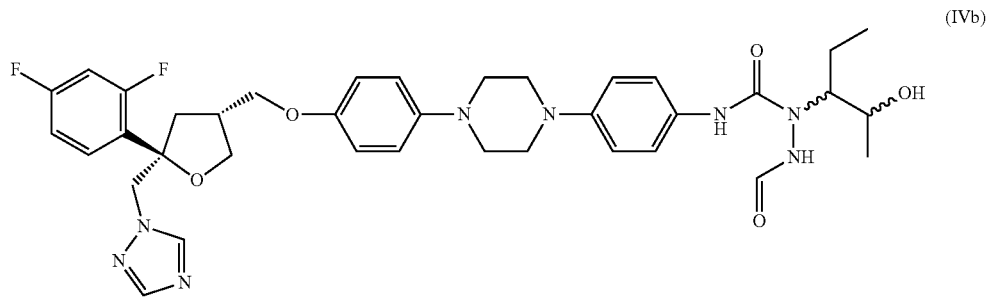 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

is employed wherein preferably at least 95%, more preferably at least 97%, more preferably at least 99% of the molecules of compound (IV) are present as compound of formula (IVc)

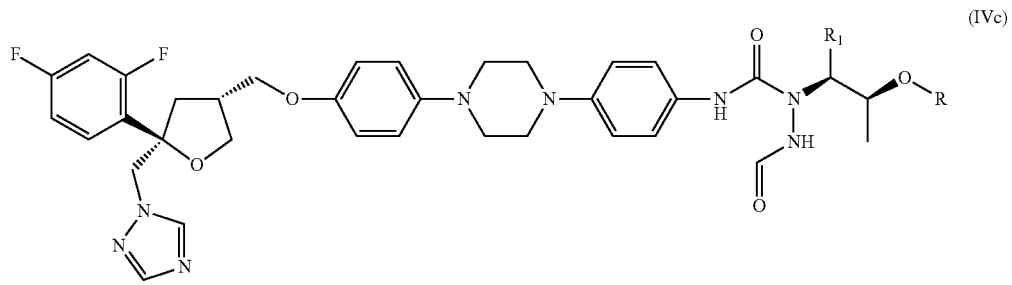

preferably as compound of formula (IVd)

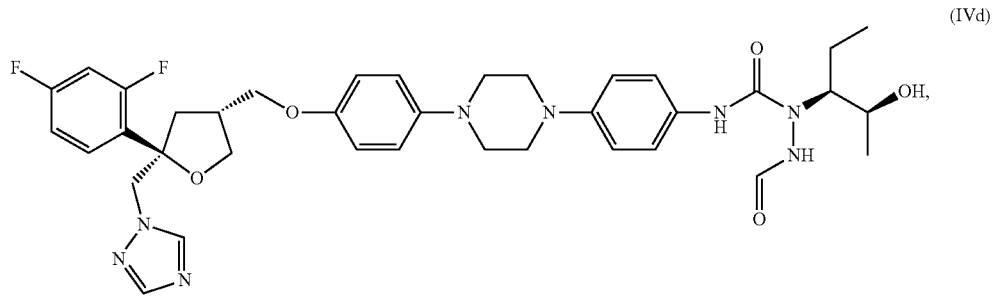 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

the mixture directly obtained from (2) preferably contains a compound of formula (Va)
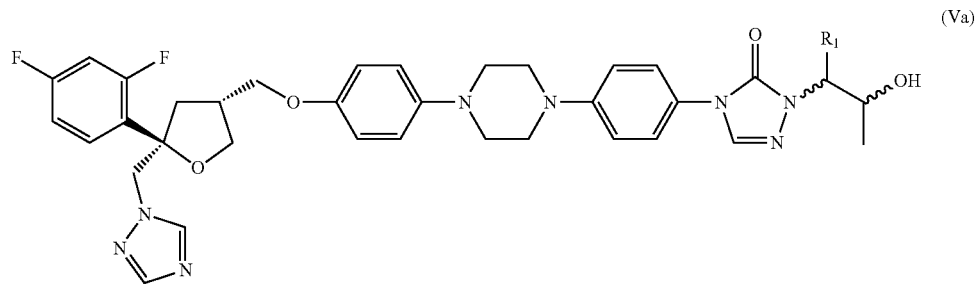
preferably a compound of formula (Vb)
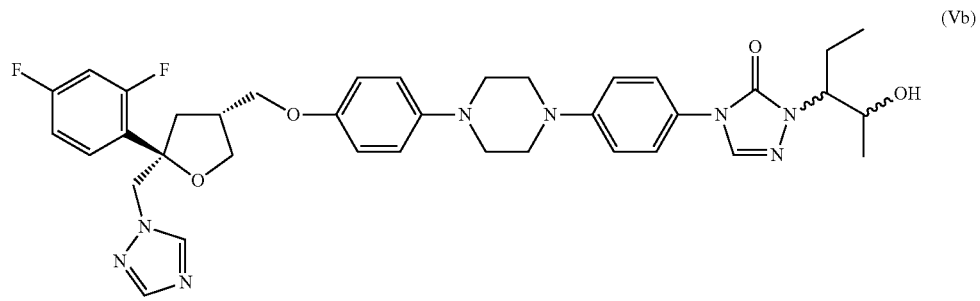 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
wherein preferably at least 95%, more preferably at least 97%, more preferably at least 99% of the molecules of said preferably crystalline compound are present as isomer of formula (Vc)
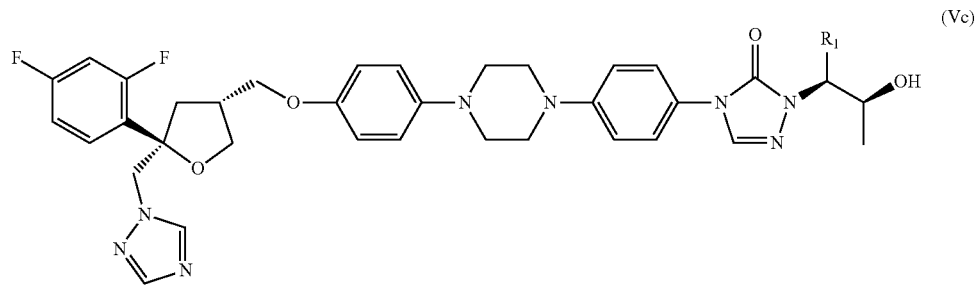
preferably as isomer of formula (Vd)
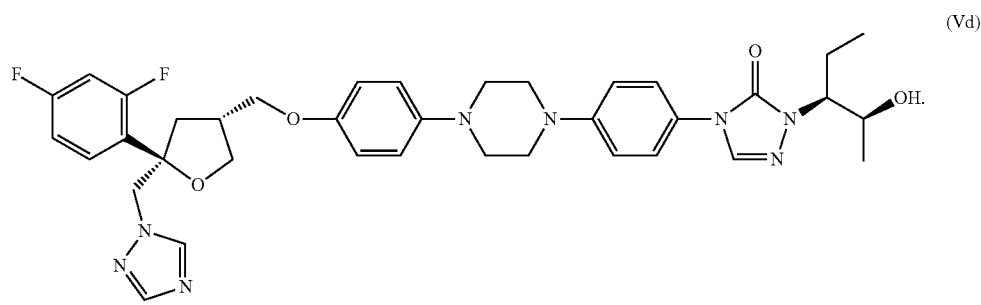 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Further, generally, the present invention relates to a mixture comprising a protic solvent system, a suitable base, and the compound of formula (V). Preferably, the present invention relates to a mixture comprising a protic solvent system comprising, preferably consisting of water and an alcohol, a suitable base being an inorganic base, and the compound of formula (V). More preferably, the present invention relates to a mixture comprising a protic solvent system comprising, preferably consisting of water and an alcohol having 1, 2, 3, 4 or 5 carbon atoms, an inorganic base being a hydroxide, and the compound of formula (V). Even more preferably, the present invention relates to a mixture comprising a protic solvent system comprising, preferably consisting of water and an alcohol selected from the group consisting of methanol, ethanol, isopropanol, and n-butanol, an inorganic base being an alkali metal hydroxide, and the compound of formula (V). According to one especially preferred embodiment of the present invention, the mixture obtained from (2) contains a protic solvent system consisting of water and iso-propanol which protic solvent system, even more preferably, has a water content of at most 25 vol-%, a suitable base being sodium hydroxide, and the compound of formula (V). In each of above-described preferred mixtures, the compound of formula (V) is a compound of formula (Va), preferably a compound of formula (Vb), wherein preferably at least 95%, more preferably at least 97%, more preferably at least 99% of the molecules of said compound are present as isomer of formula (Vc), preferably as isomer of formula (Vd).

Crystallization of the Compound of Formula (V)

As described hereinabove in detail, a mixture is obtained from (2) containing the compound of formula (V). From the mixture obtained from (2), the compound of formula (V) can be suitably crystallized wherein, after crystallization, the crystallized compound of formula (V) is optionally separated from the crystallization mixture. Therefore, the present invention relates to above-described process which further comprises (3) crystallizing the compound of formula (V) from the mixture obtained in (2);

(4) optionally separating the crystallized compound.

Prior to crystallization, the mixture obtained from (2) may be suitably treated with a suitable porous material to remove remaining impurities. Among others, charcoal may be mentioned as such suitable material. Treatment with, for example, charcoal is preferably performed under essentially inert, preferably nitrogen atmosphere for up to 30 minutes, preferably up to 15 minutes.

As described above, the mixture provided in (1) is heated in (2), preferably to a temperature in the range of from 60 to 100° C., more preferably from 70 to 85° C. Prior to crystallization in (3), it is preferred to suitably cool the mixture to a temperature of less than 60° C., preferably at most 55° C., more preferably at most 50° C. Therefore, the present invention relates to above-described process wherein prior to (3), the mixture obtained from (2) having a temperature in the range of from 60 to 100° C., more preferably from 70 to 85° C., is cooled to a temperature of less than 60° C., preferably at most 55° C., more preferably at most 50° C.

As to crystallization in (3), no specific restrictions exist. For example, crystallization can be carried out by adding suitable seeding crystals. Further, crystallization can be carried out by suitable cooling. Further, crystallization can be carried out by adding at least one suitable anti-solvent, wherein, according to a conceivable embodiment of the present invention, and depending on the protic solvent system used in (1), water can be added as suitable anti-solvent. Further, crystallization can be carried out by removing the solvent. As to the solvent, it is generally possible to subject the compound of formula (V) comprised in the mixture obtained from (2) to at least one extraction stage. Therefore, the present invention describes a process as defined above, wherein crystallization is carried out by adding seeding crystals and/or cooling and/or adding an anti-solvent, preferably water, and/or removing the solvent.

According to an especially preferred embodiment of the present invention, the compound of formula (V) comprised in the mixture obtained from (2) does not have to be subjected to an extraction stage prior to crystallization. Therefore, the present invention relates to above-described process wherein after (2) and before (3), the compound of formula (V) is not subjected to an extraction stage. A further major advantage of the process of the present invention has to be seen in the fact that the compound of formula (V) can be crystallized from the mixture obtained from (2), preferably after cooling to a temperature of less than 60° C., preferably at most 55° C., more preferably at most 50° C. Two main alternatives can be mentioned in this aspect.

According to a first alternative, the protic solvent system according to (1) already contains all components suitable for crystallization of the compound of formula (V) from the mixture obtained from (2). In this case, it is preferred to crystallize the compound of formula (V) directly from the mixture obtained from (2). The term "directly" as used in this context of the present invention relates to a process wherein for crystallization in (3), apart from optional seed crystals as herein described, no further chemical compound such as a further solvent is added.

According to a second alternative, the protic solvent system according to (1) contains some components suitable for crystallization of the compound of formula (V) from the mixture obtained from (2), and in (3), apart from optional seed crystals as herein described, at least one further chemical compound is added to the mixture obtained from (2).

As described hereinabove in detail, the protic solvent system according to (1) comprises water and/or an alcohol, and optionally at least one further organic solvent, said at least one further organic solvent preferably being a ketone, preferably acetone or MIBK, more preferably acetone.

According to an especially preferred embodiment of the present invention, the crystallization of the compound of formula (V) in (3) is carried out in the presence of a ketone, preferably acetone. Therefore, the present invention relates to above-described process wherein in (3), the compound of formula (V) is crystallized in the presence of a ketone, preferably acetone. Thus, in case the protic solvent system consists of water and a ketone, preferably acetone, the compound of formula (V) may be crystallized directly from the mixture obtained from (2). Further, in case the protic solvent system consists of an alcohol and ketone, preferably acetone, the compound of formula (V) may be crystallized directly from the mixture obtained from (2) wherein water may be additionally added in (3). Yet further, in case the protic solvent system consists of water and an alcohol and a ketone, preferably acetone, the compound of formula (V) may be crystallized directly from the mixture obtained from (2).

According to a yet further preferred embodiment, the protic solvent system consists of water and an alcohol which preferably contains 1, 2, 3, 4 or 5 carbon atom(s) and which more preferably is selected from the group consisting of methanol, ethanol, isopropanol, and n-butanol, and which is most preferably isopropanol. Therefore, according to the present invention, it is preferred that in (3), the compound of formula (V) is crystallized in the presence of water and an alcohol, preferably in the presence of water and an alcohol selected from the group consisting of methanol, ethanol, isopropanol, and n-butanol preferably isopropanol, more preferably in the presence of water and isopropanol. Since according to above-described preferred embodiment, a ketone, preferably acetone is present during crystallization in (3), a ketone, preferably acetone is added in (3) to the mixture obtained from (2) containing said water and said alcohol for crystallizing the compound of formula (V). In addition to said ketone, preferably acetone, optionally further water can be added in (3). According to a preferred embodiment, the ketone, preferably acetone is added in an amount so that the mixture from which the compound of formula (V) is crystallized contains from 1.6 to 2.5 weight-%, more preferably from 1.8 to 2.3 weight-%, more preferably from 1.9 to 2.1 weight-% of the compound of formula (V).

According to a yet further preferred embodiment, at least one suitable acid is added in (3) in order to at least partially neutralize the suitable base of the mixture obtained from (2). No specific restrictions exist concerning the chemical nature of the acid with the proviso that the compound of formula (V) can be crystallized in (3). Especially preferred is HCl. The preferred pH of the mixture from which the compound of formula (V) is crystallized is in the range of from 5 to 14, preferably from 5 to 9, more preferably from 6 to 8.

Therefore, according to a preferred embodiment, the present invention relates to above-described process wherein the protic solvent system consists of water and isopropanol wherein the water content of the protic solvent system is preferably at most 25 vol-%, and wherein in (3), acetone is added, optionally together with water, preferably in an amount so that the mixture from which the compound of formula (V) is crystallized contains the compound of formula (V) in the range of from 1.6 to 2.5 weight-%, preferably from 1.8 to 2.3 weight-%, more preferably from 1.9 to 2.1 weight-%. According to this embodiment, is even more preferred that the suitable base in (1) is an inorganic acid, preferably a hydroxide, more preferably sodium hydroxide. Further according to this embodiment, it is even more preferred in (3) that an acid, preferably HCl is added to neutralize said base.

Preferably, seed crystals are additionally added for crystallizing the compound of formula (V) in (3). Therefore, the present invention relates to above-described process wherein in (3), the compound of formula (V) is crystallized in the presence of seed crystals. In particular in case wherein the compound of formula (V) is the compound of formula (Vb)

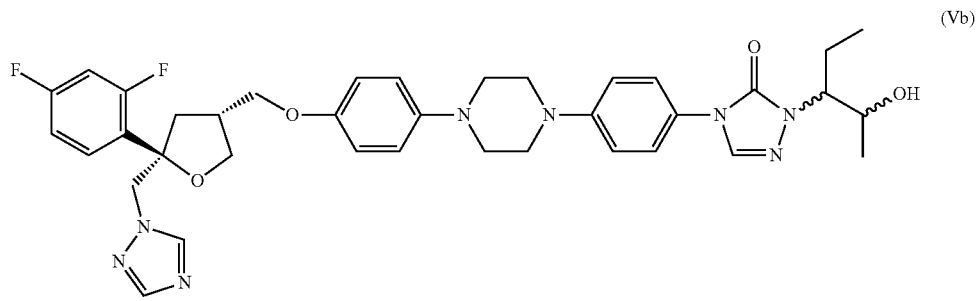 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

the seed crystals added in (3) comprise the crystalline compound of formula (Vd)

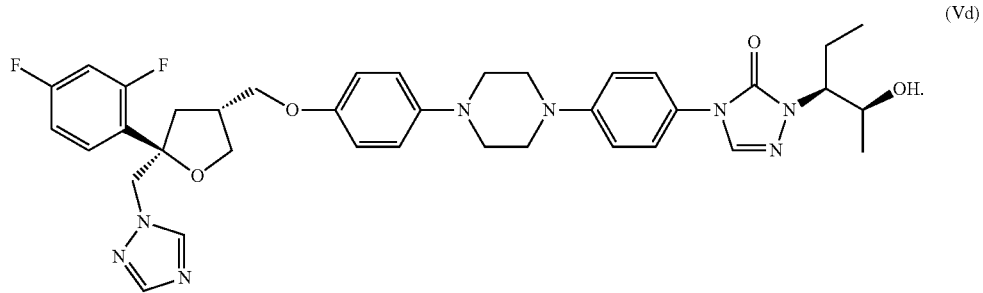 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vd)

While the seed crystals can be added to the mixture obtained from (2) which is preferably cooled to a temperature of less than 60° C., more preferably at most 55° C., more preferably at most 50° C., it is even more preferred, after the preferred addition of acetone, and optionally water, and prior to the addition of the seed crystals, to further cool the mixture to a temperature of 35° C. or less, preferably in the range of from 0 to 20° C., more preferably in the range of from 10 to 15° C.

Therefore, the present invention relates to above-described process wherein crystallizing in (3) is carried out at a temperature of 35° C. or less, preferably in the range of from 0 to 20° C., more preferably in the range of from 10 to 15° C., and at a pH in the range of from 5 to 14, preferably from 5 to 9, more preferably from 6 to 8.

After the preferred cooling and the preferred addition of seed crystals, further ketone, preferably acetone may be added in (3). In addition to said ketone, preferably acetone, optionally further water may be added. According to a preferred embodiment, further ketone, preferably acetone, optionally together with further water, is added in an amount so that the mixture contains from 0.75 to less than 1.6 weight-%, more preferably from 0.9 to 1.55 weight-%, more preferably from 1.0 to 1.5 weight-% of the compound of formula (V).

From the mixture obtained from step (3), containing the crystallized compound of formula (V), the crystallized compound of formula (V) is preferably suitably separated. Suitable separation is preferably carried out by filtration. The separated crystallized compound of formula (V), preferably contained in the filter cake obtained from filtration, is preferably washed with a suitable solvent or solvent mixture. Suitable washing agents are, for example, mixtures of water with at least one of methanol, ethanol, n-propanol, iso-propanol, ethers, preferably THF, ketones, preferably acetone, and acetonitrile, in particular water with acetone. The temperature of the washing agents is preferably in the range of from 0 to 10° C., more preferably from 5 to 10° C.

The separated and preferably washed crystallized compound of formula (V) is preferably dried at suitable conditions. Drying of the crystallized compound of formula (V) is preferably carried out at a temperature of at most 50° C., preferably of at most 45° C. at a pressure of preferably at most 500 mbar, more preferably of at most 100 mbar, more preferably of at most 75 mbar, more preferably at most 50 mbar.

According to the present invention, it was found that generally, there is no need to further purify the thus obtained crystallized compound of formula (V) by tedious processes taught in the art, in particular by chromatography, and can be used without further purification, in particular as antifungal agent. Therefore, the present invention relates to above-defined process wherein the crystallized compound obtained from (3) or (4) is not subjected to a subsequent chromatography purification stage.

According to above-described process according to which the compound of formula (V), especially preferably posaconazole is prepared, usually a specific polymorphic form or a mixture of two or more polymorphic forms is obtained. If desired, this (crude) compound of formula (V), especially preferably this (crude) posaconazole can be re-crystallized at least once to give only one of these polymorphic forms or to give another polymorphic form or a mixture of two or more other polymorphic forms.

According to an especially preferred embodiment of the present invention, wherein the compound of formula (V) is posaconazole according to formula (Vd), the compound of formula (V) is re-crystallized once, preferably from a mixture of acetone and water, preferably in the presence of seed crystals, said seed crystals comprising the crystalline compound of formula (Vd)

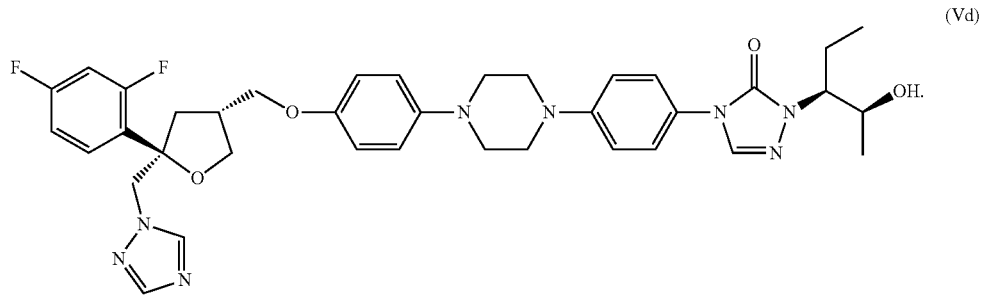 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

Therefore, the present invention relates to above-described process wherein the crystallized compound obtained from (3) or (4), in particular the compound of formula (Vb)

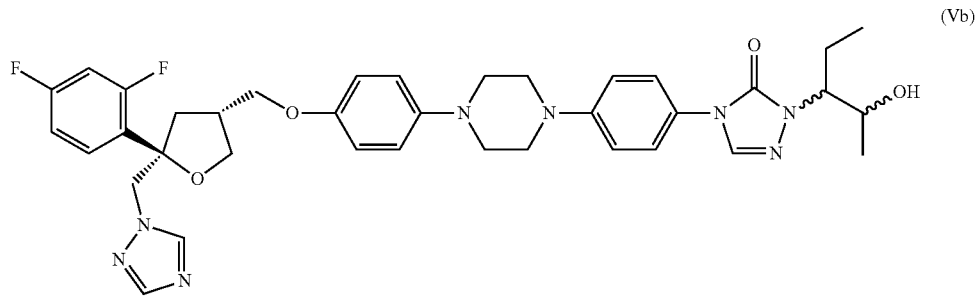 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein preferably at least 95%, more preferably at least 97%, more preferably at least 99% of the molecules of said crystalline compound are present as isomer of formula (Vd)

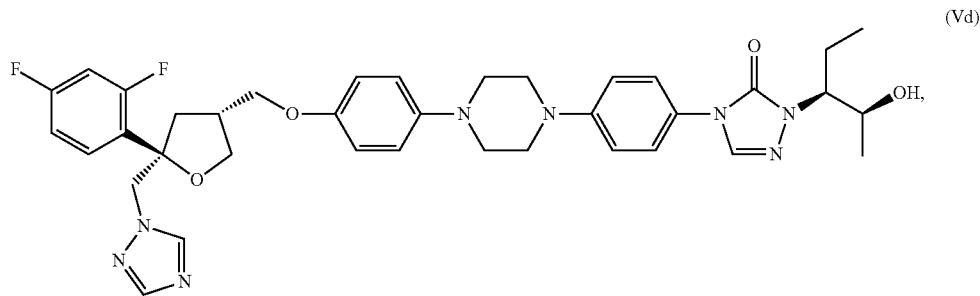 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

is re-crystallized, preferably from a mixture of acetone and water, and preferably in the presence of seed crystals, said seed crystals comprising the crystalline compound of formula (Vd).

Generally, the present invention also relates to a chiral compound of formula (V)

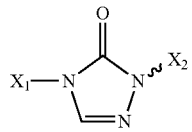
(V)

which is obtainable or obtained by a process as described herein above, in particular comprising steps (1), (2) and (3) or steps (1), (2), (3) and (4), and further relates to salts, preferably physiologically acceptable salts, to esters, preferably physiologically acceptable esters, and to solvates, preferably physiologically acceptable solvates, of the compound of formula (V), in particular of posaconazole.

Generally, the present invention also relates to a crystalline compound of formula (Vb)

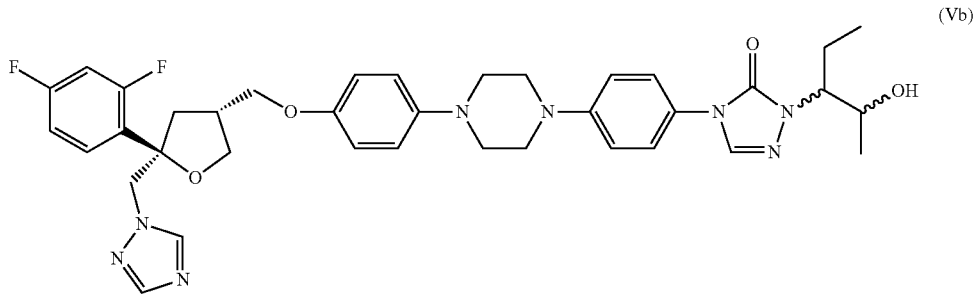 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

wherein preferably at least 95%, more preferably at least 97%, more preferably at least 99% of the molecules of said crystalline compound are present as isomer of formula (Vd)

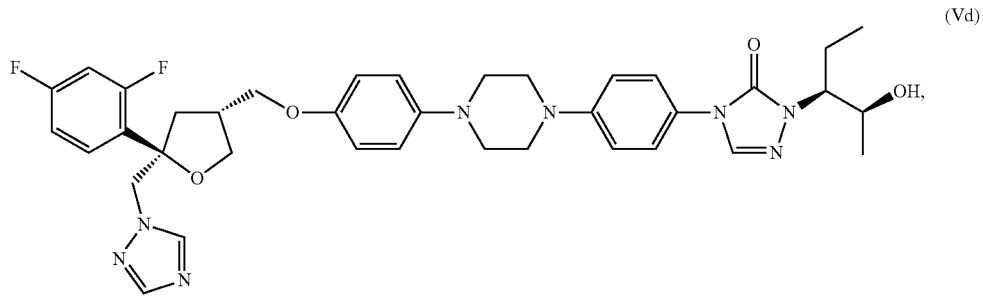 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

said crystalline compound being directly obtained by above-described process comprising steps (3) and (4), wherein in (3), the compound of formula (V) is crystallized in the presence of water and an alcohol, preferably isopropanol, and in the presence of a ketone, preferably acetone, wherein the compound of formula (IV) is a compound of formula (IVb)

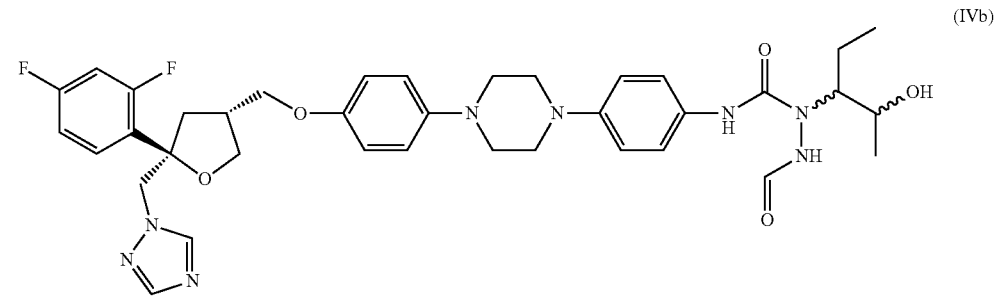 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVb)

wherein preferably at least 95%, more preferably at least 97%, more preferably at least 99% of the molecules of said compound are present as compound of formula (IVd)

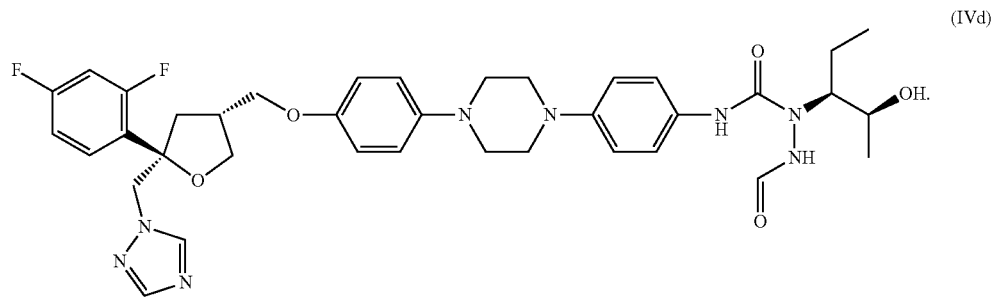 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVd)

As described above, the present invention allows for employing starting materials, in particular compounds of formula (IVa) with R═H and, more preferably, a compound of formula (IVb) in which starting material compounds the respective OH group is present in its non-protected state. Thus, suitable de-protection of the hydroxyl group necessary according to prior art teaching becomes redundant. Certain prior art documents wherein the hydroxyl protecting group is the benzyl group, teach said deprotection to be carried out by noble metal catalyzed, preferably palladium catalyzed transfer hydrogenation which involves the risk of contamination of the final product with noble metal, in particular palladium. No such risk is present according to the preferred embodiment of the present invention according to which said hydroxyl group is employed in its non-protected state, providing a further major advantage, in addition to the general lack of the respective deprotection step which renders the overall process economically and ecologically advantageous.

Therefore, the present invention also relates to a composition comprising a preferably crystalline chiral compound of formula (Va)

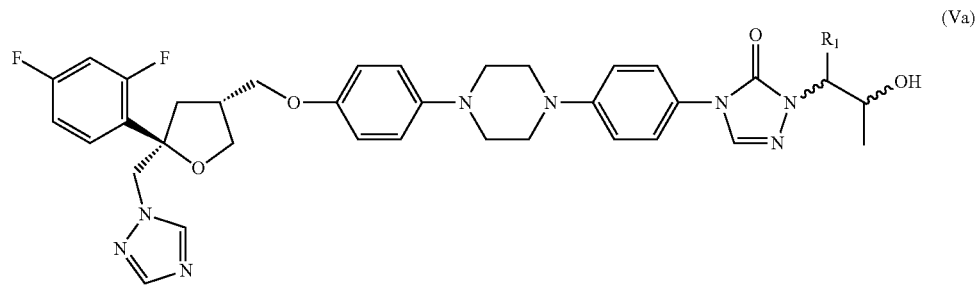

(Va)

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms,
said composition preferably comprising a compound of formula (Vb)

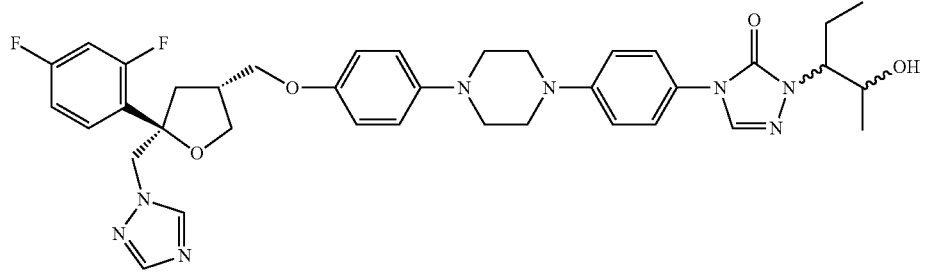

(Vb)

wherein preferably at least 95%, more preferably at least 97%, more preferably at least 99% of the molecules of said preferably crystalline compound are present as isomer of formula (Vc)

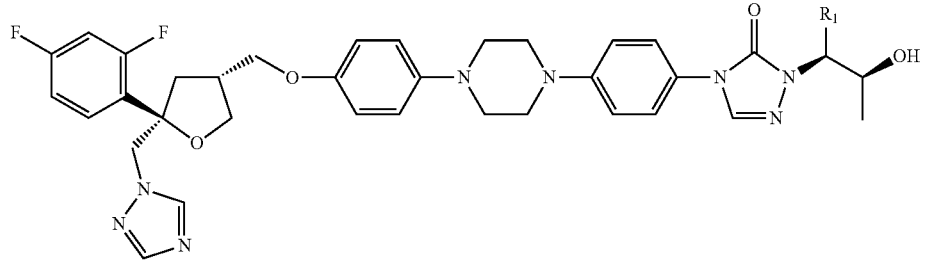

(Vc)

preferably as isomer of formula (Vd)

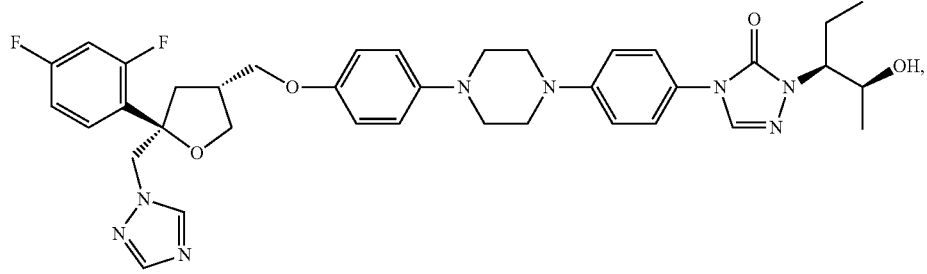

(Vd)

said composition containing at most 70 weight-ppm, preferably at most 50 weight-ppm, more preferably at most 30 weight-ppm, more preferably at most 10 weight-ppm, said composition in particular being free of a compound of formula (Ve)

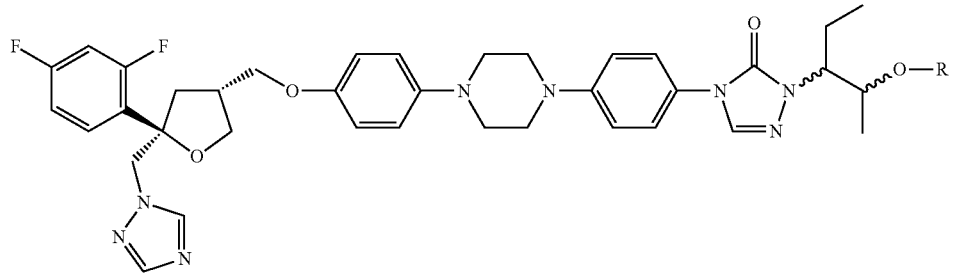

(Ve)

preferably a compound of formula (Vf)

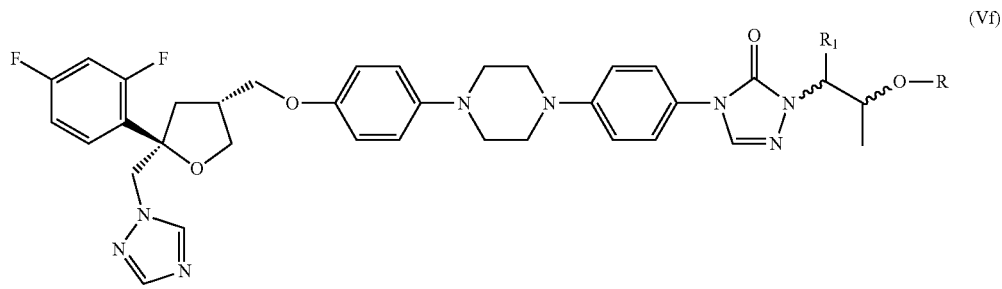

wherein —R is —CH$_2$—C$_6$H$_5$, —R preferably being selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues, —R more preferably being a hydroxyl protecting group,
and wherein said composition contains at most 0.1 area % (HPLC) of a compound of formula (IVd)

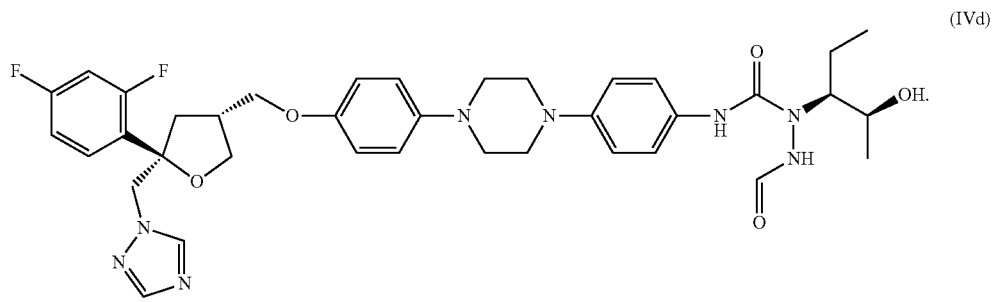 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

Said composition is, according to a further preferred embodiment, obtainable or obtained by above-described process comprising steps (1), (2), (3) and optionally (4).

Solvates of the Compound of Formula (V)

According to a further aspect, the present invention also relates to a solvate of the compound of formula (V), in particular of the compound of formula (Vb)

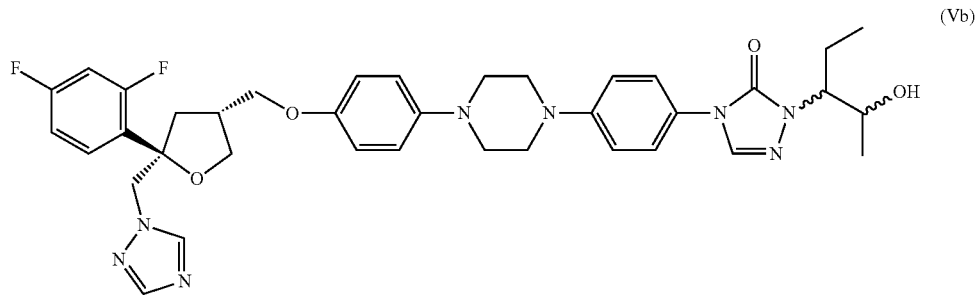 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein preferably at least 95%, more preferably at least 97%, more preferably at least 99% of the molecules of said crystalline compound are present as isomer of formula (Vd)

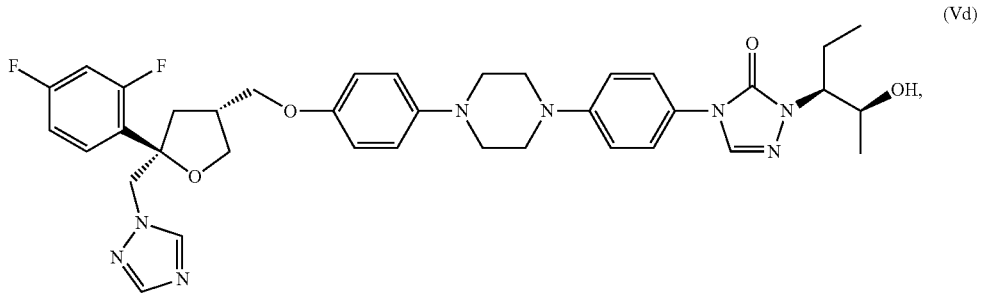 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

said crystalline compound being directly obtained by a process as herein described, wherein the compound of formula (IV) is a compound of formula (IVb)

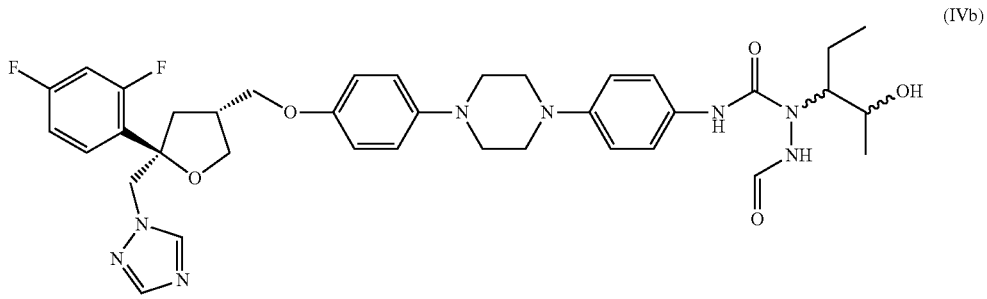 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

wherein preferably at least 95%, more preferably at least 97%, more preferably at least 99% of the molecules of said compound are present as compound of formula (IVd)

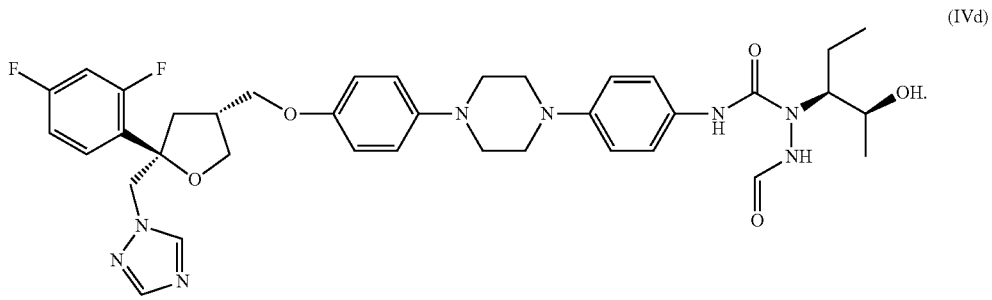 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

The specific chemical composition of above-mentioned solvate usually depends on the chemical nature of solvents used for the preparation of the compound of formula (V), in particular the chemical nature of the protic solvent system of (1). As described above in detail, a preferred protic solvent system according to the present invention consists of water and an alcohol. Therefore, conceivable solvates according to the present invention are solvates of said alcohol comprised in the protic solvent system and the compound of formula (V), preferably the compound of formula (Vb) wherein preferably at least 95%, more preferably at least 97%, more preferably at least 99% of the molecules of said crystalline compound are present as isomer of formula (Vd). Further conceivable solvates according to the present invention are solvates of an alcohol being selected from the group consisting of methanol, ethanol, isopropanol, and n-butanol, and the compound of formula (V), preferably the compound of formula (Vb) wherein preferably at least 95%, more preferably at least 97%, more preferably at least 99% of the molecules of said crystalline compound are present as isomer of formula (Vd). In particular, the present invention relates to a solvate of isopropanol and the compound of formula (V), preferably the compound of formula (Vb) wherein preferably at least 95%, more preferably at least 97%, more preferably at least 99% of the molecules of said crystalline compound are present as isomer of formula (Vd).

Such solvate is preferably prepared according to a process of the present invention wherein, as an alternative to above-described preferred process according to which crystallization is carried out in the presence of a ketone, preferably acetone, the crystallization of (3) is carried out in the absence of acetone, preferably in the absence of a ketone, and more preferably directly from the mixture obtained from (2) wherein as protic solvent system of (1), a protic solvent system is employed consisting of water and an alcohol, preferably of water and an alcohol being selected from the group consisting of methanol, ethanol, isopropanol, and n-butanol, more preferably of water and isopropanol.

Generally, said solvate, especially upon drying, may rearrange to a specific polymorphic form or a mixture of two or more polymorphic forms of the compound of formula (V), in particular of the compound of formula (Vb) as defined above which in turn may be re-crystallized at least once to give only one of these polymorphic forms or to give another polymorphic form or a mixture of two or more other polymorphic forms.

Uses

The compound of formula (V), in particular the antifungal agent according to the present invention, or obtainable or obtained according to the process of the present invention may be suitably contained in a pharmaceutical composition, in particular for treating fungal infections. Such pharmaceutical compositions typically comprise an antifungally effective amount of the antifungal agent, preferably posaconazole. In particular, the pharmaceutical compositions according to the present invention contains the above-defined composition which is especially preferably obtained or obtainable after step (3) or step (4) of the present invention, said composition comprising, preferably essentially consisting of a preferably crystalline chiral compound of formula (Vb) and containing at most 70 weight-ppm, preferably at most 50 weight-ppm, more preferably at most 30 weight-ppm, more preferably at most 10 weight-ppm, said composition in particular being free of a compound of formula (Ve).

In addition to the antifungally effective amount of the antifungal agent, the pharmaceutical composition of the present invention preferably contains at least one pharmaceutically acceptable additive. Any pharmaceutically acceptable additive can be employed as long as it does not detrimentally affect the properties of the pharmaceutical composition. Examples of typical pharmaceutically acceptable additives are described, for example, in WO 2010/000668 A1, on page 13, lines 13 to 23, the respective disclosure being incorporated herein by reference. Other suitable pharmaceutically acceptable additives are described e.g. in Remington's Pharmaceutical Sciences, 15th Ed., Mack Publishing Co., New Jersey (1991).

The pharmaceutical compositions of the invention can be produced in a manner known per se to the skilled person as described, for example, in Remington's Pharmaceutical Sciences, 15th Ed., Mack Publishing Co., New Jersey (1991).

The pharmaceutical composition according to the present invention may be a solid or a liquid. In this context, reference is made to WO 2010/000668 A1, page 13, lines 28 to 36, the respective disclosure being incorporated herein by reference. The pharmaceutically acceptable additive can also be an encapsulating material. In this context, reference is made to WO 2010/000668 A1, page 14, lines 1 to 6, the respective disclosure being incorporated herein by reference.

Formulations containing the antifungal agent of the present invention, preferably the composition of the present invention, may be topical formulations normally containing one or more non-toxic, pharmaceutically acceptable topical carriers, or other formulations such as those typically described for posaconazole. In this context, reference is made to WO 2010/000668 A1, page 14, lines 8 to 19, the respective disclosure and also the patent documents cited therein being incorporated herein by reference.

Therefore, the present invention relates to a pharmaceutical composition for treating fungal infections comprising an antifungally effective amount of a composition as defined above and a pharmaceutically acceptable carrier therefor.

In particular for these cases wherein the antifungal agent prepared according to the present invention is posaconazole, the agent, in particular above-defined composition, can be used as a medicament to treat or prevent any of the disorders which can be treated or prevented by posaconazole. In particular, it can be used for treating or preventing fungal infections, especially in mammals, such as humans. Thus, a method of treating or preventing a fungal infection by administering a therapeutically effective amount of above-defined composition to a patient in need thereof is also contemplated, as well as the above-defined composition for use in a method of treating or preventing fungal infections in mammals in need of such treating or preventing such infections. The above-defined composition is suitable for treating or preventing a wide range of infections caused by fungal pathogens, including yeasts, dermatophytes and molds. Typical fungal infections which can be treated are disclosed in WO 2010/000668 A1, on page 11, line 29 to page 12, line 5, the respective disclosure being incorporated herein by reference.

Therefore, the present invention relates to the above-defined composition for use as a medicament. Further, the present invention relates to the use of above-defined composition for the preparation of a medicament for treating or preventing fungal infections in mammals in need of such treating or preventing such infections.

Preferred embodiments of the present invention are given below wherein the specific combinations of embodiments resulting from the given dependencies are explicitly incorporated:

1. A process for the preparation of a compound of formula (V)

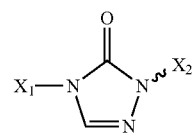

(V)

wherein $X_1$ is an optionally substituted aryl residue and $X_2$ is a linear or branched, optionally substituted alkyl residue, said process comprising
(1) providing a mixture comprising a compound of formula (IV)

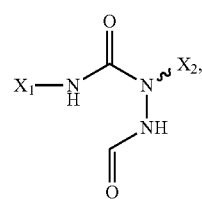

(IV)

a protic solvent system, and a suitable base;
(2) heating the mixture of (1) to obtain a mixture comprising the compound of formula (V).
2. The process of embodiment 1, wherein in (2), the mixture is heated to a temperature in the range of from 40 to 140° C., preferably from 50 to 120° C., more preferably from 60 to 100° C., more preferably from 70 to 85° C.

3. The process of embodiment 1 or 2, wherein in (2), the mixture is heated for a time in the range of from 0.1 to 10 h, preferably from 1 to 8 h, more preferably from 2 to 6 h.
4. The process of any one of embodiments 1 to 3, wherein the protic solvent system comprises water and/or an alcohol, and optionally at least one further organic solvent, said at least one further organic solvent preferably being a ketone.
5. The process of any one of embodiments 1 to 4, wherein the protic solvent system comprises, preferably consists of water and an alcohol, or comprises, preferably consists of water and a ketone.
6. The process of embodiment 4 or 5, wherein the alcohol comprises 1 to 5 carbon atoms and is preferably selected from the group consisting of methanol, ethanol, isopropanol, and n-butanol, and wherein the ketone comprises 3 to 9 carbon atoms and is preferably selected from the group consisting of acetone and methylisobutyl ketone (MIBK).
7. The process of any one of embodiments 1 to 6, wherein the protic solvent system comprises water wherein the water content of the protic solvent system is at most 25 vol-%.
8. The process of any one of embodiments 1 to 7, wherein the protic solvent system is a mixture of water and isopropanol, wherein the volume ratio of water relative to isopropanol is in the range of from 1:12 to 3:1, preferably from 1:5 to 1:1, more preferably from 1:4 to 1:3.
9. The process of any one of embodiments 1 to 8, wherein the suitable base has a $pK_b$ of less than 7, preferably of at most 3, more preferably of at most 0.
10. The process of any one of embodiments 1 to 9, wherein the suitable base is at least one hydroxide, or at least one carbonate, or at least one alcoholate, or a mixture of at least one hydroxide and at least one carbonate, or a mixture of at least one hydroxide and at least one alcoholate, or a mixture of at least one carbonate and at least one alcoholate, or a mixture of at least one hydroxide and at least one carbonate and at least one alcoholate.
11. The process of embodiment 10, wherein the hydroxide is selected from the group consisting of an alkali metal hydroxide and an alkaline earth metal hydroxide, preferably an alkali metal hydroxide, more preferably sodium hydroxide, potassium hydroxide, lithium hydroxide; wherein the carbonate is selected from the group consisting of an alkali metal carbonate and an alkaline earth metal carbonate, preferably an alkali metal carbonate, more preferably sodium carbonate, potassium carbonate; wherein the alcoholate is selected from the group consisting of an alkali metal alcoholate and an alkaline earth metal alcoholate, preferably an alkali metal alcoholate, more preferably sodium alcoholate, potassium alcoholate, lithium alcoholate.
12. The process of embodiment 10 or 11, wherein the alcoholate is selected from the group consisting of a methanolate, an ethanolate, an isopropanolate, and an n-butanolate.
13. The process of any one of embodiments 1 to 12, wherein in the mixture provided in (1), the molar ratio of the suitable base relative to the compound of formula (IV) is in the range of from 0.1:1 to 3:1, preferably from 0.75:1 to 1.5:1, more preferably from 0.95:1 to 1.05:1.
14. The process of any one of embodiments 1 to 13, wherein step (2) of heating the mixture of (1) is carried out in the absence of bis-trimethylsilyl acetamide (BSA) and a trimethylsilyl (TMS) halide, preferably trimethylsilyl iodide (TMSI) and/or trimethylsilyl chloride (TMSCl), more preferably a trialkylsilyl halide, preferably in the absence of a silylating agent.
15. The process of any one of embodiments 1 to 14, wherein $X_2$ is a residue according to formula (X2)

wherein $R_1$ is H or an alkyl residue preferably having from 1 to 6 carbon atoms, and wherein —R' is selected from the group consisting of —H, -alkyl, and —O—R wherein —R is —H or a suitable hydroxyl protecting group preferably selected from the group consisting of —$SiR_aR_bR_c$ and optionally substituted alkyl, aryl, alkaryl or aralkyl residues where $R_a$, $R_b$ and $R_c$ are the same or different and selected from the group consisting of optionally substituted alkyl and aryl residues, and wherein the dotted line in formula (X2) stands for the bond between $X_2$ and the N atom in formulas (IV) and (V).

16. The process of embodiment 15, wherein $R_1$ is an alkyl residue having from 1 to 4 carbon atoms, preferably 1 or 2 carbon atoms, most preferably 2 carbon atoms, in particular ethyl, and wherein —R' is —O—R wherein —R is —H or a hydroxyl protecting group selected from the group consisting of —$Si(CH_3)_3$ and benzyl, preferably —H.
17. The process of any one of embodiments 1 to 16, wherein $X_1$ is a residue according to formula (X1)

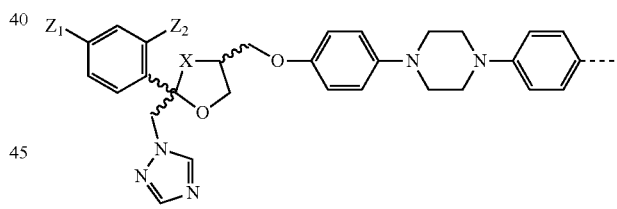

wherein $Z_1$ and $Z_2$ are independently F or Cl, preferably F, wherein —X— is —O— or —$CH_2$—, preferably —$CH_2$—, and wherein the dotted line in formula (X1) stands for the bond between $X_1$ and the NH group in formula (IV) and the bond between $X_1$ and the N atom in formula (V).

18. The process of any one of embodiments 1 to 17, wherein the residue $X_2$ is

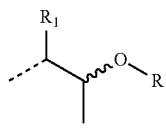

wherein $R_1$ is an alkyl residue preferably having from 1 to 6 carbon atoms, and wherein —R is —H or a suitable hydroxyl protecting group preferably selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues;
wherein the dotted line stands for the bond between X$_2$ and the N atom in formula (IV);
wherein the compound of formula (IV) is provided by a process comprising
(0.1) providing a compound of formula (I)

  (I)

or a salt thereof,
wherein X$_1$ is an optionally substituted aryl residue;
(0.2) providing a compound of formula (IIa)

  (IIa)

wherein Y$_0$ is an optionally substituted alkyl or aryl residue;
or, preferably, phosgene or a phosgene derivative of formula (IIb)

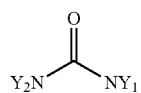  (IIb)

wherein Y$_1$N— and Y$_2$N— are the same or different optionally substituted nitrogen heterocycle moieties, preferably selected from the group consisting of imidazolyl and benzimidazolyl, more preferably imidazolyl, the preferred compound of formula (IIb) being carbonyldiimidazole (CDI);

(0.3) providing a compound of formula (III)

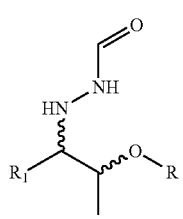  (III)

or a salt thereof,
(0.4) mixing and reacting the compounds of formulas (I), (IIa) and/or (IIb), and (III) in a solvent, preferably dichloromethane (DCM) in any order to obtain a reaction mixture containing the compound of formula (IV')

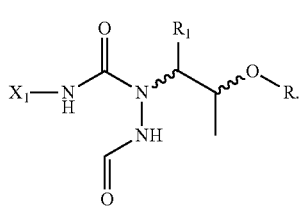  (IV')

19. The process of any of embodiments 1 to 18, wherein the compound of formula (IV) and/or of formula (IV') is a preferably crystalline compound of formula (IVa)

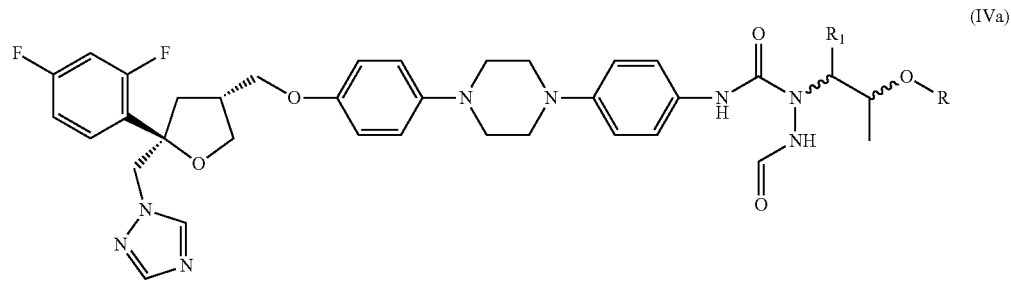  (IVa)

or a salt thereof, preferably a crystalline compound of formula (IVb)

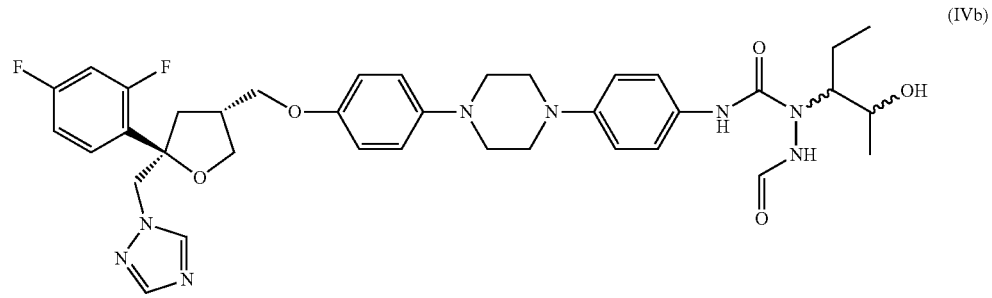 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]  (IVb)

wherein preferably at least 95%, more preferably at least 97%, more preferably at least 99% of the molecules of compound (IV) and/or of compound (IV') are present as compound of formula (IVC)

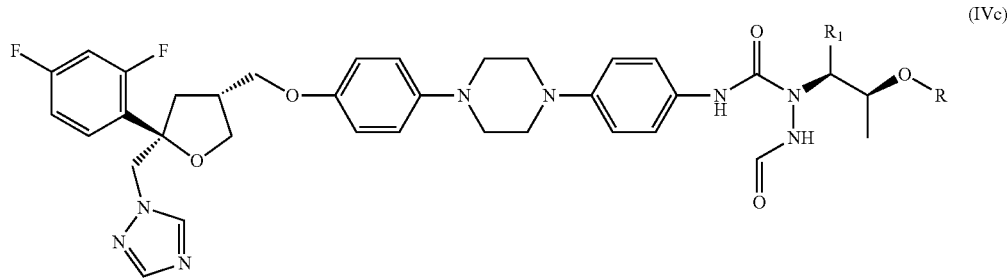

(IVc)

preferably as compound of formula (IVd)  compound of formula (IV'):imidazole:DCM.

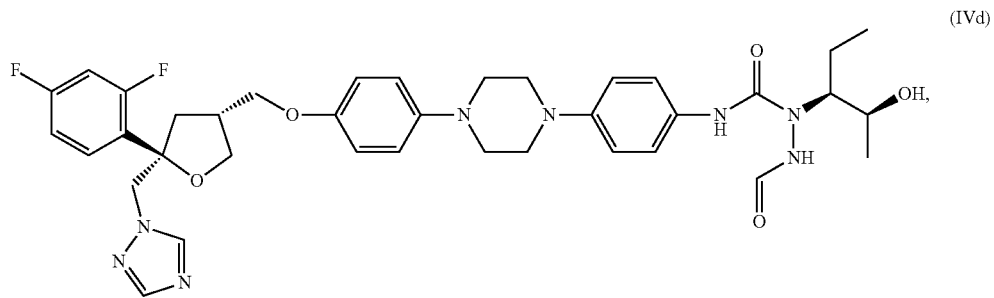

(IVd)

wherein R$_1$ is an alkyl residue preferably having from 1 to 6 carbon atoms, more preferably from 1 to 4 carbon atoms, more preferably 1 or 2 carbon atoms, most preferably 2 carbon atoms, R$_1$ in particular being ethyl, and wherein —R is —H or a suitable hydroxyl protecting group preferably selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues, with —R preferably being —H or a hydroxyl protecting group selected from the group consisting of —Si(CH$_3$)$_3$ and benzyl, —R in particular being —H.

20. The process of embodiment 19 insofar embodiment 19 is dependent on embodiment 18, wherein the compound of formula (IV') is the compound of formula (IVd), said process further comprising
(0.5) isolating the compound of formula (IV'), preferably by crystallization, more preferably as crystallized adduct 21. The process of any one of embodiments 1 to 20, further comprising
(3) crystallizing the compound of formula (V) from the mixture obtained in (2);
(4) optionally separating the crystallized compound.

22. The process of embodiment 21, wherein after (2) and before (3), the compound of formula (V) is not subjected to an extraction stage.

23. The process of embodiment 21 or 22, wherein in (3), the compound of formula (V) is crystallized in the presence of a ketone, preferably acetone.

24. The process of any one of embodiments 21 to 23, wherein in (3), the compound of formula (V) is crystallized in the presence of water and an alcohol, preferably isopropanol.

25. The process of any one of embodiments 21 to 24, wherein in (3), the compound of formula (V) is crystallized in the presence of seed crystals.

26. The process of embodiment 25, wherein the compound of formula (V) is the compound of formula (Vb)

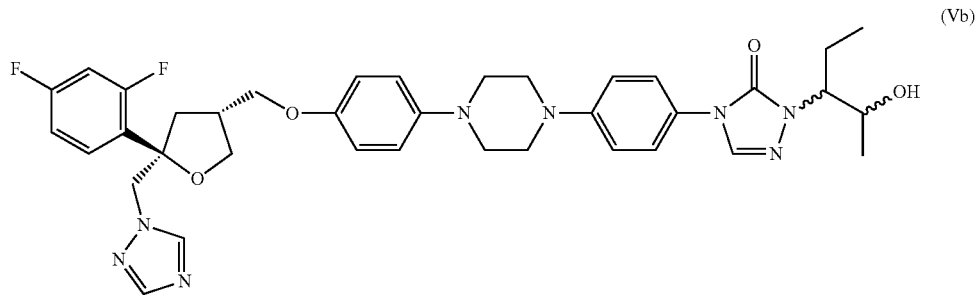 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

and the seed crystals comprise the crystalline compound of formula (Vd)

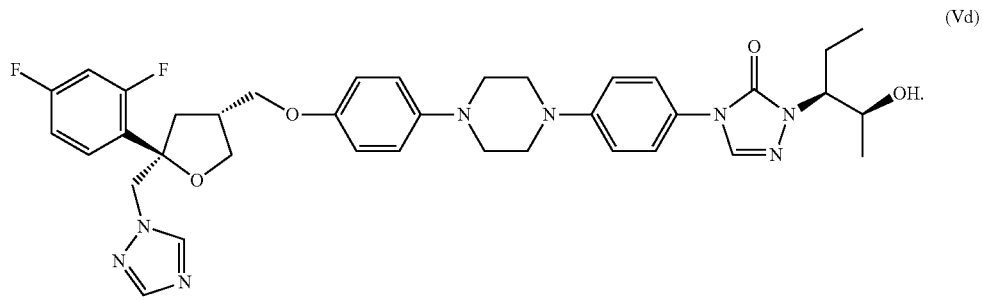 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

27. The process of any one of embodiments 21 to 26, wherein crystallizing in (3) is carried out at a temperature of 35° C. or less, preferably in the range of from 0 to 20° C., more preferably in the range of from 10 to 15° C., and at a pH in the range of from 5 to 14, preferably from 5 to 9, more preferably from 6 to 8.
28. The process of any one of embodiments 21 to 27, wherein the crystallized compound obtained from (3) or (4) is not subjected to a subsequent chromatography purification stage.
29. The process of any one of embodiments 21 to 28, wherein the crystallized compound obtained from (3) or (4), in particular the compound of formula (Vb)

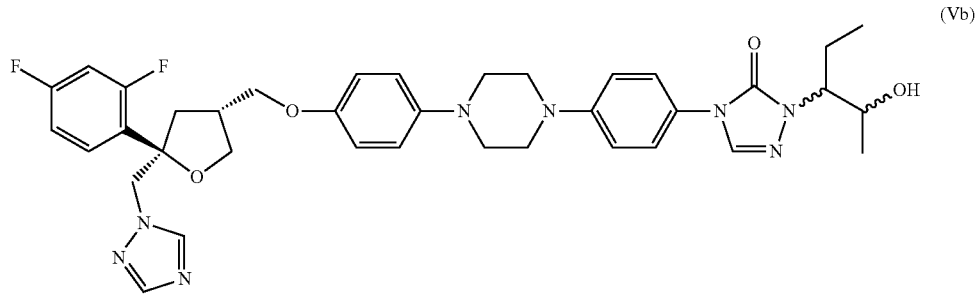 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

wherein preferably at least 95%, more preferably at least 97%, more preferably at least 99% of the molecules of said crystalline compound are present as isomer of formula (Vd)

is re-crystallized, preferably from a mixture of acetone and water, and preferably in the presence of seed crystals, said seed crystals comprising the crystalline compound of formula (Vd).

30. A mixture comprising a compound of formula (V)

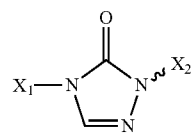
(V)

wherein $X_1$ is an optionally substituted aryl residue and $X_2$ is a linear or branched, optionally substituted alkyl residue, said mixture being directly obtained from a cyclization reaction wherein the cyclic moiety

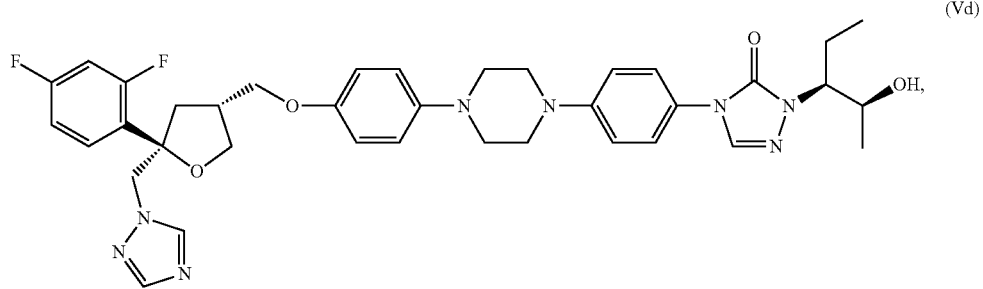 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

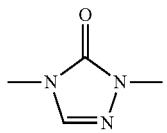

of the compound of formula (V) is formed, said directly obtained mixture comprising at least one protic solvent, preferably at least water and/or an alcohol.

31. The mixture of embodiment 30, containing
at most 5 weight-ppm, preferably at most 1 weight-ppm, said mixture in particular being free of bis-trimethylsilyl acetamide (BSA) and/or a trimethylsilyl (TMS) halide, preferably trimethylsilyl iodide (TMSI) and/or trimethylsilyl chloride (TMSCl), preferably of BSA and/or a trialkylsilyl halide, more preferably of a silylating agent; and/or
at most 5 weight-ppm, preferably at most 1 weight-ppm, said mixture in particular being free of one or more compounds selected from the group consisting of triethylamine, 1,8-diazabicyclo[5.4.0]undec-7-ene (DBU), and a phosphazene base.

32. The mixture of embodiment 30 or 31, wherein the compound of formula (V) is the compound of formula (Vf)

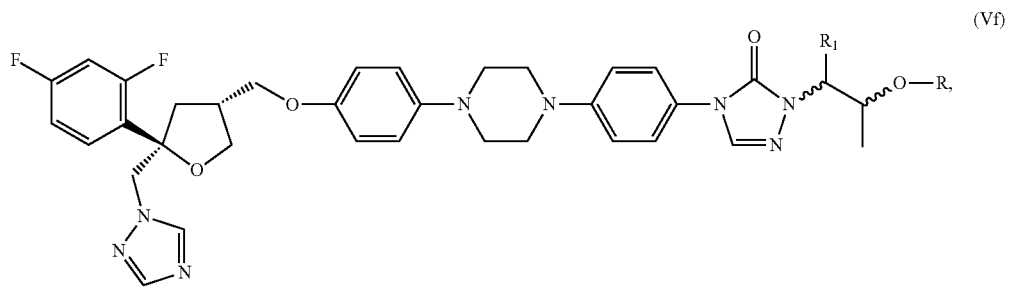

wherein R₁ is an alkyl residue preferably having from 1 to 6 carbon atoms, and
wherein —R is —H or a suitable hydroxyl protecting group preferably selected from the group consisting of —SiR$_a$R$_b$R$_c$ and optionally substituted alkyl, aryl, alkaryl or aralkyl residues, where R$_a$, R$_b$ and R$_c$ are the same or different and selected from the group consisting of optionally suitably substituted alkyl and aryl residues.

33. The mixture of embodiment 32, wherein the compound of formula (V) is the compound of formula (Vb)

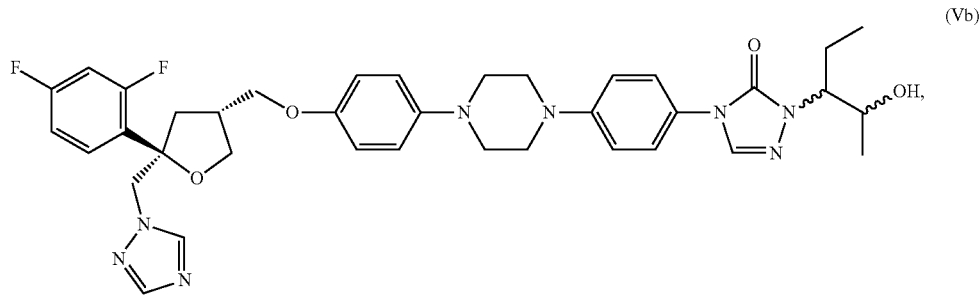 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

the mixture containing at most 0.1 area % (HPLC) of a compound of formula (IVd)

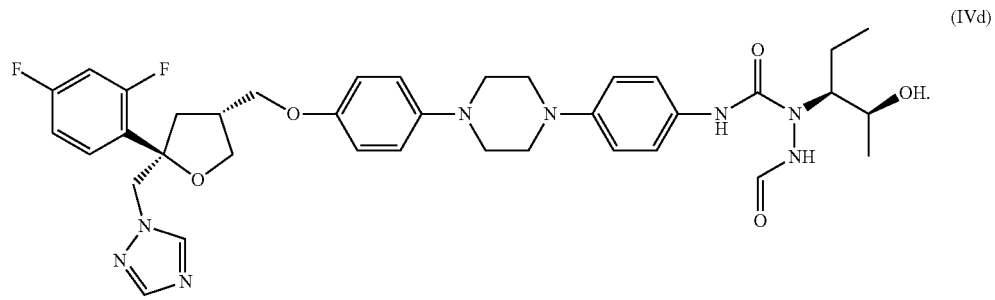 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

34. A crystalline compound of formula (Vb)

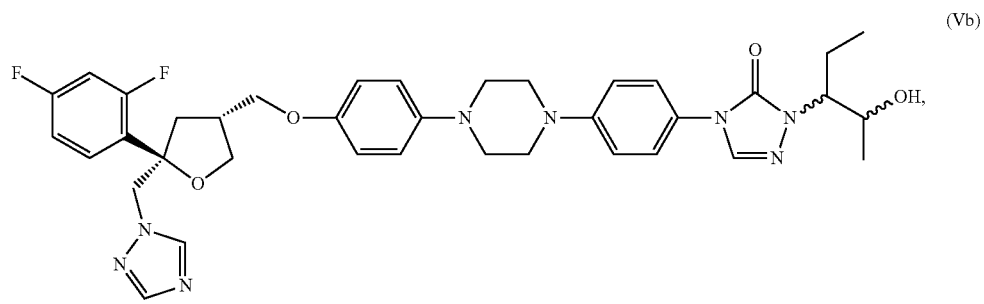 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vb)

wherein preferably at least 95%, more preferably at least 97%, more preferably at least 99% of the molecules of said crystalline compound are present as isomer of formula (Vd)

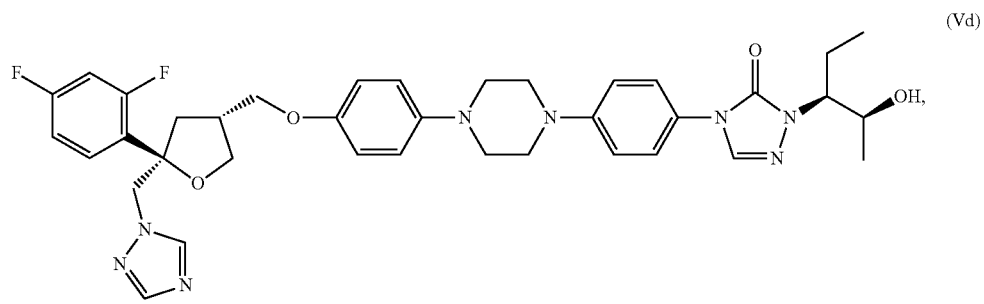 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]
(Vd)

said crystalline compound being directly obtained by the process of embodiment 21, wherein the compound of formula (IV) is a compound of formula (IVb)

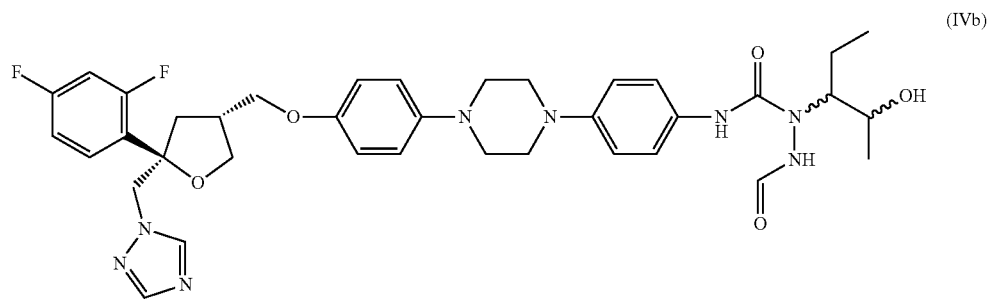 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVb)

wherein preferably at least 95%, more preferably at least 97%, more preferably at least 99% of the molecules of said compound are present as compound of formula (IVd)

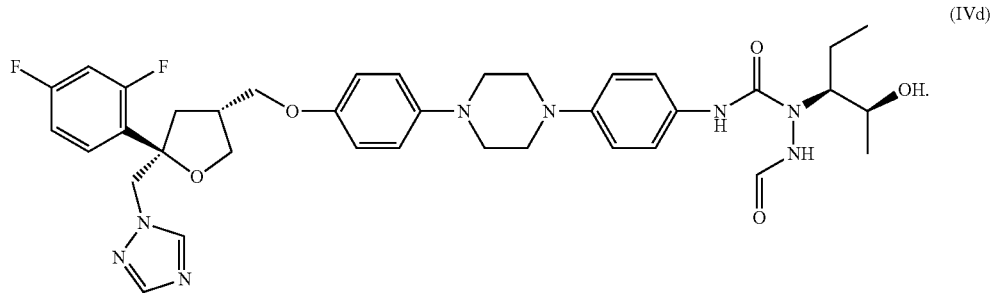 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

35. A composition comprising a preferably crystalline chiral compound of formula (Va)

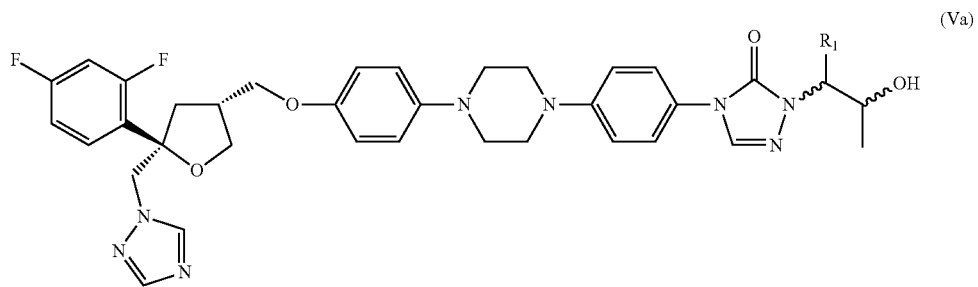

or a salt thereof, wherein $R_1$ is an alkyl residue preferably having from 1 to 6 carbon atoms, more preferably from 1 to 4 carbon atoms, more preferably 1 or 2 carbon atoms, most preferably 2 carbon atoms,
said composition preferably comprising a compound of formula (Vb)

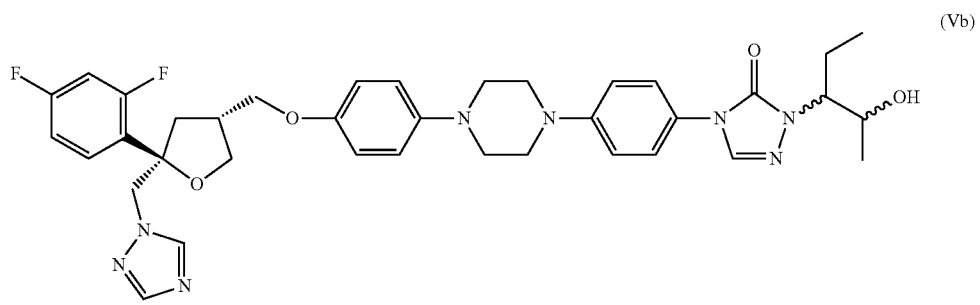 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein preferably at least 95%, more preferably at least 97%, more preferably at least 99% of the molecules of said preferably crystalline compound are present as isomer of formula (Vc)

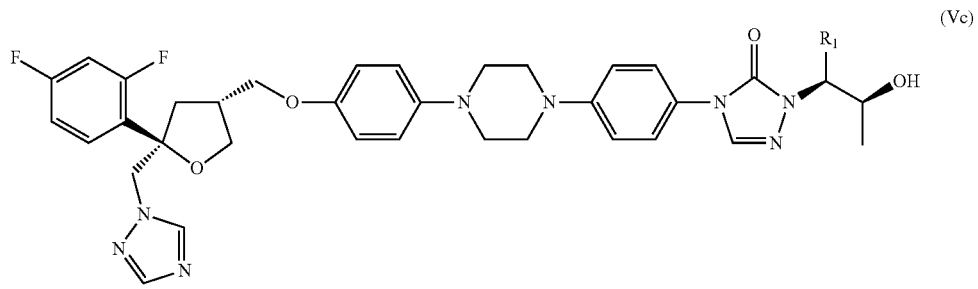

preferably as isomer of formula (Vd)

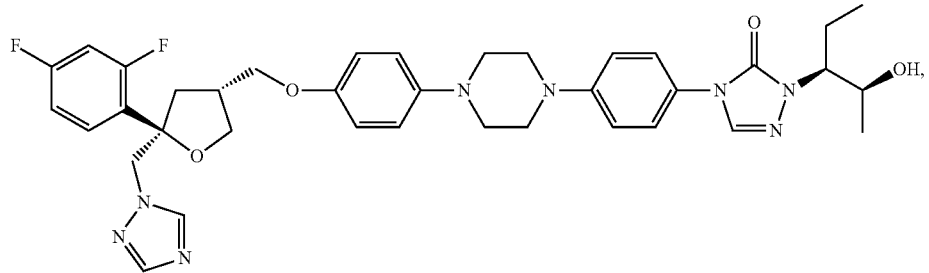

said composition containing at most 70 weight-ppm, preferably at most 50 weight-ppm, more preferably at most 30 weight-ppm, more preferably at most 10 weight-ppm, said composition in particular being free of a compound of formula (Ve)

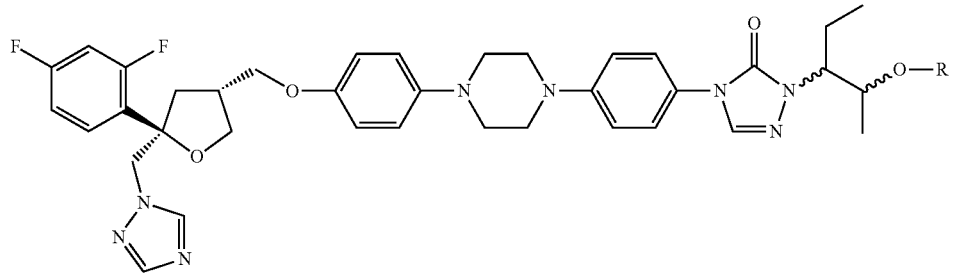

preferably a compound of formula (Vf)

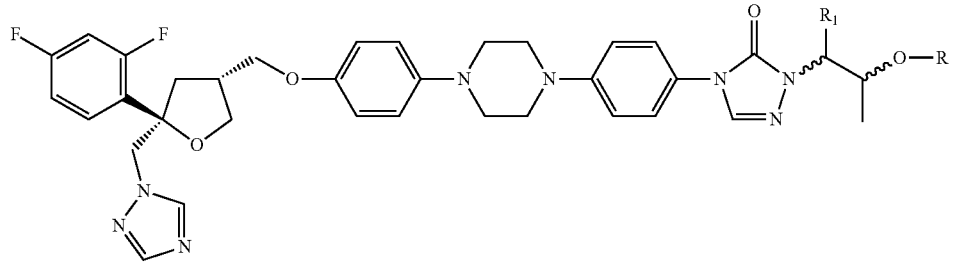

wherein —R is —$CH_2$—$C_6H_5$, —R preferably being selected from the group consisting of —$SiR_aR_bR_c$ and optionally substituted alkyl, aryl, alkaryl or aralkyl residues, where $R_a$, $R_b$ and $R_c$ are the same or different and selected from the group consisting of optionally suitably substituted alkyl and aryl residues, —R more preferably being a hydroxyl protecting group, and wherein said composition contains at most 0.1 area % (HPLC) of a compound of formula (IVd)

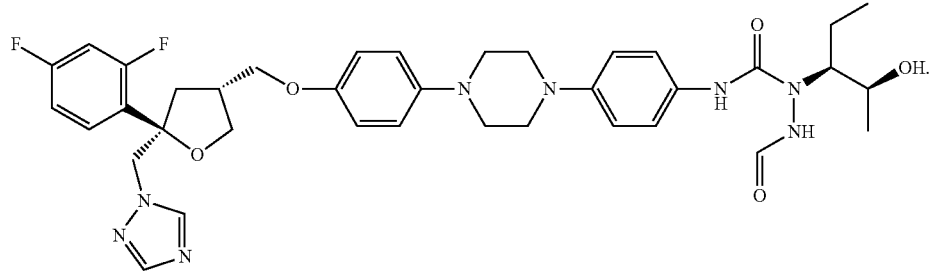

36. The composition of embodiment 35, obtainable or obtained by a process according to any one of embodiments 21 to 29.
37. A pharmaceutical composition for treating fungal infections comprising an antifungally effective amount of a composition according to embodiment 35 or 36 and a pharmaceutically acceptable additive therefor.
38. A composition according to embodiment 35 or 36 for use as a medicament.
39. A composition according to embodiment 35 or 36 for use in a method of treating or preventing fungal infections in mammals in need of such treating or preventing such infections.
40. Use of a protic solvent system, preferably comprising water and/or an alcohol, for the preparation of a compound of formula (V)

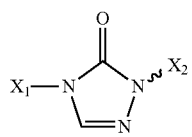

(V)

wherein $X_1$ is an optionally substituted aryl residue and $X_2$ is a linear or branched, optionally substituted alkyl residue, using a compound of formula (IV)

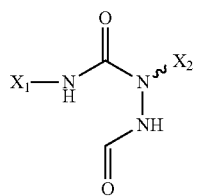

(IV)

as starting material.

The present invention is illustrated by the following examples.

EXAMPLES

Reference Example 1

Synthesis of the Starting Material, the Compound of Formula (IVb)

Reference Example 1.1

Synthesis of the Compound of Formula (B)

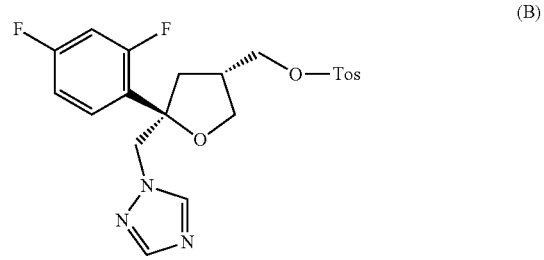

(B)

Reference Example 1.1.a

Preparation of the Compound of Formula (BB) with L=Cl

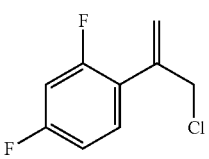

(BB)

with L = Cl

In 20 ml of MTBE, 3.8 g of Mg were suspended. The temperature of the suspension was 55° C. Then, 0.5 g of Grignard reagent (CH₃)₃Si—CH₂MgCl in MTBE from a previous batch were added in order to dry the system (if no such Grignard reagent is available for the first batch, (CH₃)₃Si—CH₂MgCl in diethyl ether (CAS Registry Number: 13170-43-9) commercially available as 1.0 M solution from Sigma-Aldrich, can be used), followed by 1.0 ml of chloromethyl trimethylsilane (CM-TMS; CAS Registry Number: 2344-80-1; commercially available from Sigma-Aldrich). Then, a solution of 14 ml of the CM-TMS in 43 ml of MTBE was added slowly over a period of 2 hours at a temperature of 55° C. The mixture was stirred for 2 hours at 55° C. and then cooled to a temperature of −10° C. Subsequently, 10.0 g of the commercial compound of formula (AA) with L=Cl (CAS Registry Number: 51336-94-8; com

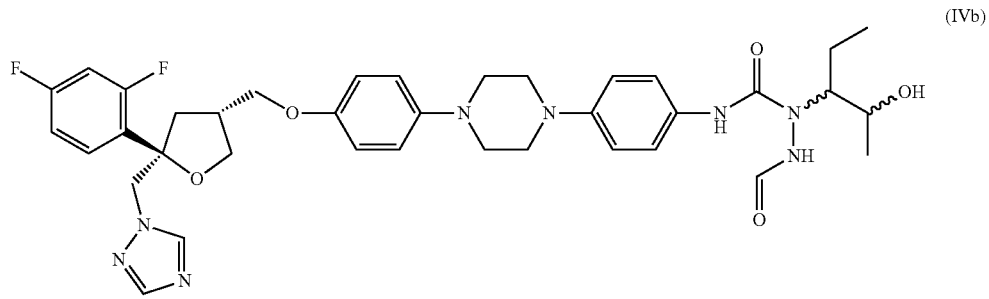 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVb)

mercially available from Sigma-Aldrich) in 30 ml of MTBE were added and the temperature was kept in the range of from 0 to −10° C. The reaction mixture was quenched in a 20% (w/v) aqueous solution of ammonium chloride. The obtained organic layer was washed with a 20% (w/v) aqueous solution of ammonium chloride. The thus washed organic layer was then washed with water.

To the organic layer, 11.0 ml of concentrated sulphuric acid were added, and the temperature was kept at 25 to 30° C. Then, the reaction mixture was stirred at a temperature of from 45 to 50° C. for 3 hours. Subsequently, the reaction mixture was cooled to 20° C. and 25 ml of water were added, and the organic layer was separated. The obtained organic layer was extracted with a 9% (w/v) aqueous solution of sodium bicarbonate, followed by washing with water. The solvents of the washed organic layer were removed by distillation under reduced pressure, and the title compound was obtained as an oil. The yield was 9.4 g, corresponding to a theoretical value of 95%.

Reference Example 1.1.b

Preparation of the Compound of Formula (CC) with $R_{11}=R_{22}=CH_2CH_3$ (Et)

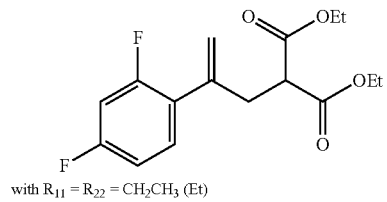

(CC)

with $R_{11} = R_{22} = CH_2CH_3$ (Et)

10.0 g of the compound of formula (BB) as oil, as obtained according to Reference Example 1.1.a, were dissolved in 20 ml of DMSO under stirring. Then, 3.2 g of NaOH flakes and 24.0 ml of diethyl malonate were added. The resulting suspension was stirred for 5 hours at 25 to 30° C. Subsequently, 100 ml of water were added, and the resulting mixture was stirred for 30 min. The thus obtained solution was extracted with 80 ml of cyclohexane at 25 to 30° C. After separation of the layers the aqueous layer was extracted with 40 ml of cyclohexane at 25 to 30° C. The combined organic layers were washed with a 5% (w/v) aqueous solution of NaOH, followed by washing with water. After washing, the solvents of the organic layer were removed by distillation under reduced pressure and the title compound was obtained as an oil. The yield was 15.0 g, corresponding to a theoretical value of 90.0%.

Reference Example 1.1.c

Preparation of the Compound of Formula (DD)

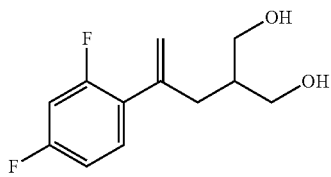

(DD)

10.0 g of the compound of formula (CC) as oil, as obtained according to Reference Example 1.1.b, were dissolved in 120 ml of isopropyl alcohol and 13.0 ml of water under stirring at 25 to 30° C. The resulting mixture was cooled to a temperature of from 0 to −5° C. Then, 2.3 g of lithium chloride and 2.1 g of sodium borohydride were added at 0 to −5° C. The resulting suspension was stirred at 25 to 30° C. for 20 hours. The pH of the stirred mixture was adjusted to a value of 1 (measured by using a calibrated pH meter) by addition of 4 N aqueous HCl. Afterwards, a 20% (w/v) aqueous solution of NaOH was added to adjust the pH to a value of 10 (measured by using a calibrated pH meter). The resulting mixture was stirred for 1 hour. Then, the lower aqueous layer was drained. From the separated organic layer, the isopropyl alcohol was distilled off, and an oil was obtained. To the oil, 100 ml of toluene and 100 ml of water were added, and the product was extracted into the toluene layer. The solvents of the resulting toluene layer were removed by distillation, under reduced pressure and the title compound was obtained as oil. The yield was 6.0 g, corresponding to a theoretical value of 82.0%.

Reference Example 1.1.d

Preparation of the Compound of Formula (EE)

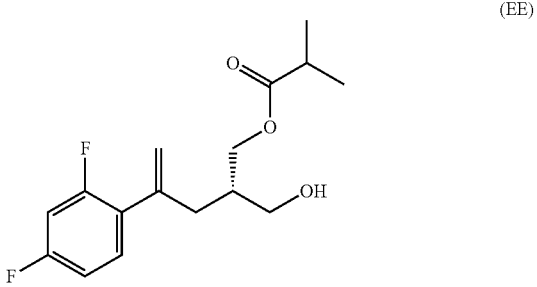 [SMILES: C=C(C[C@@H](CO)COC(=O)C(C)C)c1ccc(F)cc1F]

(EE)

10.0 g of the compound of formula (DD) as oil, as obtained according to Reference Example 1.1.c, were dissolved in 80 ml of toluene and cooled to −15° C. Then, 7.4 g of sodium bicarbonate, 0.5 g of enzyme Novo SP 435 (*Candida antarctica*, Novozym 435 from Novo Nordisk), and 7.9 ml of isobutyric anhydride were added. The resulting mixture was stirred at −15° C. for 24 hours. Then the solids were filtered off and the filtrate was washed with a 5% (w/v) aqueous solution of sodium bicarbonate, followed by washing with water. The solvents of the resulting organic layer were removed by distillation under reduced pressure to obtain the desired product as an oil. This oil was dissolved in 40 ml of n-heptane at 50 to 60° C. The clear solution was gradually cooled to a temperature of 10° C. The compound of formula (EE) crystallized as colorless crystals. The obtained solids were filtered, and the wet filter cake was washed with 20 ml of n-heptane. The filter cake was then dried at 40° C. in vacuo and the title compound was obtained as colorless crystals. The yield was 9.2 g, corresponding to a theoretical value of 70.0%.

Reference Example 1.1.e

Preparation of the Compound of Formula (FF) with Hal=I

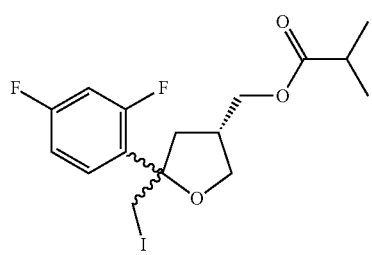
(FF)

with Hal = I 10.0 g of the crystals obtained in Reference Example 1.1.d were dissolved in 80 ml of ethyl acetate under stirring. The resulting solution was cooled to −15° C., and 21.5 g of iodine and 7.0 g of sodium bicarbonate were added. The obtained suspension was stirred at −15° C. for 5 hours. The reaction mixture was quenched in 200 ml of a 10% (w/v) aqueous solution of sodium sulphite. The organic layer was washed with 100 ml of a 10% (w/v) aqueous solution of sodium sulphite, followed by washing with water. The solvents of the thus obtained, washed organic layer were removed by distillation under reduced pressure to obtain the title compound as an oil. The yield was 13.5 g, corresponding to a theoretical value of 95.0%.

Reference Example 1.1.f

Preparation of the Compound of Formula (GG)

10.0 g of the compound of formula (FF) as oil, as obtained according to Reference Example 1.1.e, were dissolved in 80 ml of DMSO under stirring. Then, 10 g of the sodium salt of 1,2,4-triazole were added at 25 to 30° C., and the resulting reaction mixture was stirred for 24 hours at 85 to 90° C. The mixture was then cooled to 25 to 30° C., and 25 ml of 5% (w/v) aqueous solution of sodium hydroxide were added. The mixture was then stirred for 3 hours at 25 to 30° C. 100 ml of water were added, and the product was extracted into 150 ml of methyl tetrahydrofuran. The thus obtained organic layer was washed with a 10% (w/v) aqueous solution of sodium chloride, and subsequently the solvents of the resulting separated organic layer were removed by distillation under reduced pressure to obtain the title compound of formula (GG)

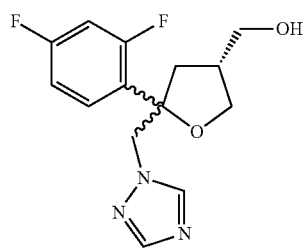
(GG)

as a crude oil. The yield was 6.0 g, corresponding to a theoretical value of 86.0%.

Reference Example 1.1.g

Preparation of the HCl Salt of Compound (GG)

10.0 g of the compound of formula (GG) as crude oil as obtained in Reference Example 1.1.f were dissolved in 200 ml of acetone under stirring at 30 to 40° C. The resulting solution was cooled to 25 to 30° C. Then, HCl in MTBE (10 wt.-%) was added over a period of 15 min at 25 to 30° C. The solid crystallized when the mixture was stirred for 15 min. Then, 200 ml of MTBE were added slowly over a period of 30 min. The suspension was cooled to 0 to −5° C. and stirred for 2 hours. The product was filtered, and the wet cake was washed with 20 ml of MTBE. After drying at 70° C. in vacuo, the HCl salt of the compound (GG) was obtained as colourless solid. The yield was 9.5 g, corresponding to a theoretical value of 85.0%.

The HCl salt of compound of formula (GG) was obtained as mixture of the cis-isomer with the respective trans-isomer with a cis:trans ratio of 9:1.

Reference Example 1.1.h

Preparation of an HCl Salt of the Compound of Formula (GG) with Solid Extraction, Using MIBK and n-Butanol as Solvent Mixture 20.0 g of the crystalline HCl salt of the compound of formula (GG) containing the HCl salt of the cis-isomer of formula (GGa)

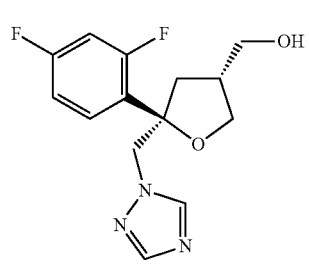
(GGa)

and the HCl salt of the trans-isomer of formula (GGb)

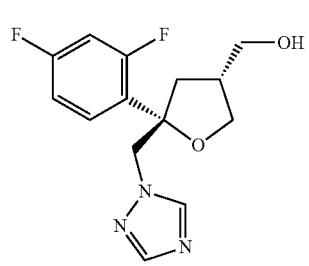
(GGb)

with a cis:trans ratio of 9:1 (60 mmol) obtained as described above in Reference Example 1.1.g were suspended in a mixture of n-butanol (50 ml) and MIBK (50 ml). The mixture was heated to 60° C., and this temperature was maintained for a period of 2 hours. Subsequently, the mixture was cooled to room temperature. The obtained solid was filtered off and washed with a small amount of diethyl ether.

This solid (14.55 g, 43.9 mmol) was re-suspended in a mixture of n-butanol (36.4 ml) and MIBK (36.4 ml). The mixture was heated to 60° C., and this temperature was maintained for a period of 2 hours. Subsequently, the mixture was cooled to room temperature. The obtained solid was filtered off and washed with a small amount of diethyl ether.

After drying under vacuum at 45° C., the HCl salt of compound of formula (GG) was obtained as colorless crystalline solid with an overall yield of 66% over 2 steps, corresponding to 10.75 g. The crystals showed bifringing under the microscope.

The HCl salt of compound of formula (GG) contained the HCl salt of the cis-isomer and the HCl salt of the trans-isomer with a cis:trans ratio of 99.2:0.8, as determined by HPLC.

HPLC Method for determination of purity and cis/trans ratio:

Scan Step Time [s] 100
Scan Type Continuous
Anode Material Cu
Generator Settings 45 kV, 40 mA
Spinning Yes
Incident Beam Optics:
Soller Slits 0.02 radians
Divergence Slit Type Programmable Slits (Fixed 0.5°)
Beam Mask 10 mm (MPD/MRD)
Diffracted Beam Optics:
Antiscatter Slit Programmable Slits (Fixed 0.5°)
Soller Slits 0.02 radians
Filter Nickel
Detector X' celerator
Mode Scanning
Active Path Length 2.122°

| Principle | Determination by HPLC using UV detector | |
|---|---|---|
| Reagents and Equipment | Potassium dihydrogen phosphate | Merck Cat. No. 60487305001730 |
| | Orthophosphoric acid (85%) | AR Grade e.g (Merck, Cat No 61768205001046) |
| | Acetonitrile | HPLC grade (e.g. Merck Cat. No. 61830025001046) |
| | HPLC system | Agilent 1100 series or similar |
| | pH meter | e.g. Metrohm or equivalent |
| Buffer Preparation | Dissolve 2.72 g of Potassium dihydrogen phosphate in 1000 ml of water and adjust the pH to 3.0 ± 0.05 by adding dilute orthophosphoric acid (85%) using a pH meter. Filter through 0.45 μm (micrometer) filter and degas. | |
| Diluent | Buffer:Methanol (80:20) v/v | |
| | Chromatographic Conditions | |
| Column | $C_{16}$, 250 mm × 4.6 mm i.d. 5μ, e.g. Ascentis RP amide or equivalent column can be used after appropriate validation. | |
| System | Gradient | |
| Column Temperature | 40° C. | |
| Mobile phase A | Buffer | |
| Mobile phase B | Buffer:Acetonitrile (30:70) v/v | |
| Flow rate | 2.0 ml/min | |
| Injection temperature | 25° C. | |
| Injection volume | 25 μl (microliter) | |
| Run time | 45 minutes | |
| Detection wavelength | 210 nm | |
| System | Gradient | |

| Gradient program | Time | % mobile phase B |
|---|---|---|
| | 0 | 20 |
| | 5 | 20 |
| | 15 | 40 |
| | 25 | 80 |
| | 28 | 90 |
| | 39 | 90 |
| | 41 | 20 |
| | 45 | 20 |

The X-ray powder diffraction pattern (XRD) of this compound of formula (GG) is shown in FIG. 3.

Method for the Recording of X-Ray Diffractograms:

The samples were analyzed on the Zero background holder in spinning mode at ambient conditions. A typical precision of the 2-Theta values is in the range of about ±0.2° 2-Theta. Thus a diffraction peak that appears at 8.6° 2-Theta can appear between 8.4 and 8.8° 2-Theta on most X-ray diffractometers under standard conditions.

Instrument Parameters:
XRD Measurement Conditions:
Instrument X'PERT PRO PANalytical
Scan Axis Gonio
Start Position [° 2Th.] 3.0
End Position [° 2Th.] 40.0
Step Size [°] 0.0170

Reference Example 1.1.j

Synthesis of the Compound of Formula (B)

A suspension of 292.0 g of the compound of formula (GG) obtained according to Reference Example 1.1.h above (MW: 331.75 g/mol; 0.88 mol, d. r.>99:1; 1.0 equiv.) in 2.92 l of $CH_2Cl_2$ was prepared at a mass temperature of 12±3° C. To this, 142.5 g of $Et_3N$ (MW: 101.19 g/mol, 195.9 ml, 1.41 mol, 1.6 equiv.) were added slowly at 22±8° C. within 60 min. The mixture was cooled to a mass temperature of 12±3° C. and 129.5 g of DMAP (4-dimethylamino-pyridine; MW: 122.17 g/mol; 1.06 mol, 1.2 equiv.) were added in one portion. Subsequently, 185.0 g of TsCl (tosyl chloride; MW: 190.65 g/mol; 0.97 mol; 1.1 equiv.) were added in at least five portions at a mass temperature of 22±8° C. within 60 min. By the last addition, the mass temperature was adjusted to 25±3° C. and stirring of the pink suspension was continued for further 3 h at 25±3° C. The reaction mixture was extracted with 1.46 l of aq. 10% HCl at 25±3° C. followed by 1.46 l of aq. 9% NaHCO₃ at 25±3° C. followed by 1.46 l of H₂O. The organic layer was concentrated to approx. 20% of its original volume at 25±3° C. under reduced pressure. To the concentrate, 5.83 l of heptane (25±3° C.) were added slowly at 25±3° C. within 60 min. The resulting suspension was cooled to 2±3° C. and stirring was continued for 60 min. The solid was filtered off and washed with 2×1.46 l of heptane (25±3° C.). The product was dried under reduced pressure (<50 mbar) at 40° C. over night until a level of ≤0.1% of DCM was achieved.

372.8 g of the compound of formula (B) (0.83 mol, 94% yield "as is") were obtained.

The product contained the compound of formula (B), the cis-isomer

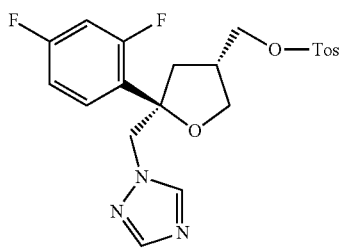

(B)

and the trans-isomer

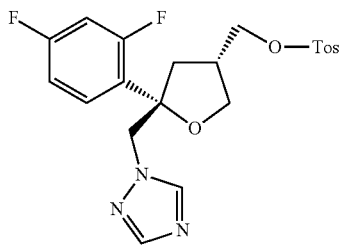

with a cis:trans ratio of 99.2:0.8.

Reference Example 1.2

Synthesis of the Compound of Formula (Ia)

A solution of 297 mg of BHT (butylated hydroxytoluene; M=220.35 g/mol; 1.35 mmol; 500 ppm) and 727 g of the compound of formula (A)

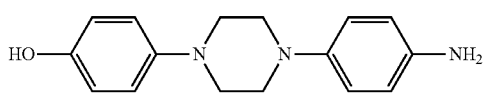

(A)

(MW: 269.35 g/mol; 2.698 mol; 1.0 equiv.; obtainable, for example, according to example 1 of EP 1 230 231 B1 (on page 4)) in 4.7 l of DMSO was prepared at a mass temperature of 30±2° C. To this was added a solution (30±2° C.) of 161.9 g of NaOH (MW: 40.0 g/mol, 4.047 mol, 1.5 equiv.) in 161.9 g of oxygen-free H₂O upon keeping the mass temperature at ≤32° C. The mixture was stirred for 10 min at 30±2° C. Then, a solution (30±2° C.) of 1335 g of the compound of formula (B) contained in the product as obtained according to Reference Example 1.1 (Reference Example 1.1.j) above

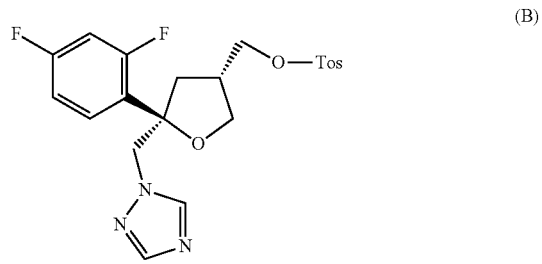

(B)

(12.968 mol=1.1 equiv., MW=449.48 g/mol) in 6.6 l of DMSO was added at a mass temperature of ≤32° C. within 10 min. The pH of the reaction mixture was checked after a reaction time of 60 min and at least also after 5 and 8 hours. After stirring for 60 to 90 min at 30±2° C. the crystallization of the product started. The dark brownish, thin suspension was stirred for 10-15 h at 30±2° C. At minimum agitation rate, the addition of 21.8 l of H₂O was started at 30±2° C. and was carried out at a constant rate whereby the reaction temperature was allowed to rise simultaneously to 45±5° C. Then, the remaining water was added at a rate to keep the temperature at 45±5° C. (overall addition time: about 60 min in total). Subsequently, the suspension was cooled to 20±2° C. in 60 min and stirred for further 60 min at 20±2° C. The resulting solid was filtered off and washed with 8.5 l of cold 1% oxygen-free aqueous NaOH (5-10° C.), then 2×8.5 l of cold oxygen-free H₂O (15-10° C.) followed by 2×8.5 l of isopropanol (22±3° C.).

All operations being part of the following purification procedure were carried out under a positive nitrogen atmosphere.

The wet crude product (approx. 2.44 kg) in 72.7 l of acetonitrile was heated to reflux temperature. The mixture was refluxed for 10-15 minutes. To the resulting solution 116 g of charcoal (Ceca Eno) were added and the suspension was stirred for 10 min at reflux temperature. The charcoal was filtered off and the filter cake was washed with 11.6 l of hot acetonitrile. Under stirring the yellow coloured filtrate was cooled to 20±2° C. during 1 hour. Crystallization started at approx. 60° C. Under stirring the crystal suspension was cooled to 0±2° C. over 30 min and stirred at this temperature for one hour. The resulting crystals were filtered off and washed with 6 l of cold acetonitrile (≤5° C.).

The product was dried at ≤75° C. (preferred temperature 70±5° C.) under reduced pressure (≤55 mbar) until a level of ≤1.4% of residual water was achieved. 1180 g of the compound of formula (Ia)

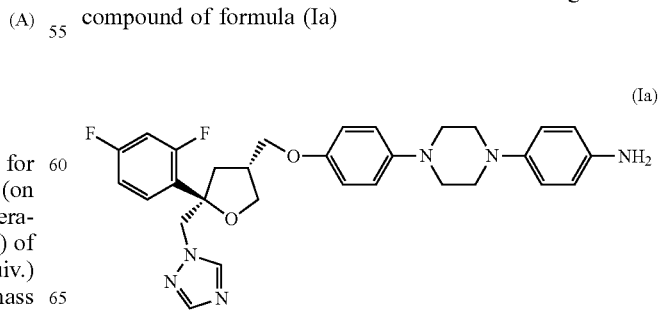

(Ia)

(MW: 546.63 g/mol; 2.18 mol, 80.0% yield "as is") were obtained as a white to yellow crystalline powder.

Reference Example 1.3

Synthesis of the Compound of Formula (IIIa)

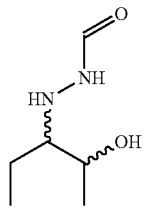

(IIIa)

Reference Example 1.3.1

Synthesis of the Compound of Formula (II) with Y=Phenyl a) 1.70 kg of nitrosobenzene (MW: 107.11; 15.9 mol; 1.0 eq.) were dissolved in 6.16 l of DCM by stirring at 20-25° C. under $N_2$ atmosphere.
b) In a separate vessel, 2.76 kg propionaldehyde (MW: 58.08; density: 0.798 g/ml; 47.5 mol; 3.0 eq.) and 5.28 l of DCM were cooled to −6 to −4° C. under $N_2$ atmosphere. To the resulting mixture, 0.057 kg of glacial acetic acid (MW: 60.05; density: 1.049 g/ml; 0.95 mol; 0.06 eq.) and 0.55 kg of D-proline (MW: 115.13; 4.75 mol; 0.3 eq.) were added, and a fine suspension was obtained.
c) To this suspension of b), 0.4 l of the nitrosobenzene solution obtained in a) were added. Onset of the reaction was indicated by discoloration of the suspension and a temperature rise up to +3° C. within 1 min. Then, the remaining nitrosobenzene solution (about 7 l) of the nitrosobenzene solution obtained in a) were added at a rate to keep the reaction temperature between −5 and −3° C. The mixture gradually turned darker and resulted in a clear solution when addition was complete. Stirring was then continued for 10 min, and complete conversion was determined using HPLC. The compound of formula (i) with Y=phenyl was obtained as intermediate with an enantiomeric purity expressed as enantiomeric excess (ee)>98%, i.e. more than 99% of the molecules of the chiral compound of formula (i) with Y=phenyl were present as isomer of formula (Ia) with Y=phenyl. Enantiomeric purity was determined analogously to the method described in Brown et al., *J. Chem. Soc.* 2003, 125 (36), 10808-10809 and using Chiralcel™ OD-H and n-heptane/isopropanol/diethylamine as eluent.
d) Subsequently, 8.8 l of DCM, 3.0 kg of a molecular sieve having pores with a diameter of 0.4 nm (4 Angstrom; commercially available from Aldrich), and 3.14 kg of formyl hydrazine (MW: 60.06; 52 mol; 3.3 eq.) were added at 0-5° C., leading to an increase in temperature. Stirring was continued at 0-5° C. under $N_2$ atmosphere. After 3 hours, complete conversion was determined using HPLC.
e) The obtained solids were filtered and washed with 4.4 l of DCM. The solution was concentrated to ¼ of its original volume at a bath temperature of <10° C. Then, 28 l of MTBE were added, and the resulting solution was reduced to ¼ of its original volume by distillation at a bath temperature of <10° C. The resulting organic layer was then diluted with 7 l of MTBE and extracted five times with 28 l of a 20% aqueous sodium chloride solution. Then, 8.8 l of DCM were added for azeotropic removal of water. The resulting solution was concentrated to give 12 kg of a solution of the compound of formula (ii) with Y=phenyl in MTBE which contained 2.86 kg of said compound (MW 207.23; 80% yield).
f) This solution containing the compound of formula (ii) with Y=phenyl was used in the next step (Reference Example 1.3.2) without further purification.

Reference Example 1.3.2

Synthesis of the Compounds of Formula (iii) and (iv) with Y=phenyl, and $R_{aa}$, $R_{bb}$ and $R_{cc}$=methyl and $R_1$=ethyl a) 0.887 kg of the compound of formula (ii) as obtained according to Reference Example 1.3.1 (MW: 207.23; 4.28 mol; 1.0 eq.), employed as a solution in MTBE (total weight 290 g) which contained about 2 wt.-% of $H_2O$, were dried with 1.54 kg of a molecular sieve having pores with a pore diameter of 0.4 nm (4 Angstrom; commercially available from Aldrich) at 20-25° C. for 30 min. Thus, the water content was reduced to a value of less than 0.1 wt.-%. Then, the molecular sieve was removed by filtration and washed with 1.7 l of MTBE. The resulting solution was diluted with 16 l of MTBE. The water content of this solution was about 0.05% (0.5 mol; 0.12 eq.).
b) Then, 2.8 l of BSA (bis-trimethylsilyl acetamide) (MW: 203.43; density: 0.832 g/ml; 11.5 mol; 2.7 eq.) were added to the filtrate. The resulting solution was stirred at 20-25° C. After 1 hour, silylation was complete, as detected by $^1$H-NMR. The compound of formula (iii) with Y=phenyl and $R_{aa}R_{bb}$ and $R_{cc}$=methyl was obtained as intermediate.
c) Then, the solution was cooled to −70 to −60° C., and 8.65 l of a solution of ethyl magnesium chloride in THF (2 mol/l; MW: 88.82; density: 0.978 g/ml; 17.3 mol; 4.0 eq.) were added at a rate to keep the reaction temperature between −70 and −60° C. This mixture was stirred for 1 hour at −60° C. Subsequently, the temperature was raised to −25° C., and stirring was continued. After 3 hours, complete conversion was detected by HPLC. The reaction was then quenched by dropwise addition of 5.5 kg of MeOH at a temperature of −25° C. During quenching, the mixture was allowed to warm up to 0-15° C.
d) The resulting organic layer was then extracted at 20-25° C. twice with 30 l of a 10% aqueous ammonium chloride solution and once with 30 l of a 20% aqueous sodium chloride solution. The organic layer (20 kg) contained approximately 0.89 kg of the compound of formula (Iv) with Y=phenyl and $R_1$=ethyl (MW: 237.30; 80% yield) and was used for the next step (Reference Example 1.3.3) without further purification.

Reference Example 1.3.3

Synthesis of the Compound of Formula (III) with R=H and $R_1$=ethyl, i.e. the compound of formula (IIIa)

a) 0.89 kg of the compound of formula (iv) (MW: 237.30; 3.76 mol; 1.0 eq.), obtained according to Reference Example 1.3.2 and used as a solution in MTBE (total weight 20 kg) was diluted with 1 l of MeOH at 20-25° C.
b) Then, 0.9 kg of palladium on carbon (Pd/C; 5% Pd; 50% water) were added, and the resulting solution was stirred vigorously at 20-25° C. Reduction reaction was carried out with 1 atm of $H_2$. The vessel was evacuated and vented with 1 atm $H_2$ three times. After 1.5 hours of stirring under $H_2$ atmosphere, complete conversion was detected by HPLC. Then, the suspension was filtrated and the catalyst washed with 1.8 l of MTBE/MeOH (1/1 v/v). The combined filtrates were concentrated to a yellow oil to yield the crude compound of formula (IIIa), containing about 40% (about 0.55 kg) of the compound of formula (IIIa).
c) This oil was diluted with 13.9 l of MTBE at 20-25° C., and the resulting solution was seeded. After 1 hour of stirring at 20-25° C., a fine suspension was obtained. Then, 17 l of CHX (cyclohexane) were added, the mixture was cooled to 0° C. and stirred at 0° C. for 3 hours, resulting in a thick suspension of the compound of formula (IIIa). The thus obtained crystals were collected and washed with 2.2 l of a cold (0° C.) mixture of MTBE and CHX (1/1 v/v) to give 0.44 kg of the compound of formula (IIIa) after drying (MW 146.19; 80% yield; 64% yield with respect to the compound of formula (ii)). More than 99% of the molecules of the chiral compound of formula (IIIa) were obtained as isomer according to formula (IIIb). 10.4 g of this yellow colored material were added to 50 ml of isopropyl acetate, and the resulting mixture was heated to a temperature of 85 to 89° C. until a solution was obtained. 0.5 g of activated carbon were added to the yellow solution, and after stirring for several minutes, the hot mixture was filtered and allowed to cool to about 5° C. under stirring. After stirring for 2 to 3 hours, the precipitated product was filtered, washed with 5 ml of isopropyl acetate and dried at room temperature under vacuum over night to give 8.54 g of the product as a off-white solid (melting point 78 to 80° C.), i.e. the compound of formula (IIIa), wherein more than 99% of the molecules of said compound were obtained as isomer according to formula (IIIb).

Preparation of seeds used in this step c):
100 g of the crude oil obtained in step b) above were purified by column chromatography using 800 g silica gel 60 (0.063-0.200 mm, Merck) as stationary phase and DCM/methanol=20/1 as mobile phase. The fractions containing the desired product in pure form, as determined by TLC (Merck, silica gel 60 $F_{254}$, mobile phase CHX/ethyl acetate=1/1), were collected. After evaporation of the solvents the obtained solid was recrystallized from diethyl ether. The resulting crystals were collected and used as seeds after drying (20° C., <100 mbar).

d) The IR spectrum and the X-ray diffractogram are shown in FIGS. 1 and 2.

Experimental data were obtained as follows:
The enantiomeric purity of the compound of formula (IIIa) as obtained in c) was measured by HPLC as follows:
Chromatography
HPLC apparatus: Agilent 1200
Column: Waters XBridge C18, 2.5 µm, 50×4.6 mm (order no. 186003090)
System: gradient
Eluent A: buffer solution pH 7.0
Eluent B: buffer solution pH 7.0/acetonitrile=2/8 (v/v)
Flow rate: 1.8 ml/min
Oven temperature: 40° C.
Injection volume: 10 µl (microliter)
Stop time: 20 min
Detection: λ (lambda)=260 nm
Gradient:

| t (min) | | | | | |
|---|---|---|---|---|---|
| 0 | 8 | 12 | 14 | 15 | 20 |
| % B | | | | | |
| 10 | 20 | 100 | 100 | 10 | 10 |

Buffer solution pH 7.0 prepared according to the following recipe: dissolve 7.0 ml of triethylamine in 900 ml of water, adjust the pH to 7.0 with $H_3PO_4$ and dilute to 1000 ml with water.

Reagent solution prepared according to the following recipe: dissolve 80 to 90 mg of (S)-(−)-α-methylbenzyl isocyanate in acetonitrile and dilute to 1.0 ml with acetonitrile.

Sample Preparation:
a) Test Stock Solution Prepared According to the Following Recipe:
Dissolve 38 to 42 mg of the substance to be tested, weighed accurately to 0.01 mg, in 1.0 ml of acetonitrile.
b) Test Solution Prepared According to the Following Recipe:
In an HPLC vial, mix 100 µl (microliter) of test stock solution and 100 µl (microliter) of reagent solution. Keep at room temperature (20 to 25° C.) for 30 min, add 800 µl (microliter) of buffer solution pH 7.0 and shake well. Then cool the solution on an ice bath (0° C.) for additional 30 min (precipitation of reagent) and filtrate a sample through 0.2 µm (micrometer) directly into another HPLC vial.

Infrared spectra (IR) data were collected on a MKII Golden Gate™ Single Reflection Diamond ATR (attenuated total reflection) cell with a Bruker Tensor 27 FTIR spectrometer with 4 $cm^{-1}$ resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 $cm^{-1}$. Thus, an infrared peak that appears at 1716 $cm^{-1}$ can appear between 1714 and 1718 $cm^{-1}$ on most infrared spectrometers under standard conditions.

X-ray data (powder diffraction pattern XRPD, X-ray diffraction pattern XRD, X-ray diffractogram) were collected on a Unisantis XMD 300 X-ray powder diffractometer with a position sensitive detector in parallel beam optics using the following acquisition conditions: tube anode: Cu, 40 kV, 0.8 mA; 3-43° theta/2theta; simultaneous detection of regions of 10° per step with detector resolution 1024, counting time 300 seconds per step. Samples were measured at room temperature in a standard sample holder on a rotating sample spinner. A typical precision of the 2-theta values is in the range of ±about 0.2° 2-Theta. Thus a diffraction peak that appears at 5.0° 2-Theta can appear between 4.8 and 5.2° 2-Theta on most X-ray diffractometers under standard conditions.

HPLC for determination of completion of conversion as mentioned in Reference Example 1.3.1, c) and d), Reference Example 1.3.2, c) and Reference Example 1.3.3, b) was performed as follows:

Column: Zorbax Eclipse XDB-C18, 150*4.6 mm, 5 μm (micrometer).
System: gradient
Buffer: 2.10 g $KH_2PO_4$+4.28 g $K_2HPO_4$/2.0 l $H_2O$, adjust with 85% $H_3PO_4$ to pH 6.5
Mobile phase A: 20 mM phosphate buffer pH 6.5/acetonitrile, 85/15, v/v
Mobile phase B: 20 mM phosphate buffer pH 6.5/acetonitrile, 50/50, v/v
Solvent: $H_2O$/acetonitrile=50/50 v/v
Flow rate: 1.5 ml/min
Oven temperature: 60° C.
Injection volume: 5-20 μl (microliter)
Stop time: 30 min
Detection: λ (lambda)=210 nm (Agilent 1200 detector)
Autosampler: 5° C.
Gradient:

| t [min] | 0 | 20 | 25 | 26 | 30 |
|---|---|---|---|---|---|
| % B | 5 | 100 | 100 | 5 | stop |

Sample Preparation:

Sample solution for HPLC in Reference Example 1.3.1, c) was prepared according to the following recipe: dissolve approx. 100 μl (microliter) of the reaction mixture in 0.2 ml of isopropanol, add approx. 50 mg of $NaBH_4$ and agitate for 10 min at 25° C. Extract with 0.2 ml of ethyl acetate and 0.5 ml of a 5% $KH_2PO_4$ buffer (pH 7.0). Dilute 50 μl (microliter) of the resulting organic layer in a 10 ml volumetric flask and fill to the mark with solvent. Sample weights are adapted according to instrument requirements.

Sample solution for HPLC for Reference Example 1.3.1, d), Reference Example 1.3.2, c) and Reference Example 1.3.3, b) was prepared according to the following recipe: dissolve approx. 100 μl of the reaction mixture in 2 ml of acetonitrile in a 20 ml volumetric flask and fill to the mark with solvent. Sample weights are adapted according to instrument requirements.

Reference Example 1.4

Synthesis of the Compound of Formula (IVb)

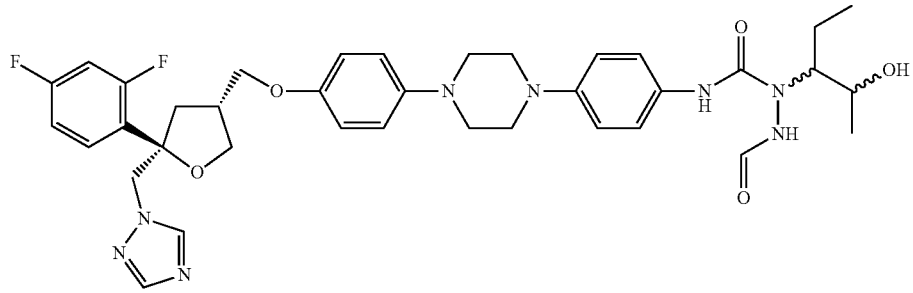 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

32.63 g carbonyldiimidazole (compound of formula (IIc), 1.1 eq, 201.2 mmol, Sinochem Jiangsu #090506) were dissolved under nitrogen atmosphere in 1300 ml DCM in a 2.0 l Schmizo reactor and cooled to −10° C. under permanent stirring.

Afterwards 100.0 g of the compound of formula (Ia) obtained according to Reference Example 1.2 (1 eq., 182.9 mmol) were added and rinsed in with additional 300 ml DCM. The reaction mixture was stirred at −10° C. for 2 hours.

Subsequently, 30.76 g of the compound of formula (IIIa) as obtained in Reference Example 1.3 (1.1 eq, 201.23 mmol) were added and rinsed with 300 ml DCM. The reaction mixture was warmed to 30° C. and afterwards stirred for 3 hours at this temperature.

Afterwards the reaction mixture was cooled to 25° C. and the mixture was stirred at this temperature for 4 hours. Crystallization occurred after 2.5 hours. The suspension then was cooled to 0° C. and stirred for additional 15 hours at this temperature. The solid was isolated via vacuum filtration (time: about 15 min) and afterwards, the filtercake was washed two times each with 100 ml of ice cold DCM. The filtercake was dried (20-25° C., <50 mbar) and afterwards, 129.2 g of the compound of formula (IVb) were isolated as a 1/1/1 crystallisate with imidazole and DCM (>98.5 area % of the compound of formula (IVb) excluding imidazole, determined by HPLC as described below; yield: 81.5%). The ratio of the compound of formula (IVb) to imidazole and to DCM was detected via NMR.

At least 99% of the molecules of the compound of formula (IVb) were obtained as isomer of formula (IVd)

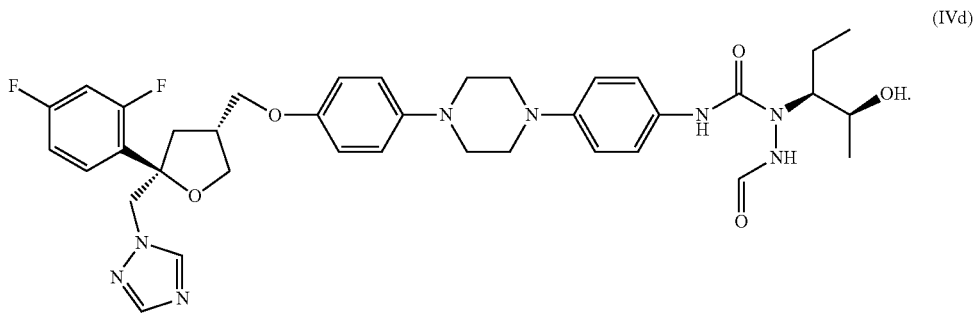 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

(IVd)

The IR spectrum and X-ray diffractogram of the obtained compound of formula (IVb) are shown in FIGS. 4 and 5.

Infrared spectra (IR) data and X-ray data (powder diffraction pattern XRPD) were determined according to the methods as described in Reference Example 1.3.

$^1$H-NMR and $^{13}$C-NMR spectra of the obtained compound of formula (IVb) as obtained in Reference Example 1.4 were collected. The following results were obtained:

$^1$H-NMR (CDCl$_3$, 300 mHz):
delta (ppm)=0.93-1.02 (m, 3 H), 1.26 (m, 3 H), 1.45 (m, 1 H), 2.06 (m, 2 H), 3.22 (m, 8 H), 3.52-3.80 (m, 4 H), 4.11 (m, 1 H), 4.52 (d, J=16 Hz, 1 H), 4.64 (d, J=16 Hz, 1 H), 5.30 (s, DCM), 6.74-6.93 (m, 8 H), 7.09 (s, 2 H), 7.29-7.39 (m, 3 H), 7.67 (s, 1 H), 7.79 (s, 1 H), 8.14 (s, 1H), 8.22 (b, 1.5 H), 9.53 (b, 0.5 H) rotamers.

$^{13}$C-NMR (CDCl$_3$, 75 mHz):
delta (ppm)=10.9, 19.7, 21.5, 37.4, 38.8, 49.9, 50.6, 55.9, 67.2, 68.9, 70.7, 84.0, 104.6 (t), 111.4 (q), 115.0, 116.9, 118.3, 122.0, 125.4 (q), 128.5 (q), 130.5, 131.1, 144.5, 145.8, 148.8, 149.0, 151.0, 152.8, 156.4, 157.4 (t), 160.7 (q), 164.3, 164.5.

HPLC Method for determination of purity of the obtained compound of formula (IVb):
Column: Zorbax Eclipse XDE-C18, Rapid Res., 4.6×50 mm, 1.8 μm,
flow: 1.5 ml/min
wavelength: 210 nm
Auto sampler: 5° C.
oven temperature: 55° C.
Eluent A: 20 mM Phosphate buffer pH 6.5/acetonitrile 85/14 (v/v)
Eluent B: 20 mM Phosphate buffer pH 6.5/acetonitrile 25/75 (v/v)
Gradient: 0 min/29% B, 10 min/55% B, 12 min/100% B, 15 min/100% B, 15.1 min/29% B, 17 min stop
Sample Preparation:

The sample (7-10 mg) was dissolved in a 1/1 mixture of acetonitrile and water, and in case of slow dilution ultra sonic bath was used to gain complete dilution.

Reference Example 2

General Procedure for the Preparation of the Seed Crystal Material Employed in Examples 1 and 2 (Synthesis of the Compound of Formula (Vb))

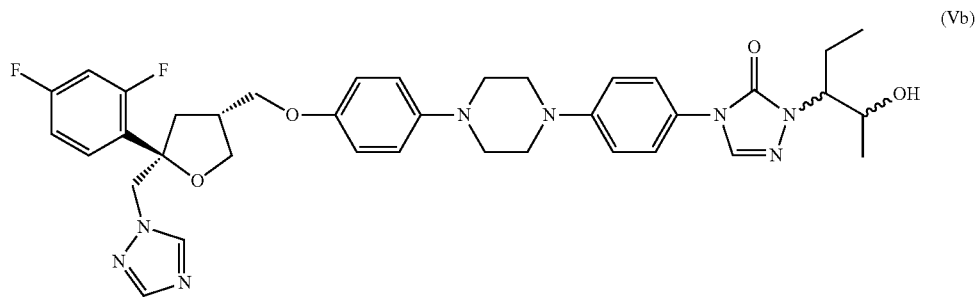 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

(Vb)

50.0 g of the compound of formula (IVb) as obtained according to Reference Example 1.4 above (1 eq, 57.39 mmol) were dissolved in 1600 ml isopropylacetate. To the suspension, 18.66 g imidazole (5.8 eq in total with the imidazole contained in the starting material, 332.8 mmol) and 20.83 g BSA (1.78 eq, 102.4 mmol, 25.0 ml) were added and the mixture was stirred for 45 min until a clear solution occurred. Afterwards 4.30 g of TMSI solution in DCM containing 2.56 g TMSI (0.22 eq, 12.78 mmol) were added, and the reaction mixture was heated to reflux (89° C.) and stirred at that temperature for 19 hours until complete conversion of the compound of formula (IVb) was observed. The reaction mixture was added dropwise at a temperature between 50-60° C. to 500 ml 10% HCl. The aqueous phase was separated, and 750 ml DCM were added. Afterwards the pH of the mixture was adjusted to 1.02 by the addition of about 225 ml of 20% NaOH solution. The organic phase was separated and washed with 500 ml 0.1 M HCl followed by a washing with 330 ml 5% sodium bicarbonate solution. Afterwards the organic solvent was removed under reduced pressure (40° C., 600-20 mbar) leading to 50.71 g of compound of formula (Vb) as a white solid. The solid was dissolved in acetone and afterwards 325 ml water were added. To the solution 10 g charcoal (Ceca Eno) were added and the mixture was stirred for 30 min. Afterwards the charcoal was removed via filtration, the filter cake was washed with 300 ml of an acetone/water (5/1) mixture leading to a slightly yellow solution. The solution was warmed to 27° C. and 1000 ml water were added. Subsequently 40 mg seeding crystals (obtained according to above-described process followed by purification by chromatography) were added and the mixture was stirred for 60 min leading to white slurry. Additional 500 ml water were added and the mixture was stirred at 30° C. for 30 min, cooled to 15° C. and stirred at that temperature for 120 min. Afterwards the white solid was separated via filtration (G3, d=12 cm) and the filter cake was washed with 375 ml of an acetone/water (1/2) mixture. The isolated solid was dried under vacuum (<45 mbar) at 40° C. for 16 hours leading to 32.57 g of the compound of formula (Vb) (46.48 mmol, 81.0%, contents 98.9%).

At least 99% of the molecules of the compound of formula (Vb) were obtained as isomer of formula (Vd)

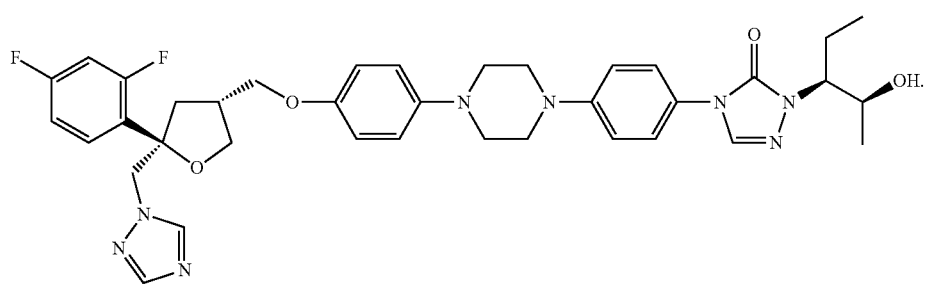

(Vd)

HPLC Method for determination of the ratio of Vd to Vb:
Column: Daicel CHIRALCEL OD, 250×4.6 mm
System: isocratic
Eluent:Hexane/Ethanol/Diethylamine=30/70/0.2 (v/v/v)
Flow rate: 1.0 ml/min
Oven temperature: 39° C.
Injection volume: 15 μl
Stop time: 20 min
Detection: λ (lambda)=260 nm (Agilent 1100 detector)
Autosampler: 39° C.
Solutions Prepared According to the Following Recipe:

Dissolve 24 to 27 mg of the substance to be tested, weighed accurately to 0.01 mg, in solvent in a 25-ml volumetric flask. Fill to the mark with solvent and shake well.

Example 1

Synthesis of Posaconazole in a Protic Solvent System Water/Isopropanol with Sodium Hydroxide as Base 20.0 g (22.97 mmol) of compound (IVb) as a 1/1/1 crystallisate with DCM (dichloromethane) and imidazole as obtained from Reference Example 1.4 were dissolved in 156 ml isopropanol, and 55 ml of water were added. Subsequently, 0.92 g sodium hydroxide (1.0 eq., 22.95 mmol) were added. The reaction mixture was heated under reflux (80° C.) for 16.5 h until not more than 0.1 area % starting material was detected via HPLC analysis (HPLC method see Reference Example 1.4). The reaction mixture was then cooled to 50° C. and at this temperature, 620 ml acetone, 141 ml water and 8 ml 10% aqueous HCl (1 equivalent, 22.95 mmol) were added. The mixture was cooled to 13° C., and a pH of 5.3 was observed. Subsequently, 0.2 g seeding crystals (obtained according to the method of Reference Example 2) were added. The mixture was stirred at 13° C. for 60 min and then cooled to 10° C. over a period of 15 min. Afterwards, the obtained suspension was stirred for 60 min at 10° C. Then, 228 ml of a 1/1 mixture of acetone and water (v/v) was added over a period of 75 min. After complete addition, the mixture was stirred for 60 min at 10° C. To the suspension, 568 ml water were added over a period of 45 min. The suspension was stirred for 60 min at 10° C. Afterwards, the solid was isolated via filtration. The filter cake was washed twice with 50 ml of a cold (10° C.) 1/2 acetone/water mixture. The isolated solid was dried for 16 h at 40° C. leading to 14.5 g posaconazole in a crystalline form (yield approximately 90%). The solid was dissolved in 179 ml 10% aqueous HCl and heated to 60° C. for 2.5 h. After cooling to 20-25° C., 278 ml DCM were added and afterwards, the pH was adjusted to a value of 1.02 by addition of about 110.4 g 20% aqueous NaOH. The phases were separated and the organic phase was washed with 179 ml 0.1 M aqueous HCl and 126 ml 5% aqueous NaHCO₃ solution. The organic solvent was removed using a rotavapor (40° C., 600 to <40 mbar) and the residue was dissolved in 415 ml acetone and 103 ml water. To the solution, 1.43 g charcoal (as commercially available from Ceca Eno) were added and the mixture was stirred for 15 min under nitrogen atmosphere. Afterwards, the charcoal was removed via filtration under nitrogen atmosphere and the filter cake was washed with 72 ml of an acetone/water (4/1) mixture. To the filtrate 39 ml water were added and the solution was cooled to 15° C. Subsequently 0.1 g seeding crystals obtained according to the method of Reference Example 2 were added and the mixture was stirred for 60 min leading to a white slurry. Afterwards it was cooled to 10° C. and stirred for an additional period of 30 min. 317 ml water were added during a period of 55 min. After complete addition the mixture was stirred at 10° C. for 75 min. The appearing white solid was separated via filtration and the filter cake was washed twice with 40 ml of a cold (10° C.) acetone/water (1/2) mixture. The isolated solid was dried under vacuum (<45 mbar) at 40° C. for 16 h leading to 13.0 g of posaconazole in crystalline form (18.55 mmol, 80.8% yield).

Example 2

Synthesis of Posaconazole in a Protic Solvent System Water/Isopropanol with Sodium Hydroxide as Base To a solution of 6.1 g (7.0 mmol) of compound (IVb) as a 1/1/1 crystallisate with DCM and imidazole as obtained from Reference Example 1.4 in 94 ml isopropanol and 31 ml H₂O, 0.56 g NaOH (14.0 mmol. 2 equiv.) were added. The mixture was heated to reflux. Complete conversion was observed after 2 h via HPLC analysis (HPLC method see Reference Example 1.4). The mixture was stirred under reflux for additional 21 h and the impurity profile was investigated again after 4 h, 6 h, 7 h and 23 h via HPLC analysis (HPLC method see Reference Example 1.4). All HPLC analysis were comparable to the analysis after 2 h.

This Example 2 shows that the process of the present invention provides posaconazole by a fast conversion of the starting material in a reaction solution which—after completion of the reaction—remains stable over time, i.e. wherein no increase of the impurity profile can be observed.

Example 3

Synthesis of Posaconazole in a Protic Solvent System Water/Isopropanol with Sodium Hydroxide as Base To a solution of 6.1 g (7.0 mmol) of compound (IVb) as a 1/1/1 crystallisate with DCM and imidazole as obtained from Reference Example 1.4 in 94 ml isopropanol and 31 ml H₂O, 0.28 g NaOH (7.0 mmol, 1 equivalent) were added. The mixture was heated to reflux. Complete conversion was detected via HPLC analysis after 2 h (HPLC method see Reference Example 1.4). To the reaction mixture 162 ml H₂O and 54 ml acetone were added at 52° C. After cooling to room temperature the pH value was adjusted to 7.0 by addition of 10% aqueous HCl. The mixture was cooled to 15° C. and 50 mg seeding crystals (obtained according to the method of Reference Example 2) were added. After stirring for 2 h at 15° C., 30 ml water were added slowly, and the mixture was again stirred for 16 min at 15° C. Subsequently, 105 ml water were added slowly, and the obtained precipitated solid was isolated via filtration. The filter cake was washed with a 1/2 acetone/H₂O mixture. After drying at 45° C. under reduced pressure 4.3 g (6.1 mmol, 87% yield) of posaconazole were obtained in a crystalline form.

This Example 3 clearly demonstrates fast conversion of the starting material to posaconazole and fast work-up to obtain posaconazole in a crystalline form.

Example 4

Synthesis of Posaconazole in a Protic Solvent System Water/Isopropanol with Sodium Hydroxide as Base 20.0 g (22.97 mmol) of compound (IVb) as a 1/1/1 crystallisate with DCM and imidazole as obtained from Reference Example 1.4 were dissolved in a mixture of isopropanol (104 ml) and H₂O (104 ml). Next, solid NaOH (0.9 g, 1.0 equivalent) was added and the mixture was refluxed for a period of 3 h. The solution was cooled to 70° C. and diluted with isopropylacetate (450 ml). Subsequently, the mixture was cooled to 15° C. and treated with aqueous HCl (124 ml, 15.7%). The layers were separated, and the aqueous layer was mixed with DCM (320 ml). The pH value of the mixture was adjusted to 1.0 by addition of 20% aqueous NaOH (122 ml). The aqueous layer was discarded, and the organic layer was washed with 0.1 M HCl (200 ml) followed by 5% aqueous NaHCO₃ (200 ml). The organic solvent was removed via distillation to give a solid residue. This was then taken up in a mixture of acetone (461 ml) and water (115 ml). The solution was diluted with water (39 ml), cooled to 15° C. and seeded with seed crystals obtained according to the method of Reference Example 2. The mixture was allowed to stir for 60 min at 15° C. Thereafter, the resulting suspension was further cooled to 10° C. and stirring was continued for a period of 30 min. Then, water (400 ml) was added dropwise over a period of 49 min. The suspension was left to stir for a period of 120 min at 10° C. The solid was filtered off, and the filter cake was washed twice with cold acetone/water: 1/2 (2×45 ml). The wet product was dried under reduced pressure at 40° C. for a period of 16 h to give 14.5 g (20.4 mmol, purity 99.7 area % as determined by HPLC analysis according to the HPLC method of Reference Example 1.4, 90% yield) of posaconazole in a crystalline form.

Example 5

Synthesis of Posaconazole in a Protic Solvent System of Methanol with Sodium Hydroxide as Base 5.0 g (5.74 mmol) of compound (IVb) as a 1/1/1 crystallisate with DCM and imidazole as obtained from Reference Example 1.4 were dissolved in MeOH (150 ml) and treated with 0.4 g NaOH (2 equivalents, 11.5 mmol). The mixture was heated to reflux for a period of 6 h until less than 0.1% of the starting material was detected via HPLC (HPLC method see Reference Example 1.4). The mixture was cooled to room temperature and stirred over night. The resulting solid was filtered off and washed twice with 7 ml of ice-cold MeOH. After drying at 40° C. for 16 h, 2.76 g (3.94 mmol, 69% yield) of posaconazole were isolated in a crystalline form.

Example 6

Synthesis of Posaconazole in a Protic Solvent System of Methanol/Water with Sodium Hydroxide as Base 1.0 g (1.15 mmol) of compound (IVb) as a 1/1/1 crystallisate with DCM and imidazole as obtained from Reference Example 1.4 were dissolved in a mixture of MeOH (4.0 ml) and water (4.0 ml). To this, a solution of NaOH in MeOH (0.7 ml, 0.6 equivalents, c=1 mmol/ml) was added. Subsequently, the mixture was heated to 65° C., and the temperature was kept overnight (100% conversion). The resulting suspension was cooled to room temperature, and posaconazole was isolated via filtration in a crystalline form.

Example 7

Synthesis of Posaconazole in a Protic Solvent System of Ethanol with Sodium Hydroxide as Base 1.0 g (1.15 mmol) of compound (IVb) as a 1/1/1 crystallisate with DCM and imidazole as obtained from Reference Example 1.4 were dissolved in EtOH (96%, 28.0 ml) and treated with solid NaOH (0.09 mg, 2.0 equivalents). The mixture was refluxed overnight (99.7% conversion). Then, the mixture was cooled to room temperature and crystallization was observed. Posaconazole was isolated from the suspension via filtration in a crystalline form.

Example 8

Synthesis of Posaconazole in a Protic Solvent System of Water and Ethanol with Sodium Hydroxide as Base 1.0 g (1.15 mmol) of compound (IVb) as a 1/1/1 crystallisate with DCM and imidazole as obtained from Reference Example 1.4 were dissolved in a mixture of EtOH (21.0 ml) and water (7.0 ml). To this, solid NaOH (0.09 mg, 2.0 equivalents) was added. Subsequently, the mixture was refluxed for a period of 3 h (99.9% conversion). The mixture was cooled to room temperature and crystallization was observed. Posaconazole was isolated from the suspension via filtration in a crystalline form.

Example 9

Synthesis of Posaconazole in a Protic Solvent System of Isopropanol with Sodium Hydroxide as Base 0.5 g (0.57 mmol) of compound (IVb) as a 1/1/1 crystallisate with DCM and imidazole as obtained from Reference Example 1.4 were dissolved in 6 ml isopropanol. To this, 0.86 ml of a 1M NaOH (1.5 equivalents, 0.86 mmol) solution in MeOH was added. Subsequently, the mixture was refluxed for a period of 3 h and conversion of 97% of starting material was observed via HPLC analysis (HPLC method see Reference Example 1.4).

Example 10

Synthesis of Posaconazole in a Protic Solvent System of Water and n-Butanol with Sodium Hydroxide as Base 1.0 g (1.15 mmol) of compound (IVb) as a 1/1/1 crystallisate with DCM and imidazole as obtained from Reference Example 1.4 were dissolved in 28 ml of a 10/1 mixture of n-butanol and water. To this, 2.4 ml 1M NaOH (2 equivalents) were added. Subsequently, the mixture was refluxed for a period of 1.5 h and complete conversion of the starting material was observed via HPLC analysis (HPLC method see Reference Example 1.4).

Example 11

Synthesis of Posaconazole in a Protic Solvent System of Water with Sodium Hydroxide as Base 0.5 g (0.57 mmol) of compound (IVb) as a 1/1/1 crystallisate with DCM and imidazole as obtained from Reference Example 1.4 were suspended in an aqueous solution of NaOH (6.0 ml, c=1 mmol/ml). Subsequently, the mixture was refluxed for a period of 6 h (100% conversion). After a short period, crystallization occurred. The suspension was cooled to room temperature, and posaconazole was isolated via filtration in a crystalline form.

Example 12

Synthesis of Posaconazole in a Protic Solvent System of Water and Acetone with Sodium Hydroxide as Base 0.5 g (0.57 mmol) of compound (IVb) as a 1/1/1 crystallisate with DCM and imidazole as obtained from Reference Example 1.4 were dissolved in a mixture of acetone (6.0 ml) and water (2.0 ml). To this, solid NaOH (0.046 mg, 2.0 equivalents) was added. Subsequently, the mixture was refluxed for a period of 67 h (100% conversion). The mixture was cooled to room temperature and was diluted with water. The resulting solid was filtered off, washed with a little amount of acetone/$H_2O$:3/1 and dried at 45° C. under vacuum (<50 mbar) over night. 400 mg of posaconazole were isolated in a crystalline form.

Example 13

Synthesis of Posaconazole in a Protic Solvent System of Water and Acetone with Sodium Hydroxide as Base 3 g (3.45 mmol) of compound (IVb) as a 1/1/1 crystallisate with DCM and imidazole as obtained from Reference Example 1.4 were dissolved in 87 ml of a 3/1 mixture of isopropanol and $H_2O$. The mixture was heated to reflux for 2 h until complete conversion was observed via HPLC analysis (HPLC method see Reference Example 1.4). The mixture was cooled to 40° C. and stirred at that temperature for 60 min until precipitation was observed. Subsequently, the suspension was cooled to 20° C. and 42 ml $H_2O$ were added slowly. After complete addition, the mixture was stirred for additional 60 min, and subsequently, posaconazole was isolated via filtration in a crystalline form as solvate of isopropanol.

Example 14

Posaconazole Formulation

An oral suspension containing 200 mg crystalline posaconazole per 5 ml was prepared by admixing the following components:

| Component | Mass/(mg per dosage unit of 5 ml) |
|---|---|
| Posaconazole (crystalline form) | 200 |
| Polysorbate 80, NF | 50 |
| Simethicone, NF | 15 |
| Sodium Benzoate, NF | 10 |
| Sodium Citrate Dihydrate, NF | 3 |
| Citric Acid Monohydrate, NF | 15 |
| Glycerin, NF | 500 |
| Xanthan Gum, NF | 5 |
| Corn Syrup Solids, NF | 1,382.5[1] |
| Titanium Dioxide, NF | 20 |
| Polyoxyl 40 Hydrogenated Castor Oil, NF | 870 |
| Cherry Flavor | 40 |
| Purified Water, USP | 2,689.5[2] |
| Total mass | 5,800 |

[1] Had to be adjusted according to loss on drying of the used excipient
[2] Varied with the initial mass of drug substance and Corn Syrup Solids Mixing said components was performed as follows:

About 80% of the final amount of the purified water, simethicone and polysorbate 80 were mixed at 50° C. and emulsified by homogenization (Process Vessel Fryma VME 120/95). After cooling to room temperature, posaconazole in crystalline form was added, and the obtained mixture was homogenized. Sodium citrate dihydrate, citric acid monohydrate, sodium benzoate and glycerin were added, dissolved and mixed. Corn syrup solids were premixed with xanthan gum and added to the suspension, mixed and the intermediate suspension was kept for swelling for 60 min. Subsequently, titanium dioxide was added to the suspension and mixed. After heating of the intermediate bulk suspension to 60° C. the Polyoxyl 40 Hydrogenated Castor Oil was added and homogenized for 2 h at 60° C. The homogenized suspension was then mixed at 60° C. for 2 h for re-agglomeration. After cooling to room temperature the cherry flavor was added, the suspension was mixed, and the remaining quantity of water was added and mixed. The obtained suspension was kept for 2 h at room temperature before filling into glass bottles which were closed with a screw closure.

LIST OF CITED DOCUMENTS

WO 96/33178 A1
WO 95/17407 A1
EP 1 230 231 B1
Brown et al., *J. Chem. Soc.* 2003, 125 (36), 10808-10809
M. Hepperle et. al., *Tetrahedron Lett.* 2002, 43, 3359-3363
U.S. Pat. No. 6,355,801 B1
U.S. Pat. No. 5,403,937
EP 0 736 030 A1
WO 2010/000668 A1
Remington's Pharmaceutical Sciences, 15th Ed., Mack Publishing Co., New Jersey (1991)
Greene et al., "Protective Groups in Organic Synthesis", 3$^{rd}$ Ed., Wiley-Interscience (1999)

The invention claimed is:

1. A process for the preparation of an antifungal agent of formula (V)

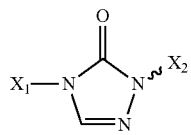

wherein $X_1$ is a residue according to formula (X1)

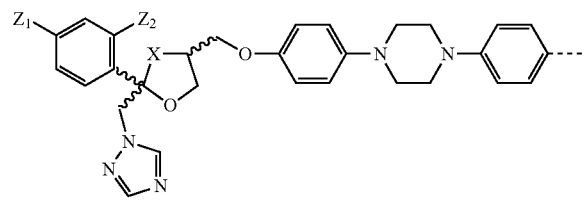

wherein $Z_1$ and $Z_2$ are independently F or Cl wherein —X— is —O— or —CH$_2$—, and wherein the dotted line in formula (X1) stands for the bond between $X_1$ and the NH group in formula (IV) and the bond between $X_1$ and the N atom in formula (V) and $X_2$ is a linear or branched, optionally substituted alkyl residue, said process comprising (1) providing a mixture comprising a compound of formula (IV)

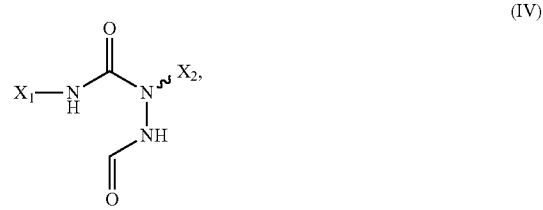

a protic solvent system, and a suitable base;
(2) heating the mixture of (1) to obtain a mixture comprising the antifungal agent of formula (V).

2. The process of claim 1, wherein in (2), the mixture is heated to a temperature in the range of from 40 to 140° C.

3. The process of claim 1, wherein in (2), the mixture is heated for a time in the range of from 0.1 to 10 h.

4. The process of claim 1, wherein the protic solvent system comprises water and/or an alcohol, and optionally at least one further organic solvent.

5. The process of claim 1, wherein the protic solvent system comprises water and an alcohol, or comprises water and a ketone.

6. The process of claim 4, wherein the alcohol comprises 1to 5 carbon atoms, and wherein the ketone comprises 3 to 9 carbon atoms.

7. The process of claim 1, wherein the protic solvent system comprises water wherein the water content of the protic solvent system is at most 25 vol-%.

8. The process of claim 1, wherein the protic solvent system is a mixture of water and isopropanol, wherein the volume ratio of water relative to isopropanol is in the range of from 1:12 to 3:1.

9. The process of claim 1, wherein the suitable base has a pK$_b$ of less than 7.

10. The process of claim 1, wherein the suitable base is at least one hydroxide, or at least one carbonate, or at least one alcoholate, or a mixture of at least one hydroxide and at least one carbonate, or a mixture of at least one hydroxide and at least one alcoholate, or a mixture of at least one carbonate and at least one alcoholate, or a mixture of at least one hydroxide and at least one carbonate and at least one alcoholate.

11. The process of claim 10, wherein the hydroxide is selected from the group consisting of an alkali metal hydroxide and an alkaline earth metal hydroxide; wherein the carbonate is selected from the group consisting of an alkali metal carbonate and an alkaline earth metal carbonate; wherein the alcoholate is selected from the group consisting of an alkali metal alcoholate and an alkaline earth metal alcoholate.

12. The process of claim 10, wherein the alcoholate is selected from the group consisting of a methanolate, an ethanolate, an isopropanolate, and an n-butanolate.

13. The process of claim 1, wherein in the mixture provided in (1), the molar ratio of the suitable base relative to the compound of formula (IV) is in the range of from 0.1:1 to 3:1.

14. The process of claim 1, wherein step (2) of heating the mixture of (1) is carried out in the absence of bis-trimethylsilyl acetamide (BSA) and a trimethylsilyl (TMS) halide.

15. The process of claim 1, wherein $X_2$ is a residue according to formula (X2)

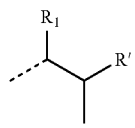

(X2)

wherein $R_1$ is H or an alkyl residue, and wherein —R' is selected from the group consisting of —H, -alkyl, and —O—R wherein —R is —H or a suitable hydroxyl protecting group, and wherein the dotted line in formula (X2) stands for the bond between $X_2$ and the N atom in formulas (IV) and (V).

16. The process of claim 15, wherein $R_1$ is an alkyl residue having from 1 to 4 carbon atoms, and wherein —R' is —O—R wherein —R is —H or a hydroxyl protecting group selected from the group consisting of —Si(CH$_3$)$_3$ and benzyl.

17. The process of claim 1, wherein the residue $X_2$ is

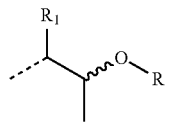

wherein $R_1$ is an alkyl residue, and
wherein —R is —H or a suitable hydroxyl protecting group;
wherein the dotted line stands for the bond between $X_2$ and the N atom in formula (IV);
wherein the compound of formula (IV) is provided by a process comprising (0.1) providing a compound of formula (I)

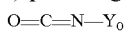

(I)

or a salt thereof,
wherein $X_1$ is an optionally substituted aryl residue;
(0.2) providing a compound of formula (IIa)

O=C=N—Y$_0$      (IIa)

wherein $Y_0$ is an optionally substituted alkyl or aryl residue;

or phosgene or a phosgene derivative of formula (IIb)

(IIb)

wherein $Y_1N$— and $Y_2N$— are the same or different optionally substituted nitrogen heterocycle moieties;

(0.3) providing a compound of formula (III)

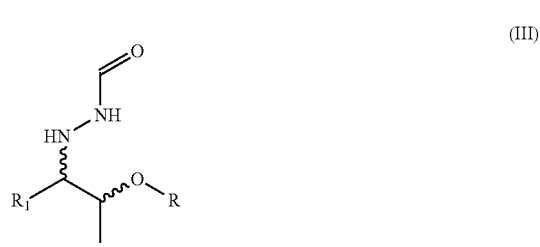

(III)

or a salt thereof, (0.4) mixing and reacting the compounds of formulas (I), (IIa) and/or (IIb), and (III) in a solvent in any order to obtain a reaction mixture comprising the compound of formula (IV')

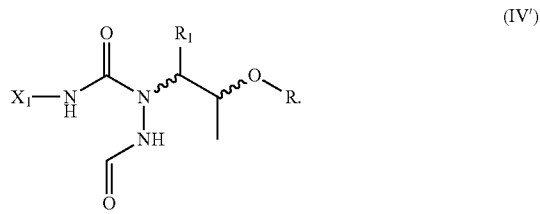

(IV')

18. The process of claim 1, wherein the compound of formula (IV) is a compound of formula (IVa)

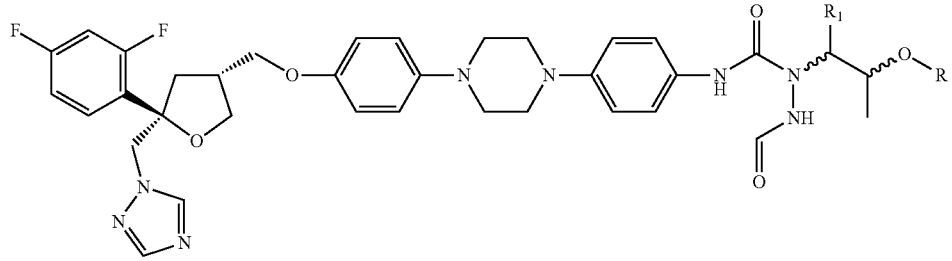

(IVa)

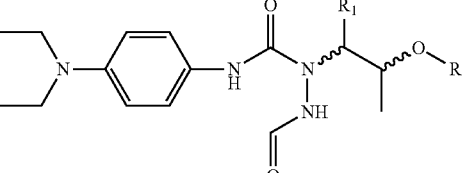

or a salt thereof,
wherein $R_1$ is an alkyl residue, and
wherein —R is —H or a suitable hydroxyl protecting group.

19. The process of claim 18, wherein the compound of formula (IV) is a compound of formula (IVb)

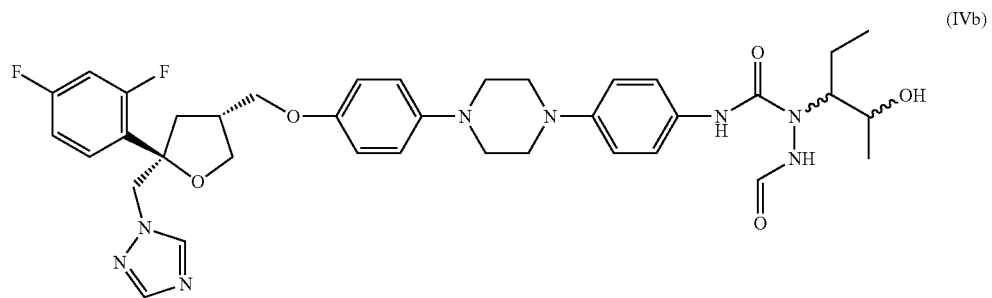 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVb)
wherein at least 95% of the molecules of compound (IV) are present as compound of formula (IVc)
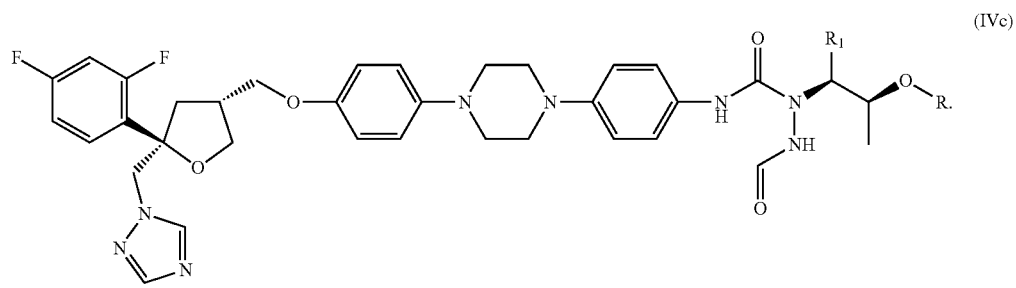
(IVc)
20. The process of claim 18, wherein the compound of formula (IV) is a compound of formula (IVb)
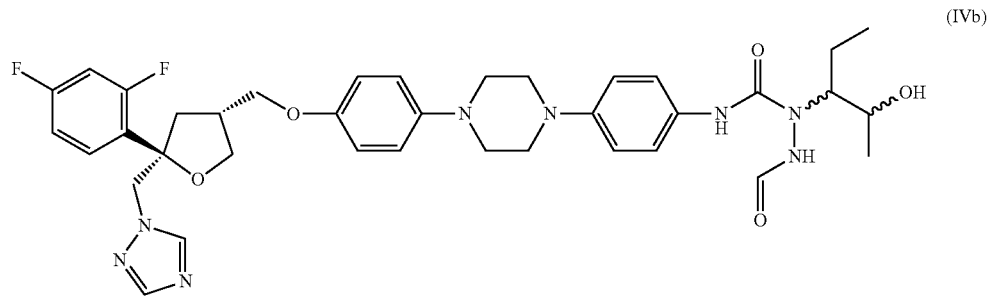 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVb)
wherein at least 95% of the molecules of compound (IV) are present as compound of formula (IVd)
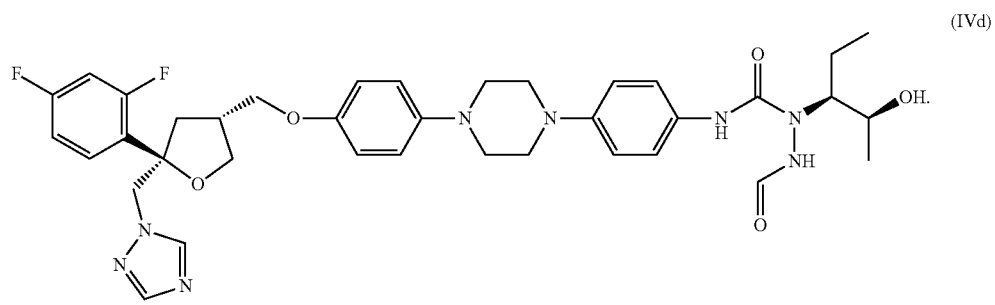 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

21. The process of claim 17, wherein the compound of formula (IV') is a compound of formula (IVa)

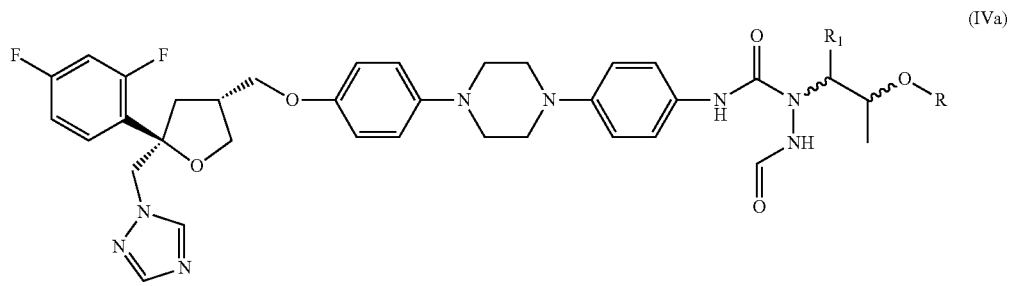

or a salt thereof,
wherein $R_1$ is an alkyl residue, and
wherein —R is —H or a suitable hydroxyl protecting group.

22. The process of claim 21, wherein the compound of formula (IV') is a compound of formula (IVb)

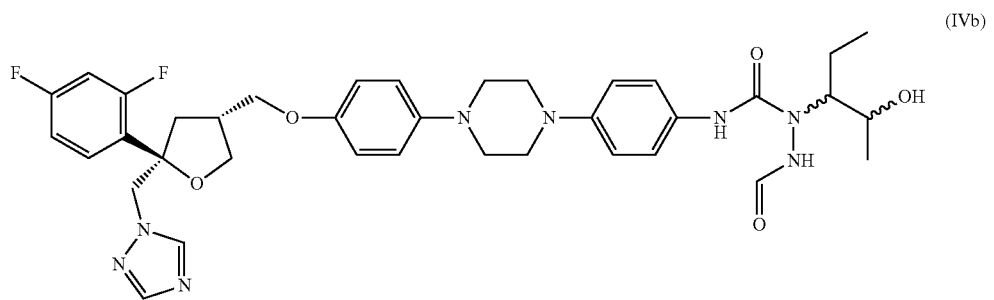 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

wherein at least 95% of the molecules of formula (IV') are present as compound of formula (IVc)

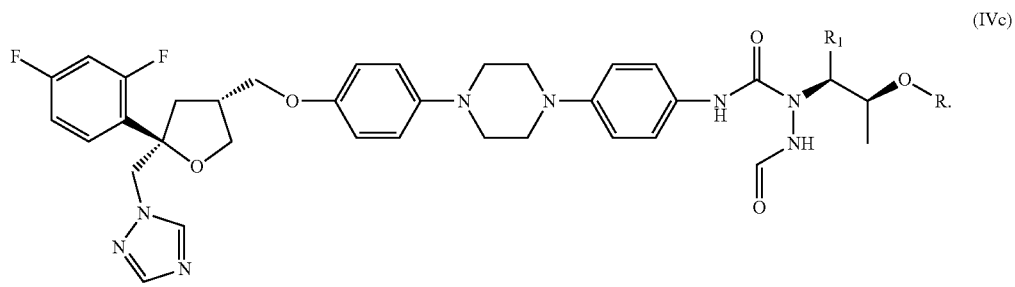

23. The process of claim 21, wherein the compound of formula (IV') is a compound of formula (IVb)

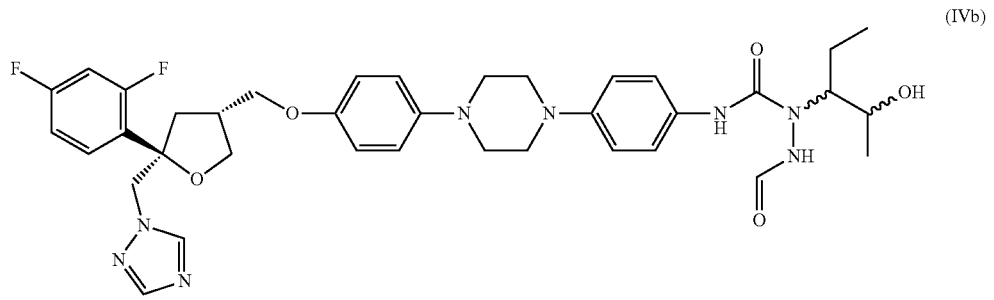 [SMILES: CCC(C(C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

wherein at least 95% of the molecules of compound (IV')
are present as compound of formula (IVd)

process further comprising
(0.5) isolating the compound of formula (IV').

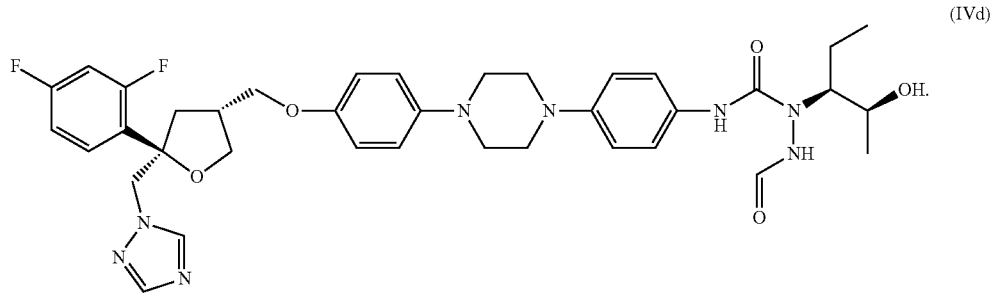 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

24. The process of claim 21, wherein $X_1$ is a residue according to formula (X1)

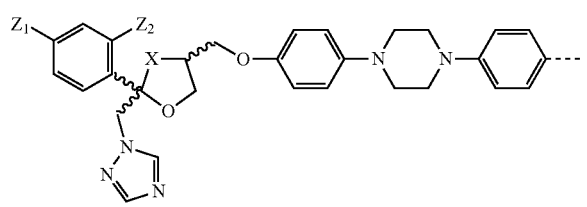
(X1)

wherein $Z_1$ and $Z_2$ are independently F or Cl, wherein —X— is —O— or —CH$_2$—, and wherein the dotted line in formula (X1) stands for the bond between $X_1$ and the NH group in formula (IV) and the bond between $X_1$ and the N atom in formula (V), and wherein the compound of formula (IV') is the compound of formula (IVd)

25. The process of claim 1, further comprising
(3) crystallizing the compound of formula (V) from the mixture obtained in (2);
(4) optionally separating the crystallized compound.

26. The process of claim 24 further comprising
(3) crystallizing the compound of formula (V) from the mixture obtained in (2);
(4) optionally separating the crystallized compound.

27. The process of claim 25, wherein after (2) and before (3), the compound of formula (V) is not subjected to an extraction stage.

28. The process of claim 25, wherein in (3), the compound of formula (V) is crystallized in the presence of a ketone.

29. The process of claim 25, wherein in (3), the compound of formula (V) is crystallized in the presence of water and an alcohol.

30. The process of claim 25, wherein in (3), the compound of formula (V) is crystallized in the presence of seed crystals.

31. The process of claim 30, wherein the compound of formula (V) is the compound of formula (Vb)

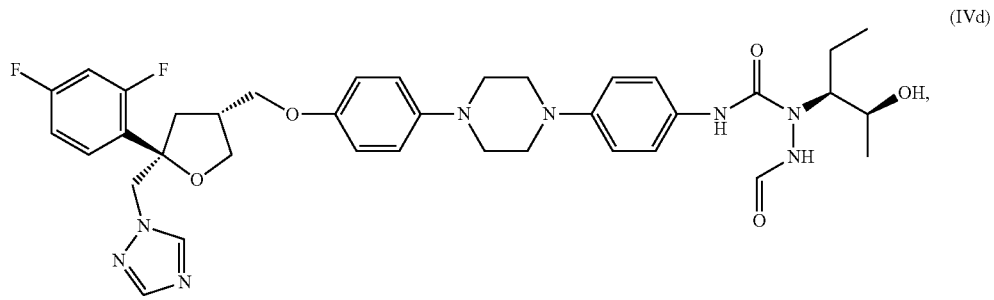 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]
(IVd)

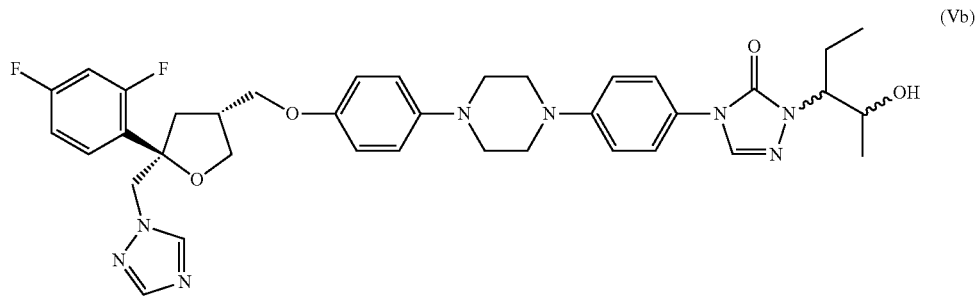 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

and the seed crystals comprise the crystalline compound of formula (Vd)

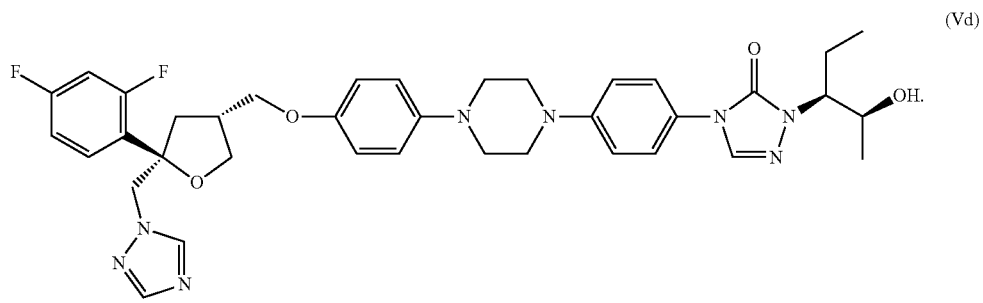 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

32. The process of claim 25, wherein crystallizing in (3) is carried out at a temperature of 35 ° C. or less, and at a pH in the range of from 5 to 14.

33. The process of claim 25, wherein the crystallized compound obtained from (3) or (4) is not subjected to a subsequent chromatography purification stage.

34. The process of claim 25, wherein the crystallized compound obtained from (3) or (4),
wherein at least 95% of the molecules of said crystalline compound are present as isomer of formula (Vd)

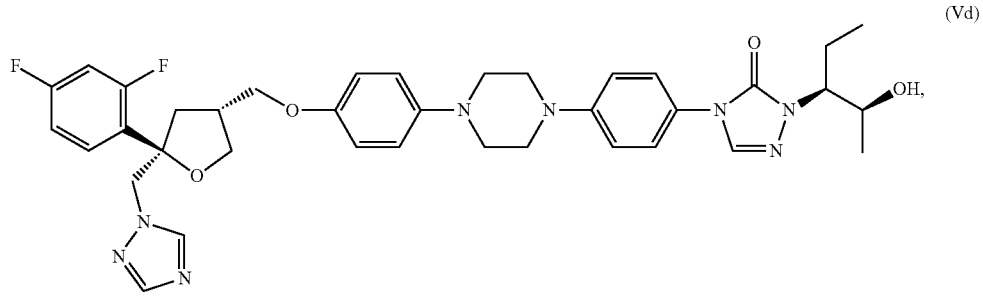 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

is re-crystallized.

35. A method of using a protic solvent system for the preparation of an antifungal agent of formula (V)

wherein $X_1$ is a residue according to formula (X1)

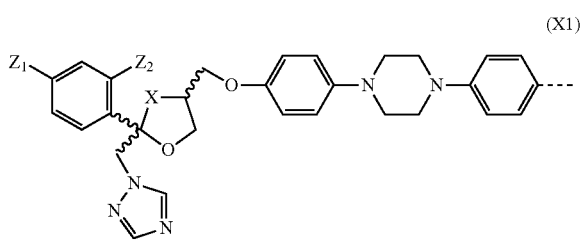

wherein $Z_1$ and $Z_2$ are independently F or Cl wherein —X— is —O— or —CH$_2$—, and wherein the dotted line in formula X1 stands for the bond between $X_1$ and the NH group formula (IV) and the bond between $X_1$ and the N atom in formula (V) and $X_2$ is a linear or branched, optionally substituted alkyl residue, using a compound of formula (IV)

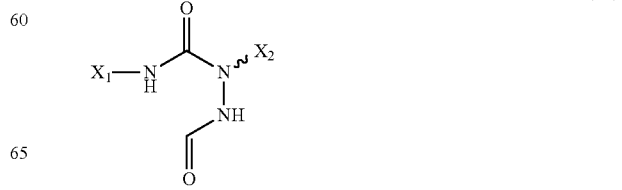

as starting material.

36. The process of claim 1, wherein in the mixture provided in (1), the molar ratio of the suitable base relative to the compound of formula (IV) is in the range of from 0.75:1 to 1.5:1.

37. The process of claim 1, wherein in the mixture provided in (1), the molar ratio of the suitable base relative to the compound of formula (IV) is in the range of from 0.5:1 to 1.05:1.

38. The process of claim 1, wherein step (2) of heating the mixture of (1) is carried out in the absence of bis-trimethylsilyl acetamide (BSA) and trimethylsilyl iodide (TMSI) and/or trimethylsilyl chloride (TMSCI).

39. The process of claim 1, wherein step (2) of heating the mixture of (1) is carried out in the absence of trialkylsilyl halide.

40. The process of claim 1, wherein step (2) of heating the mixture of (1) is carried out in the absence of silylating agent.

41. The process of claim 15, wherein $R_1$ is an alkyl residue having from 1 to 62 carbon atoms.

42. The process of claim 15, wherein $R_1$ is an alkyl residue having from 1 or 2 carbon atoms, and wherein —R' is —O—R wherein —R is —H or a hydroxyl protecting group selected from the group consisting of —Si(CH$_3$)$_3$ and benzyl.

43. The process of claim 1, wherein the residue $X_2$ is

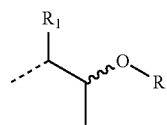

wherein $R_1$ is an alkyl residue having from 1 to 6 carbon atoms, and wherein —R is —H or a hydroxyl protecting group selected from the group consisting of —SiR$_a$R$_b$R$_c$, and optionally substituted alkyl, aryl, alkaryl or aralkyl residues, where R$_a$, R$_b$ and R$_c$ are the same or different and selected from the group consisting of optionally suitably substituted alkyl and aryl residues;
wherein the dotted line stands for the bond between $X_2$ and the N atom in formula (IV);
wherein the compound of formula (IV) is provided by a process comprising (0.1) providing a compound of formula (I)

$$X_1—NH_2 \quad (I)$$

or a salt thereof, wherein $X_1$ is an optionally substituted aryl residue;
(0.2) providing a compound of formula (IIa)

$$O=C=N—Y_0 \quad (IIa)$$

wherein $Y_0$ is an optionally substituted alkyl or aryl residue;
or, preferably, phosgene or a phosgene derivative of formula (IIb)

wherein $Y_1N$— and $Y_2N$— are the same or different optionally substituted nitrogen heterocycle moieties selected from the group consisting of imidazolyl and benzimidazolyl;
(0.3) providing a compound of formula (III)

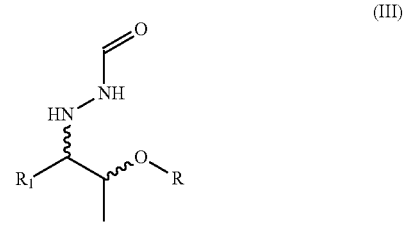

or a salt thereof,
(0.4) mixing and reacting the compounds of formulas (I), (IIa) and/or (IIb), and (III) in a solvent in any order to obtain a reaction mixture containing the compound of formula (IV')

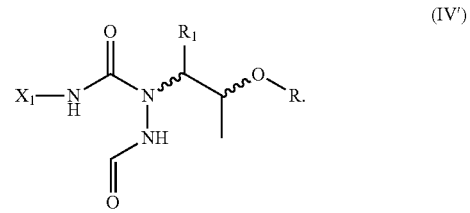

44. The process of claim 1, wherein the compound of formula (IV) and/or of formula (IV') is a crystalline compound of formula (IVb)

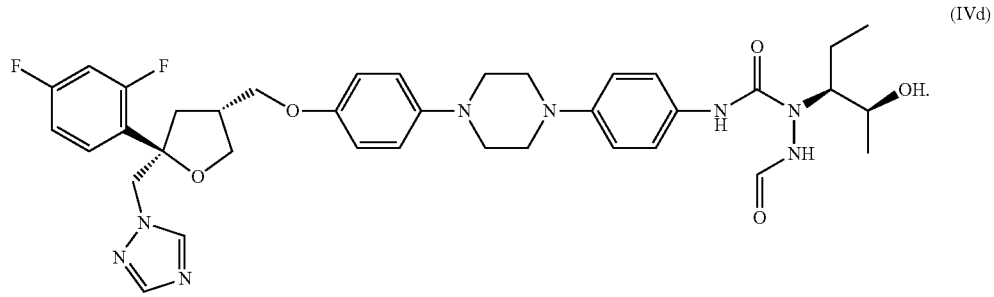 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

wherein at least 95% of the molecules of compound (IVb) are present as compound of formula (IVc)

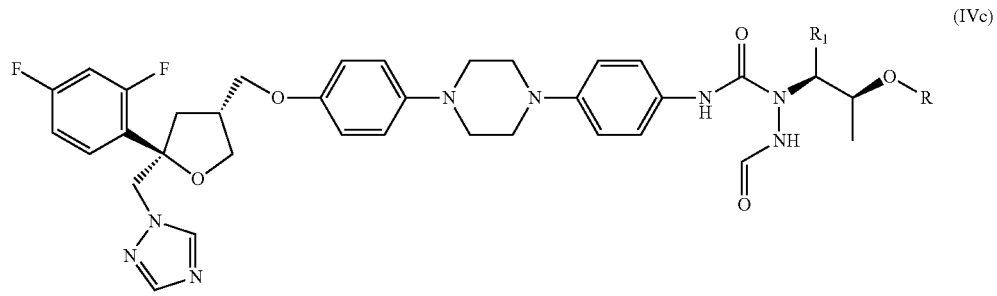

wherein $R_1$ is an alkyl residue, and wherein —R is —H or a suitable hydroxyl protecting group selected from the group consisting of —SiR$_a$R$_b$R$_c$, and optionally substituted alkyl, aryl, alkaryl or aralkyl residues, where $R_a$, $R_b$ and $R_c$ are the same or different and selected from the group consisting of substituted alkyl and aryl residues.

45. The process of claim 1, wherein the compound of formula (IV) and/or of formula (IV') is a crystalline compound of formula (IVb)

$R_c$, and optionally substituted alkyl, aryl, alkaryl or aralkyl residues, where $R_a$, $R_b$ and $R_c$ are the same or different and selected from the group consisting of optionally substituted alkyl and aryl residues.

46. The process of claim 25, wherein crystallizing in (3) is carried out at a temperature of from 0 to 20 ° C. and at a pH in the range of from 5 to 9.

47. The process of claim 25, wherein crystallizing in (3) is carried out at a temperature of from 10 to 15 ° C. and at a pH in the range of from 6 to 8.

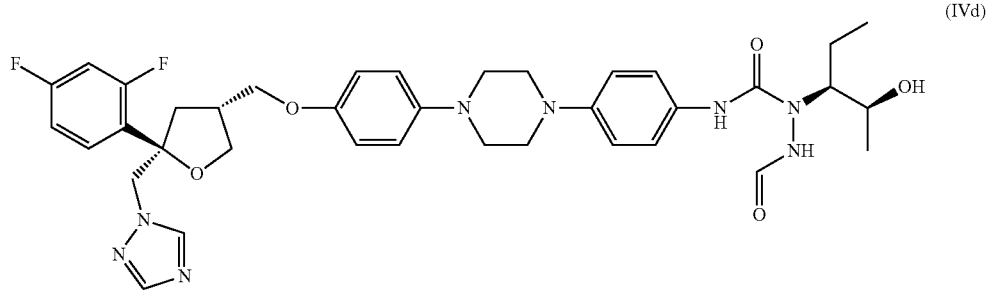 [SMILES: CC[C@@H]([C@H](C)O)N(NC=O)C(=O)Nc1ccc(N2CCN(c3ccc(OC[C@@H]4CO[C@@](Cn5cncn5)(c5ccc(F)cc5F)C4)cc3)CC2)cc1]

wherein at least 95% of the molecules of compound (IVb) are present as compound of formula (IVd)

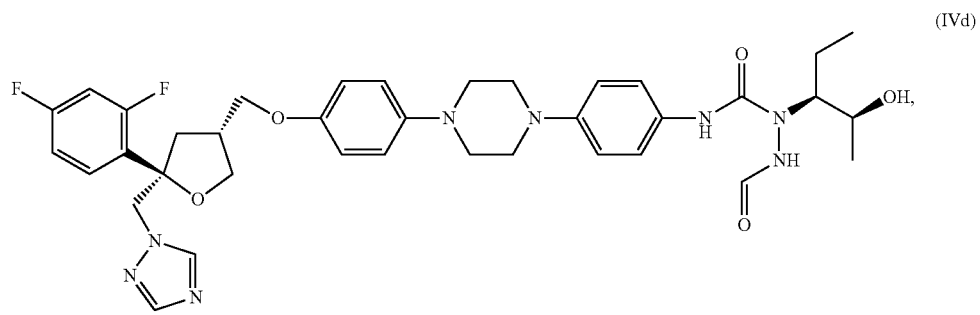

wherein $R_1$ is an alkyl residue, and wherein —R is —H or a suitable hydroxyl protecting group selected from the group consisting of —SiR$_a$R$_b$ 48. The process of claim 25, wherein the crystallized compound obtained from (3) or (4) is the compound of formula (Vb)

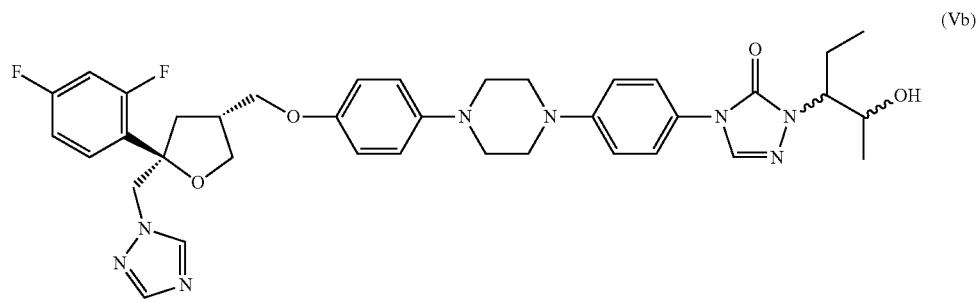 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein at least 95% of the molecules of said crystalline compound are present as isomer of formula (Vd)

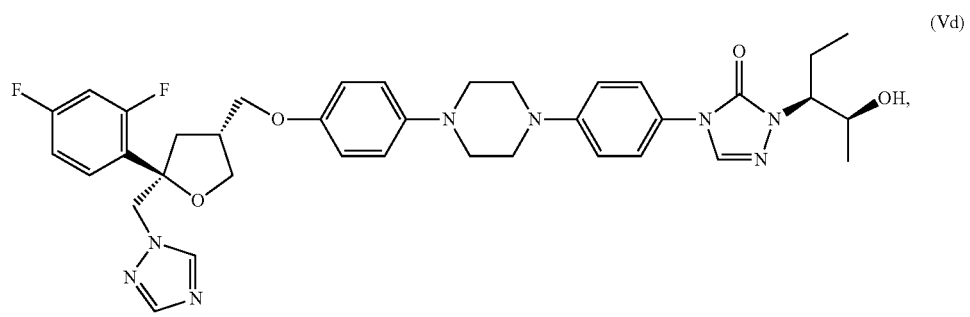 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

is re-crystallized from a mixture of acetone and water in the presence of seed crystals, said seed crystals comprising the crystalline compound of formula (Vd).

49. The process of claim 25, wherein the crystallized compound obtained from (3) or (4) is the compound of formula (Vb)

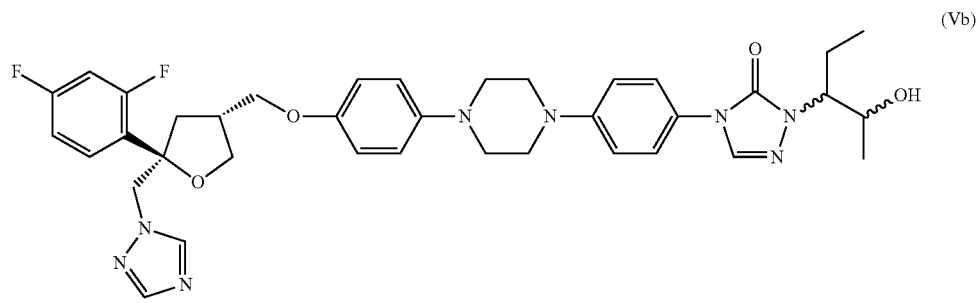 [SMILES: CCC(C(C)O)n1ncn(-c2ccc(N3CCN(c4ccc(OC[C@@H]5CO[C@@](Cn6cncn6)(c6ccc(F)cc6F)C5)cc4)CC3)cc2)c1=O]

wherein at least 95% of the molecules of said crystalline compound are present as isomer of formula (Vd)

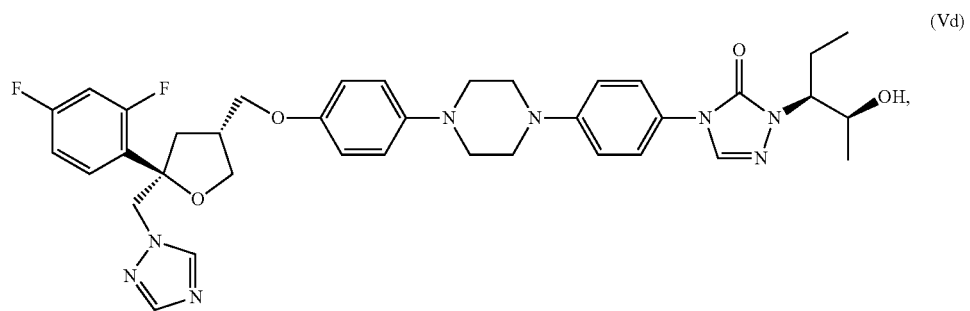 [SMILES: CC[C@@H]([C@H](C)O)n1ncn(-c2ccc(N3CCN(c4ccc(OC[C@@H]5CO[C@@](Cn6cncn6)(c6ccc(F)cc6F)C5)cc4)CC3)cc2)c1=O]

is re-crystallized.

* * * * *